(12) United States Patent
Kjeldsen et al.

(10) Patent No.: US 6,777,207 B2
(45) Date of Patent: Aug. 17, 2004

(54) METHOD FOR MAKING INSULIN PRECURSORS AND INSULIN PRECURSOR ANALOGUES HAVING IMPROVED FERMENTATION YIELD IN YEAST

(75) Inventors: Thomas Børglum Kjeldsen, Virum (DK); Svend Ludvigsen, Lynge (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/894,711

(22) Filed: Jun. 28, 2001

(65) Prior Publication Data

US 2002/0137144 A1 Sep. 26, 2002

Related U.S. Application Data

(63) Continuation-in-part of application No. 09/740,359, filed on Dec. 19, 2000, now abandoned.
(60) Provisional application No. 60/181,450, filed on Feb. 10, 2000, and provisional application No. 60/211,081, filed on Jun. 13, 2000.

(30) Foreign Application Priority Data

Dec. 29, 1999 (DK) .......................... 1999 01869
Mar. 17, 2000 (DK) .......................... 2000 00443

(51) Int. Cl.[7] .................. C07K 14/62; C12N 15/17; C12N 1/15; C12N 1/21
(52) U.S. Cl. .............. 435/69.4; 530/303; 435/252.3; 435/254.2; 435/254.21; 435/320.1; 435/325; 536/23.4; 536/23.5
(58) Field of Search ................... 530/303, 305, 530/350; 435/69.4, 320.1, 252.3, 254.2, 254.21, 325, 69.1, 69.7; 536/23.51, 23.4, 23.5

(56) References Cited

U.S. PATENT DOCUMENTS

| | | | |
|---|---|---|---|
| 5,324,641 A | 6/1994 | Jonassen et al. | 435/69.9 |
| 5,840,542 A | 11/1998 | Kang et al. | 435/69.4 |
| 5,962,267 A * | 10/1999 | Shin et al. | 435/69.4 |
| 6,537,806 B1 * | 3/2003 | Osborne et al. | 435/325 |

FOREIGN PATENT DOCUMENTS

| | | |
|---|---|---|
| EP | 0 055 945 A2 | 7/1982 |
| EP | 0055945 A2 | 7/1982 |
| EP | 0 347 845 A2 | 12/1989 |
| EP | 0163529 B1 | 8/1991 |
| EP | 0347845 B1 | 8/1993 |
| EP | 0741188 A2 | 5/1996 |
| EP | 0 741 188 A2 | 11/1996 |
| WO | WO 95/16708 | 6/1995 |
| WO | WO 01/49870 A1 | 7/2001 |

OTHER PUBLICATIONS

Bullesbach (Tetrahedron Letters 23:1877–1880, 1982).*
Jonasson et al (Eur. J. Biochem. 236:656–661, 1996).*
Taylor et al (Biochemical Journal 286(2): 619–22, 1992, abstract only cited).*
Docherty et al (Journal of Biological Chemistry 264(31): 18335–9, 1989, abstract only cited).*
Bullesbach, Chemistry of Peptides and Proteins, vol. 2, pp. 23–28 (1984).
Shin et al., Biotechnol. Prog., vol. 13, pp. 249–257 (1997).
Wei et al., Abstract, Beijing Daxue Xuebao, Ziran Kexueban, vol. 30, No. 6, (1994).
Kieldsen, Abstract, Applied Microbiology and Biotechnology, vol. 54, No. 3 (2000).
Chang et al., Biochem., J., vol. 329, pp. 631–635 (1998).
Pfeffer et al., Ann. Rev. Biochem., vol. 56, pp. 829–852 (1987).
Frank et al., Peptides, pp. 729–738 (1981).
Chan et al., Proc. Natl. Acad. Sci., vol. 78. pp. 5401–5405 (1981).
Thim et al., Proc. Natl. Acad. Sci., vol. 83, pp. 6766–6770 (1986).
Wetzel et al., Gene, vol. 16, pp. 63–71 (1981).

* cited by examiner

*Primary Examiner*—Mary E. Mosher
(74) *Attorney, Agent, or Firm*—Reza Green, Esq.; Richard W. Bork, Esq.; Marc A. Began, Esq.

(57) ABSTRACT

Novel insulin precursors and insulin precursor analogs comprising a connecting peptide (mini C-peptide) of preferably up to 15 amino acid residues and comprising at least one Gly are provided. The precursors can be converted into human insulin or a human insulin analog. The precursors will typically have a distance between B27 (atom CG2) and A1 (atom CA) of less than 5 Å.

32 Claims, 13 Drawing Sheets

```
                              EcoRI     BglII
                                       -------
 901 TCTTGCTTAA ATCTATAACT ACAAAAAACA CATACAGGAA TTCCATTCAA
     AGAACGAATT TAGATATTGA TGTTTTTTGT GTATGTCCTT AAGGTAAGTT

BglII
     -----
 951 GATCTGTTCA AACAAGAAGA TTACAAACTA TCAATTTCAT ACACAATATA
     CTAGACAAGT TTGTTCTTCT AATGTTTGAT AGTTAAAGTA TGTGTTATAT

+3               M  R  F  P  S  I  F  T  A  V  L  F
                                              PstI
                                              -------
1001 AACGATTAAA AGAATGAGAT TTCCTTCAAT TTTTACTGCA GTTTTATTCG
     TTGCTAATTT TCTTACTCTA AAGGAAGTTA AAAATGACGT CAAAATAAGC

+3 A  A  S  S  A  L  A  A  P  V  N  T  T  T     E  D  E
1051 CAGCATCCTC CGCATTAGCT GCTCCAGTCA ACACTACAAC AGAAGATGAA
     GTCGTAGGAG GCGTAATCGA CGAGGTCAGT TGTGATGTTG TCTTCTACTT

+3 T  A  Q  I  P  A  E  A  V  I  G  Y  S  D     L  E  G
1101 ACGGCACAAA TTCCGGCTGA AGCTGTCATC GGTTACTCAG ATTTAGAAGG
     TGCCGTGTTT AAGGCCGACT TCGACAGTAG CCAATGAGTC TAAATCTTCC

+3   D  F  D  V  A  V  L  P  F  S  N  T     N  N  G
1151 GGATTTCGAT GTTGCTGTTT TGCCATTTTC CAACAGCACA AATAACGGGT
     CCTAAAGCTA CAACGACAAA ACGGTAAAAG GTTGTCGTGT TTATTGCCCA

+3 L  L  F  I  N  T  T    I  A  S  I  A  A  K     E  E  G
1201 TATTGTTTAT AAATACTACT ATTGCCAGCA TTGCTGCTAA AGAAGAAGGG
     ATAACAAATA TTTATGATGA TAACGGTCGT AACGACGATT TCTTCTTCCC

+3  V  S  M  A   K  R  E   E  A  E    A  E  A  P    K  F  V
             NcoI                                                  HpaI
             ------                                                --
1251 GTATCCATGG CTAAGAGAGA AGAAGCTGAA GCTGAAGCTC AAAGTTCGT
     CATAGGTACC GATTCTCTCT TCTTCGACTT CGACTTCGAG GTTTCAAGCA

+3  N  Q  H  L  C  G  S  H  L  V    E  A  L    Y  L  V
         HpaI                                HindIII
         ----                                ------
1301 TAACCAACAC TTGTGTGGTT CTCACTTGGT TGAAGCTTTG TACTTGGTTT
     ATTGGTTGTG AACACACCAA GAGTGAACCA ACTTCGAAAC ATGAACCAAA +3 C  G  E  R  G  F  F  Y  T  D  K  G  I  V    E  Q  C
1351 GTGGTGAAAG AGGTTTCTTC TACACTGACA AGGGTATCGT TGAACAATGT
     CACCACTTTC TCCAAAGAAG ATGTGACTGT TCCCATAGCA ACTTGTTACA +3 C  T  S  I  C  S  L  Y  Q  L  E  N  Y  C  N  *
1401 TGTACTTCTA TCTGTTCTTT GTACCAATTG GAAAACTACT GTAACTAGAC
     ACATGAAGAT AGACAAGAAA CATGGTTAAC CTTTTGATGA CATTGATCTG XbaI
                 ------
1451 GCAGCCCGCA GGCTCTAGAA ACTAAGATTA ATATAATTAT ATAAAAATAT
     CGTCGGGCGT CCGAGATCTT TGATTCTAAT TATATTAATA TATTTTTATA
                              Fig. 2
```

```
                                                           EcoRI    BglII
901   TCTTGCTTAA ATCTATAACT ACAAAAAACA CATACAGGAA TTCCATTCAA
      AGAACGAATT TAGATATTGA TGTTTTTTGT GTATGTCCTT AAGGTAAGTT

BglII
951   GATCTGTTCA AACAAGAAGA TTACAAACTA TCAATTTCAT ACACAATATA
      CTAGACAAGT TTGTTCTTCT AATGTTTGAT AGTTAAAGTA TGTGTTATAT
 +3                   M  R  F  P  S  I  F  T  A  V  L  F
                                                   PstI
1001  AACGATTAAA AGAATGAGAT TCCTTCAAT TTTTACTGCA GTTTTATTCG
      TTGCTAATTT TCTTACTCTA AAGGAAGTTA AAAATGACGT CAAAATAAGC

+3 A  A  S  S   A  L  A    A  P  V  N   T  T    E  D  E
1051  CAGCATCCTC CGCATTAGCT GCTCCAGTCA ACACTACAAC AGAAGATGAA
      GTCGTAGGAG GCGTAATCGA CGAGGTCAGT TGTGATGTTG TCTTCTACTT

+3  T  A  Q  I   P  A  E   A  V  I   G  Y  S  D   L  E  G
1101  ACGGCACAAA TTCCGGCTGA AGCTGTCATC GGTTACTCAG ATTTAGAAGG
      TGCCGTGTTT AAGGCCGACT TCGACAGTAG CCAATGAGTC TAAATCTTCC

+3   D  F  D   V  A  V  L   P  F  S   N  S  T   N  N  G
1151  GGATTTCGAT GTTGCTGTTT TGCCATTTTC CAACAGCACA AATAACGGGT
      CCTAAAGCTA CAACGACAAA ACGGTAAAAG GTTGTCGTGT TTATTGCCCA

+3 L  L  F  I   N  T  T    I  A  S  I   A  A  K   E  E  G
1201  TATTGTTTAT AAATACTACT ATTGCCAGCA TTGCTGCTAA AGAAGAAGGG
      ATAACAAATA TTTATGATGA TAACGGTCGT AACGACGATT TCTTCTTCCC

+3   V  S  M  A   K  R  E   E  A  E   A  E  A  P   K  F  V
         NcoI                                           HpaI
1251  GTATCCATGG CTAAGAGAGA AGAAGCTGAA GCTGAAGCTC CAAAGTTCGT
      CATAGGTACC GATTCTCTCT TCTTCGACTT CGACTTCGAG GTTTCAAGCA

+3    N  Q  H   L  C  G  S   H  L  V   E  A  L    Y  L  V
      HpaI                                HindIII
1301  TAACCAACAC TTGTGTGGTT CTCACTTGGT TGAAGCTTTG TACTTGGTTT
      ATTGGTTGTG AACACACCAA GAGTGAACCA ACTTCGAAAC ATGAACCAAA +3   C  G  E  R   G  F  F   Y  T  D  K   D  G  K    G  I  V
1351  GTGGTGAAAG AGGTTTCTTC TACACTGACA AGGACGGTAA GGGTATCGTT
      CACCACTTTC TCCAAAGAAG ATGTGACTGT TCCTGCCATT CCCATAGCAA
```

FIG. 3A

```
     +3  E  Q  C  C    T  S  I    C  S  L    Y  Q  L  E    N  Y  C
1401     GAACAATGTT GTACTTCTAT CTGTTCTTTG TACCAATTGG AAAACTACTG
         CTTGTTACAA CATGAAGATA GACAAGAAAC ATGGTTAACC TTTTGATGAC

+3  N  *
                                      XbaI
                                      ~~~~~
1451     TAACTAGACG CAGCCCGCAG GCTCTAGAAA CTAAGATTAA TATAATTATA
         ATTGATCTGC GTCGGGCGTC CGAGATCTTT GATTCTAATT ATATTAATAT
```

FIG. 3B

```
                                                              EcoRI
                                                             ~~~~~~
 901  TTCTTGCTTA AATCTATAAC TACAAAAAAC ACATACAGGA ATTCCATTCA
      AAGAACGAAT TTAGATATTG ATGTTTTTTG TGTATGTCCT TAAGGTAAGT

951  AGAATAGTTC AAACAAGAAG ATTACAAACT ATCAATTTCA TACACAATAT
      TCTTATCAAG TTTGTTCTTC TAATGTTTGA TAGTTAAAGT ATGTGTTATA

+1              M  K  L  K  T  V  R  S  A   V  L  S
                                      BglII
                                      ~~~~~~
1001  AAACGATTAA AAGAATGAAA CTGAAAACTG TAAGATCTGC GGTCCTTTCG
      TTTGCTAATT TTCTTACTTT GACTTTTGAC ATTCTAGACG CCAGGAAAGC

+1  S  L  F  A  S  Q  V   L  G  Q   P  I  D  D  T  E  S
                            MscI
1051  TCACTCTTTG CATCTCAGGT CCTTGGCCAA CCAATTGACG ACACTGAATC
      AGTGAGAAAC GTAGAGTCCA GGAACCGGTT GGTTAACTGC TGTGACTTAG

+1  N  T  T   S  V  N  L  M  A  D  D  T  E   S  R  F
                                                 XbaI
                                                 ~~~~~~
1101  TAACACTACT TCTGTCAACT TGATGGCTGA CGACACTGAA TCTAGATTCG
      ATTGTGATGA AGACAGTTGA ACTACCGACT GCTGTGACTT AGATCTAAGC

+1 A  T  N  T   T  L  A  G  G  L  D  V  V  N   L  I  S
                                                HpaI     NcoI
                                                ~~~~~~~~ ~~
1151  CTACTAACAC TACTTTGGCT GGTGGTTTGG ATGTTGTTAA CTTGATCTCC
      GATGATTGTG ATGAAACCGA CCACCAAACC TACAACAATT GAACTAGACG

+1   M  A  K  R  E  E  G  E  P  K  F  V  N   Q  H  L  C
      NcoI                                   HpaI
      ~~~~                                   ~~~~~~
1201  ATGGCTAAGA GAGAAGAAGG TGAACCAAAG TTCGTTAACC AACACTTGTG
      TACCGATTGT CTCTTCTTCC ACTTGGTTTC AAGCAATTGG TTGTGAACAC

+1   G  S  H  L  V  E  A  L  Y  L  V  C  G  E  R  G
                       HindIII
                       ~~~~~~~
1251  TGGTTCCCAC TTGGTTGAAG CTTTGTACTT GGTTTGTGGT GAAAGAGGTT
      ACCAAGGGTG AACCAACTTC GAAACATGAA CCAAACACCA CTTTCTCCAA +1  F  F  Y  T   D  K  D   G  K  G  I   V  E  Q  C  C  T
1301  TCTTCTACAC TGACAAGGAC GGTAAGGGTA TCGTTGAACA ATGTTGTACT
      AGAAGATGTG ACTGTTCCTG CCATTCCCAT AGCAACTTGT TACAACATGA
```

FIG. 7A

```
       +1  S   I   C   S    L   Y   Q    L   E   N    Y   C   N    *
          1351  TCTATCTGTT CTTTGTACCA ATTGGAAAAC TACTGTAACT AGACGCAGCC
                AGATAGACAA GAAACATGGT TAACCTTTTG ATGACATTGA TCTGCGTCGG

XbaI
                           ~~~~~~
          1401  CGCAGGCTCT AGAAACTAAG ATTAATATAA TTATATAAAA ATATTATCTT
                GCGTCCGAGA TCTTTGATTC TAATTATATT AATATATTTT TATAATAGAA
```

FIG. 7B

```
                                  EcoRI
                                ~~~~~~~
  901  TTCTTGCTTA AATCTATAAC TACAAAAAAC ACATACAGGA ATTCCATTCA
       AAGAACGAAT TTAGATATTG ATGTTTTTTG TGTATGTCCT TAAGGTAAGT

951  AGAATAGTTC AAACAAGAAG ATTACAAACT ATCAATTTCA TACACAATAT
       TCTTATCAAG TTTGTTCTTC TAATGTTTGA TAGTTAAAGT ATGTGTTATA

+1              M  K  L  K  T  V  R  S  A  V  L  S
                                        BglII
                                       ~~~~~~
 1001  AAACGATTAA AAGAATGAAA CTGAAAACTG TAAGATCTGC GGTCCTTTCG
       TTTGCTAATT TTCTTACTTT GACTTTTGAC ATTCTAGACG CCAGGAAAGC

+1   S  L  F  A  S  Q  V  L  G  Q  P  I  D  D  T  E  S
                                MscI
                               ~~~~~~
 1051  TCACTCTTTG CATCTCAGGT CCTTGGCCAA CCAATTGACG ACACTGAATC
       AGTGAGAAAC GTAGAGTCCA GGAACCGGTT GGTTAACTGC TGTGACTTAG

+1   Q  T  T  S  V  N  L  M  A  D  D  T  E  S  A  F
 1101  TCAAACTACT TCTGTCAACT TGATGGCTGA CGACACTGAA TCTGCTTTCG
       AGTTTGATGA AGACAGTTGA ACTACCGACT GCTGTGACTT AGACGAAAGC

+1  A  T  Q  T  N  S  G  L  D  V  V  G  L  I  S  M
                                                     NcoI
                                                    ~~~~~
 1151  CTACTCAAAC TAACTCTGGT GGTTTGGATG TTGTTGGTTT GATCTCCATG
       GATGAGTTTG ATTGAGACCA CCAAACCTAC AACAACCAAA CTAGAGGTAC

+1   A  K  R  E  E  G  E  P  K  F  V  N  Q  H  L  C  G
        NcoI                            HpaI
        ~                              ~~~~~~
 1201  GCTAAGAGAG AAGAAGGTGA ACCAAAGTTC GTTAACCAAC ACTTGTGCGG
       CGATTCTCTC TTCTTCCACT TGGTTTCAAG CAATTGGTTG TGAACACGCC

+1    S  H  L  V  E  A  L  Y  L  V  C  G  E  R  G  F
                       HindIII
                      ~~~~~~
 1251  TTCCCACTTG GTTGAAGCTT TGTACTTGGT TTGCGGTGAA AGAGGTTTCT
       AAGGGTGAAC CAACTTCGAA ACATGAACCA AACGCCACTT TCTCCAAAGA +1  F  Y  T  D  K  D  G  K  G  I  V  E  Q  C  C  T  S
 1301  TCTACACTGA CAAGGACGGT AAGGGTATCG TTGAACAATG CTGTACCTCC
       AGATGTGACT GTTCCTGCCA TTCCCATAGC AACTTGTTAC GACATGGAGG
```

FIG. 8A

```
      +1   I   C   S   L   Y   Q   L   E   N   Y   C   N   *
1351     ATCTGCTCCT TGTACCAATT GGAAAACTAC TGCAACTAGA CGCAGCCCGC
         TAGACGAGGA ACATGGTTAA CCTTTTGATG ACGTTGATCT GCGTCGGGCG

XbaI
             ~~~~~~
1401     AGGCTCTAGA AACTAAGATT AATATAATTA TATAAAAATA TTATCTTCTT
         TCCGAGATCT TTGATTCTAA TTATATTAAT ATATTTTTAT AATAGAAGAA
```

FIG. 8B

```
                                                             EcoRI
                                                             -------
 901  TTCTTGCTTA AATCTATAAC TACAAAAAAC ACATACAGGA ATTCCATTCA
      AAGAACGAAT TTAGATATTG ATGTTTTTTG TGTATGTCCT TAAGGTAAGT

951  AGAATAGTTC AAACAAGAAG ATTACAAACT ATCAATTTCA TACACAATAT
      TCTTATCAAG TTTGTTCTTC TAATGTTTGA TAGTTAAAGT ATGTGTTATA

M   K   L   K   T   V   R   S   A   V   L   S
  +1                                               BglII
                                                   ------
1001  AAACGATTAA AAGAATGAAA CTGAAAACTG TAAGATCTGC GGTCCTTTCG
      TTTGCTAATT TTCTTACTTT GACTTTTGAC ATTCTAGACG CCAGGAAAGC

+1  S   L   F   A   S   Q   V   L   G   Q   P   I   D   D   T   E   S
                                      MscI
                                      ------
1051  TCACTCTTTG CATCTCAGGT CCTTGGCCAA CCAATTGACG ACACTGAATC
      AGTGAGAAAC GTAGAGTCCA GGAACCGGTT GGTTAACTGC TGTGACTTAG

+1   Q   T   T   S   V   N   L   M   A   D   D   T   E   S   A   F
1101  TCAAACTACT TCTGTCAACT TGATGGCTGA CGACACTGAA TCTGCTTTCG
      AGTTTGATGA AGACAGTTGA ACTACCGACT GCTGTGACTT AGACGAAAGC

+1  A   T   Q   T   N   S   G   L   D   V   V   G   L   I   S   M
                                                                   NcoI
                                                                   -----
1151  CTACTCAAAC TAACTCTGGT GGTTTGGATG TTGTTGGTTT GATCTCCATG
      GATGAGTTTG ATTGAGACCA CCAAACCTAC AACAACCAAA CTAGAGGTAC

+1   A   K   R   E   E   G   E   P   K   F   V   N   Q   H   L   C   G
       NcoI                                      HpaI
       -                                         ------
1201  GCTAAGAGAG AAGAAGGTGA ACCAAAGTTC GTTAACCAAC ACTTGTGCGG
      CGATTCTCTC TTCTTCCACT TGGTTTCAAG CAATTGGTTG TGAACACGCC

+1   S   H   L   V   E   A   L   Y   L   V   C   G   E   R   G   F
                     HindIII
                     -------
1251  TTCCCACTTG GTTGAAGCTT TGTACTTGGT TTGCGGTGAA AGAGGTTTCT
      AAGGGTGAAC CAACTTCGAA ACATGAACCA AACGCCACTT TCTCCAAAGA +1  F   Y   T   P   K   A   A   K   G   I   V   E   Q   C   C   T   S
             Bsu36I
             --------
1301  TCTACACTCC TAAGGCTGCT AAGGGTATTG TCGAACAATG CTGTACCTCC
      AGATGTGAGG ATTCCGACGA TTCCCATAAC AGCTTGTTAC GACATGGAGG +1   I   C   S   L   Y   Q   L   E   N   Y   C   N   *
1351  ATCTGCTCCT TGTACCAATT GGAAAACTAC TGCAACTAGA CGCAGCCCGC
      TAGACGAGGA ACATGGTTAA CCTTTTGATG ACGTTGATCT GCGTCGGGCG
                                                    XbaI
                                                    ------
1401  AGGCTCTAGA AACTAAGATT AATATAATTA TATAAAAATA TTATCTTCTT
      TCCGAGATCT TTGATTCTAA TTATATTAAT ATATTTTTAT AATAGAAGAA
```

FIG. 10

METHOD FOR MAKING INSULIN PRECURSORS AND INSULIN PRECURSOR ANALOGUES HAVING IMPROVED FERMENTATION YIELD IN YEAST

CROSS REFERENCE TO RELATED APPLICATIONS

This application is a continuation-in-part of U.S. application Ser. No. 09/740,359 filed on Dec. 19, 2000, now abandoned, and claims priority under 35 U.S.C. of 119 of Danish application no. PA 1999 01869 filed on Dec. 29, 1999, Danish application no. PA 2000 00443 filed on Mar. 17, 2000, U.S. provisional application No. 60/181,450 filed on Feb. 10, 2000, and U.S. provisional application No. 60/211,081 filed on Jun. 13, 2000, the contents of which are fully incorporated herein by reference.

BACKGROUND

Yeast organisms produce a number of proteins that have a function outside the cell. Such proteins are referred to as secreted proteins. These secreted proteins are expressed initially inside the cell in a precursor or a pre-form containing a pre-peptide sequence ensuring effective direction (translocation) of the expressed product across the membrane of the endoplasmic reticulum (ER). The pre-peptide, normally named a signal peptide, is generally cleaved off from the desired product during translocation. Once entered in the secretory pathway, the protein is transported to the Golgi apparatus. From the Golgi, the protein can follow different routes that lead to compartments such as the cell vacuole or the cell membrane, or it can be routed out of the cell to be secreted to the external medium (Pfeffer et al. (1987) Ann. Rev. Biochem. 56:829–852).

Insulin is a polypeptide hormone secreted by β-cells of the pancreas and consists of two polypeptide chains, A and B, which are linked by two inter-chain disulphide bridges. Furthermore, the A-chain features one intra-chain disulphide bridge.

The hormone is synthesized as a single-chain precursor proinsulin (preproinsulin) consisting of a prepeptide of 24 amino acid followed by proinsulin containing 86 amino acids, in the configuration: prepeptide-B-Arg Arg-C-Lys Arg-A, in which C is a connecting peptide of 31 amino acids. Arg-Arg and Lys-Arg are cleavage sites for cleavage of the connecting peptide from the A and B chains.

Three major methods have been used for the production of human insulin in microorganisms. Two involve *Escherichia coli*, with either the expression of a large fusion protein in the cytoplasm (Frank et al. (1981) in Peptides: Proceedings of the 7$^{th}$ American Peptide Chemistry Symposium (Rich & Gross, eds.), Pierce Chemical Co., Rockford, Ill. pp 729–739), or use a signal peptide to enable secretion into the periplasmic space (Chan et al. (1981) PNAS 78:5401–5404). A third method utilizes *Saccharomyces cerevisiae* to secrete an insulin precursor into the medium (Thim et al. (1986) PNAS 83:6766–6770). The prior art discloses a limited number of insulin precursors which are expressed in either *E. coli* or *Saccharomyces cerevisiae,* vide U.S. Pat. No. 5,962,267, WO 95/16708, EP 0055945, EP 0163529, EP 0347845 and EP 0741188.

SUMMARY OF THE INVENTION

The present invention features novel connecting peptides (mini C-peptides) which confer an increased production yield in insulin precursor molecules and insulin precursor analog molecules when expressed in a transformed microorganism, in particular in yeast. Such insulin precursors or insulin precursor analogs can then be converted into insulin or insulin analogs by one or more suitable, well known conversion steps.

The connecting peptides of the present invention contain at least one Gly and will generally be shorter than the natural human C peptide which, including the flanking dibasic cleavage sites, consists of 35 amino acids. Thus the novel connecting peptides will in general not be of more than 15 amino acid residues in length and preferably not more than 10 amino acid residues. Typically the novel connecting peptides will be of up to 9, 8, 7 or 5 amino acid residues and will preferably not be of more than 4 amino acid residues in length.

As in the natural human insulin molecule, the connecting peptide will contain a cleavage site at its C and N termini enabling in vitro cleavage of the connecting peptide from the A and B chains. Such cleavage sites may be any convenient cleavage sites known in the art, e.g. a Met cleavable by cyanogen bromide; a single basic amino acid residue or a pair of basic amino acid residues (Lys or Arg) cleavable by trypsin or trypsin like proteases; *Acromobactor lyticus* protease or by a carboxypeptidase protease. The cleavage site enabling cleavage of the connecting peptide from the A-chain is preferably a single basic amino acid residue Lys or Arg, preferably Lys.

Alternatively cleavage of the connecting peptide from the B chain may be enabled by cleavage at the natural $Lys^{B29}$ amino acid residue in the B chain giving rise to a desB30 insulin precursor or desB30 insulin precursor analog. The desired B30 amino acid residue may then be added by well known in vitro, enzymatic procedures.

In one embodiment the connecting peptide will not contain two adjacent basic amino acid residues (Lys,Arg). In this embodiment, cleavage from the A-chain may be accomplished at a single Lys or Arg located at the N-terminal end of the A-chain and the natural Lys in position B29 in the B-chain.

The connecting peptide may comprise more than one Gly but preferably not more than 5. The connecting peptide will preferably not comprise more than 3 Gly and most preferred it will only comprise a single Gly. The Gly may be immediately N-terminal to the cleavage site adjacent to the A chain.

Furthermore, the B27 (atom CG2) will typically have a proximity to the A1 (atom CA) of less than 5 Å.

Accordingly, in one aspect the invention is related to insulin precursors or insulin precursor analogs comprising a connecting peptide (C-peptide) being cleavable from the A and B chains said connecting peptide comprising at least one Gly, wherein the B27 (atom CG2) has a proximity to the A1 (atom CA) of less than 5 Å.

In another aspect, the present invention is related to insulin precursors or insulin precursor analogs comprising a connecting peptide (C-peptide) being cleavable from the A and B chains said connecting peptide comprising at least one Gly and a cleavage site enabling cleavage of the peptide bond between the A-chain and the connecting peptide, wherein one Gly is immediately N-terminal to said cleavage site.

In another aspect, the present invention is related to insulin precursors or insulin precursor analogs comprising a connecting peptide (C-peptide) being cleavable from the A and B chains said connecting peptide comprising at least one Gly, wherein the connecting peptide is of up to 6 amino acid residues in length.

In a further aspect, the present invention is related to insulin precursors or insulin precursor analogs comprising a sequence of formula:

B(1–27)-X$_3$-X$_2$-X$_1$-Y-A(1–21), wherein

X$_1$ comprises 1–5 amino acid residues in length comprising at least one Gly,

X$_2$ is one of Pro, Lys, Ala, Arg or Pro-Thr at position 29 of the B chain,

X$_3$ is one of Pro, Asp, Lys, or Ile at position 28 of the B chain, and

Y is Lys or Arg.

In one embodiment X$_1$ is 1–4, 1–3 or 1–2 amino acid residues in length.

In a further aspect, the present invention is related to insulin precursors or insulin precursor analogs comprising a sequence of formula:

B(1–27)—X$_3$—X$_2$—X$_1$—Y—A(1–21), wherein

X$_1$ comprises a Gly immediately N-terminal to Y,

X$_2$ is one of Pro, Lys, Ala, Arg or Pro-Thr at position 29 of the B chain,

X$_3$ is one of Pro, Asp, Lys, or Ile at position 28 of the B chain, and

Y is Lys or Arg.

In one embodiment, X$_1$ is 1–15, 1–10, 1–8, 1–5 or 1–3 amino acid residues in length.

In a further aspect, the present invention is related to insulin precursors or insulin precursor analogs comprising a sequence of formula:

B(1–27)—X$_3$—X$_2$—X$_1$—Y—A(1–21), wherein

X$_1$ comprises at least one Gly,

X$_2$ is one of Pro, Lys, Ala, Arg or Pro-Thr at position 29 of the B chain,

X$_3$ is one of Pro, Asp, Lys, or Ile at position 28 of the B chain, and

Y is Lys or Arg, and wherein the B27 (atom CG2) has a proximity to the A1 (atom CA) of less than 5 Å.

In this embodiment X$_1$ is typically 1–15, 1–10, 1–9, 1–8, 1–5, 1–4 or 1–3 amino length.

In the above formula X$_1$ will typically contain 1–5 Gly, preferably 1–3 and more preferred only one Gly molecule.

The amino acid residues in X$_1$ can be any codable amino acid residue and may be the same or different with the only proviso that at least one amino acid residue in X$_1$ is Gly.

In one embodiment, X$_3$ is Asp and X$_2$ is Lys. This embodiment encompasses the insulin precursor analogs containing an Asp in position B28 of the B chain (termed hereinafter "Asp$^{B28}$IP"). In another embodiment X$_2$ is Lys and X$_3$ is Pro. In a further embodiment the sequence X$_1$—Y is selected from the group of: (a) Glu-Glu-Gly-Lys(SEQ ID NO:1, (b) Glu-Gly-Lys, (c) Ser-Gly-Lys, (d) Asn-Gly-Lys, (e) Thr-Gly-Lys, (f) Asp-Gly-Lys, (g) Met-Gly-Lys, (h) Ala-Gly-Lys, (i) His-Gly-Lys and (j) Gly-Lys.

In still further specific embodiments, X$_1$ is 1–3 amino acid residues; X$_3$ is Lys and X$_2$ is Pro. In a further embodiment, X$_1$ is 1–3 amino acid residues, X$_3$ is Asp and X$_2$ is Lys. In another embodiment X$_2$ is Pro, X$_3$ is Lys and X$_1$ is 1–2 amino acid residues of which one is Trp or Phe.

In another embodiment X$_3$ is Lys, X$_2$ is Pro-Thr and X$_1$ consists of up to 15 amino acid residues of which one is Gly. In this embodiment X$_1$ will contain a cleavage site at the C-terminal end, e.g. a mono basic or dibasic (Lys, Arg) cleavage site.

In a specific embodiment, the mini C-peptide comprises the sequence Glu-Gly-Lys, Asn-Gly-Lys, or Asp-Gly-Lys.

In a still further aspect, the present invention is related to insulin precursors comprising a sequence of formula:

B(1–29)—X$_1$—Y—A(1–21), wherein

X$_1$ is up to 5 amino acid residues in length and Y is a cleavage site.

X$_1$ may be in a further embodiment be of 1–4, 1–3 or 1–2 amino acid residues in length. In another embodiment Y is Lys or Arg. In a further embodiment X$_1$ is GluGly; GluGluGly; SerGly; AsnGly, ThrGly, AspGly; MetGly; AlaGly or HisGly. Thus the sequence X$_1$—Y can be (a) Glu-Glu-Gly-Lys(SEQ ID NO:1, (b) Glu-Gly-Lys, (c) Ser-Gly-Lys, (d) Asn-Gly-Lys, (e) Thr-Gly-Lys, (f) Asp-Gly-Lys, (g) Met-Gly-Lys, (h) Ala-Gly-Lys, or (i) His-Gly-Lys.

The present invention is also related to polynucleotide sequences which code for the claimed insulin precursors or insulin precursor analogs. In a further aspect the present invention is related to vectors containing such polynucleotide sequences and to host cells containing such polynucleotide sequences or vectors.

In another aspect, the invention relates to a process for producing the insulin precursors or insulin precursor analogs in a host cell, said method comprising (i) culturing a host cell comprising a polynucleotide sequence encoding the insulin precursors or insulin precursor analogs of the invention under suitable conditions for expression of said precursor or precursor analog; and (ii) isolating the precursor or precursor analog from the culture medium.

In still a further aspect, the invention relates to a process for producing insulin or insulin analogs in a host cell, said method comprising (i) culturing a host cell comprising a polynucleotide sequence encoding an insulin precursor or insulin precursor analogs of the invention; (ii) isolating the precursor or precursor analog from the culture medium and (iii) converting the precursor or precursor analog into insulin or an insulin analog by in vitro enzymatic conversion.

In one embodiment of the present invention the host cell is a yeast host cell and in a further embodiment the yeast host cell is selected from to the genus Saccharomyces. In a further embodiment the yeast host cell is selected from the species *Saccharomyces cerevisiae*.

In a related aspect, the invention features a mini C-peptide in an insulin precursor or insulin precursor analog wherein the amino acid residues of the C-peptide exhibit sufficient flexibility to allow several geometric arrangements of the C-peptide to accommodate an atomic distance between B27 CG2 and A1 CA less than 5 Å.

BRIEF DESCRIPTION OF THE DRAWINGS

FIG. 2 is the DNA sequence and inferred amino acid sequence of the encoded fusion protein (α-factor-leader-EEAEAEAPK(SEQ ID NO:3)-ASP$^{B28}$IP portion of pAK1150 used as PCR template (SEQ ID NO:4 and 5).

FIG. 3 is the DNA sequence encoding a leader-Asp$^{B28}$IP fusion protein with a synthetic mini C-peptide (DGK or AspGlyLys) generated by randomized optimization (SEQ ID NO:6 and 7). The mini C-peptide (DGK) is indicated by underlining.

FIG. 7 is DNA and inferred amino acid sequence of the expression cassette expressing the YAP3-TA39-GluGluGlyGluProLys(SEQ ID NO:8)-$Asp^{B28}IP$ fusion protein with a synthetic mini C-peptide (DGK or AspGlyLys) (SEQ ID NO:9 and 10).

FIG. 8 is DNA and inferred amino acids sequences of the expression cassette expressing the YAP3-TA57-GluGluGlyGluProLys(SEQ ID NO:8)-$Asp^{B28}IP$ fusion protein with a synthetic mini C-peptide (DGK or AspGlyLys) (SEQ ID NOS: 11 and 12).

Figure 1:
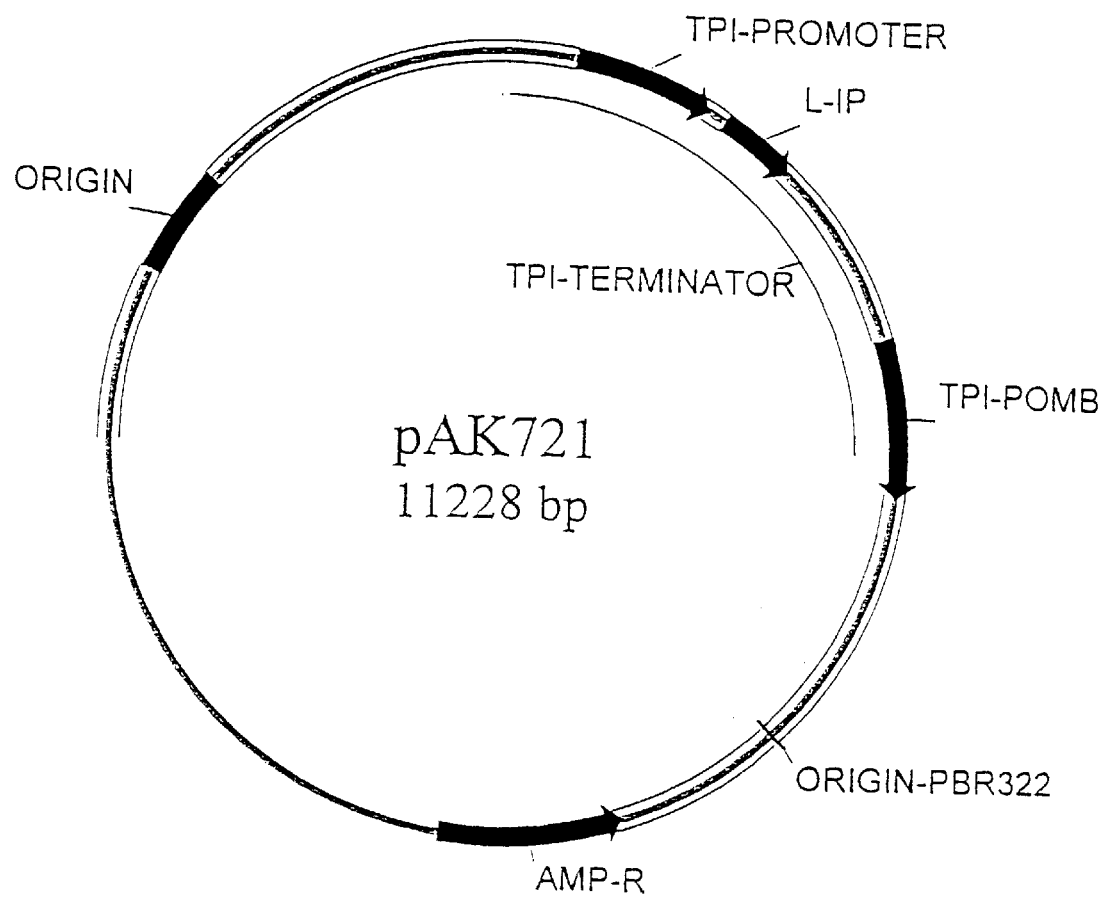
FIG. 1 represents the pAK721 *S. cerevisiae* expression plasmid expressing the LA19 leader-EEAEAEAEPK(SEQ ID NO:2)-IP(AlaAlaLys) fusion protein.

DETAILED DESCRIPTION
Abbreviations and Nomenclature

By "connecting peptide" or "C-peptide" is meant the connection moiety "C" of the B-C-A polypeptide sequence of a single chain preproinsulin-like molecule. Specifically, in the natural insulin chain, the C-peptide connects position 30 of the B chain and position 1 of the A chain. A "mini C-peptide" or "connecting peptide" such as those described herein, connect B29 or B30 to A1, and differ in sequence and length from that of the natural C-peptide.

By "IP" is meant a single-chain insulin precursor in which a desB30 chain is linked to the A chain of insulin via a connecting peptide. The single-chain insulin precursor will contain correctly positioned disulphide bridges (three) as in human insulin.

With "desB30" or "B(1–29)" is meant a natural insulin B chain lacking the B30 amino acid residue, "A(1–21)" means the natural insulin A chain, "B(1–27)" means the natural B chain lacking the B28, B29, and B30 amino acid residues; "$Asp^{B28}IP$" means a single-chain insulin precursor with aspartic acid at position 28 of the B-chain and no C-peptide (B29 is linked to A1). The mini C-peptide and its amino acid sequence is indicated in the three letter amino acid code in parenthesis following the IP; Thus "$Asp^{B28}IP$(MetTrpLys)" means a single-chain insulin precursor with aspartic acid at position 28 of the B-chain and a mini C-peptide with the sequence Met-Trp-Lys connecting B29 to A1.

By "insulin precursor" is meant a single-chain polypeptide which by one or more subsequent chemical and/or enzymatic processes can be converted into human insulin.

By "insulin precursor analog" is meant an insulin precursor molecule having one or more mutations, substitutions, deletions and or additions of the A and/or B amino acid chains relative to the human insulin molecule. The insulin analogs are preferably such wherein one or more of the naturally occurring amino acid residues, preferably one, two, or three of them, have been substituted by another codable amino acid residue. In one embodiment, the instant invention comprises analog molecules having position 28 of the B chain altered relative to the natural human insulin molecule. In this embodiment, position 28 is modified from the natural Pro residue to one of Asp, Lys, or Ile. In a preferred embodiment, the natural Pro residue at position B28 is modified to an Asp residue. In another embodiment Lys at position B29 is modified to Pro; Also, Asn at position A21 may be modified to Ala, Gln, Glu, Gly, His, Ile, Leu, Met, Ser, Thr, Trp, Tyr or Val, in particular to Gly, Ala, Ser, or Thr and preferably to Gly. Furthermore, Asn at position B3 may be modified to Lys. Further examples of insulin precursor analogs are des(B30) human insulin, insulin analogs wherein $Phe^{B1}$ has been deleted; insulin analogs wherein the A-chain and/or the B-chain have an N-terminal extension and insulin analogs wherein the A-chain and/or the B-chain have a C-terminal extension. Thus one or two Arg may be added to position B1.

The term "immediately N-terminal to" is meant to illustrate the situation where an amino acid residue or a peptide sequence is directly linked at its C-terminal end to the N-terminal end of another amino acid residue or amino acid sequence by means of a peptide bond.

In the present context, the term "functional analog of insulin" and the like, is meant to indicate a polypeptide with a similar biological action as the native human insulin protein.

By a distance shorter than 5 Å between two amino acid residues is meant the shortest interatomic distance less than 5 Å between any atom in the first amino acid and any atom in the second amino acid. Atomic distances are measured from three-dimensional structures of the molecule determined either by NMR (Wüthrich, K., 1986, NMR of Proteins and Nucleic Acids, Wiley, N.Y.) or by X-ray crystallography (Drenth, J., 1994, Principles of Protein X-ray crystallography, Springer Verlag Berlin). A distance from one amino acid to another is measured as the shortest inter-atomic distance between any atom in the first amino acid and any atom in the second amino acid if not stated differently.

The present invention features novel mini C-peptides connecting position 29 of the insulin B chain and position 1 of the insulin A chain which significantly increased production yields in a yeast host cell. By the term "significantly increased production," "increased fermentation yield," and the like, is meant an increase in secreted amount of the insulin precursor molecule or insulin precursor analog molecule present in the culture supernatant compared to the yield of an insulin precursor or insulin precursor analog with no aromatic amino acid residue in the mini C peptide. An "increased" fermentation yield is an absolute number larger than the control; preferably, the increase is 50% or more larger than the control ($AspB^{28}IP$) level; even more preferably, the increase is 100% or more larger than control levels.

"POT" is the Schizosaccharomyces pombe triose phosphate isomerase gene, and "TP11" is the S. cerevisiae triose phosphate isomerase gene.

By a "leader" is meant an amino acid sequence consisting of a pre-peptide (the signal peptide) and a pro-peptide.

The term "signal peptide" is understood to mean a pre-peptide which is present as an N-terminal sequence on the precursor form of a protein. The function of the signal peptide is to allow the heterologous protein to facilitate translocation into the endoplasmic reticulum. The signal peptide is normally cleaved off in the course of this process. The signal peptide may be heterologous or homologous to the yeast organism producing the protein. A number of signal peptides which may be used with the DNA construct of the invention including yeast aspartic protease 3 (YAP3) signal peptide or any functional analog (Egel-Mitani et al. (1990) YEAST 6:127–137 and U.S. Pat. No. 5,726,038) and the α-factor signal of the MFα1 gene (Thorner (1981) in *The Molecular Biology of the Yeast Saccharomyces cerevisiae*, Strathern et al., eds., pp 143–180, Cold Spring Harbor Laboratory, NY and U.S. Pat. No. 4,870,00.

The term "pro-peptide" means a polypeptide sequence whose function is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The pro-peptide may be the yeast α-factor pro-peptide, vide U.S. Pat. Nos. 4,546,082 and 4,870,008. Alternatively, the pro-peptide may be a synthetic pro-peptide, which is to say a pro-peptide not found in nature. Suitable synthetic pro-peptides are those disclosed in U.S. Pat. Nos. 5,395,922; 5,795,746; 5,162,498 and WO 98/32867. The pro-peptide will preferably contain an endopeptidase processing site at the C-terminal end, such as a Lys-Arg sequence or any functional analog thereof.

The polynucleotide sequence of the invention may be prepared synthetically by established standard methods, e.g. the phosphoamidite method described by Beaucage et al. (1981) Tetrahedron Letters 22:1859–1869, or the method described by Matthes et al. (1984) EMBO Journal 3:801–805. According to the phosphoamidite method, oligonucleotides are synthesized, for example, in an automatic DNA synthesizer, purified, duplexed and ligated to form the synthetic DNA construct. A currently preferred way of preparing the DNA construct is by polymerase chain reaction (PCR).

The polynucleotide sequence of the invention may also be of mixed genomic, cDNA, and synthetic origin. For example, a genomic or cDNA sequence encoding a leader peptide may be joined to a genomic or cDNA sequence encoding the A and B chains, after which the DNA sequence may be modified at a site by inserting synthetic oligonucleotides encoding the desired amino acid sequence for homologous recombination in accordance with well-known procedures or preferably generating the desired sequence by PCR using suitable oligonucleotides.

The invention encompasses a vector which is capable of replicating in the selected microorganism or cell line and which carries a polynucleotide sequence encoding the insulin precursors or insulin precursor analogs of the invention. The recombinant vector may be an autonomously replicating vector, i.e., a vector which exists as an extra-chromosomal entity, the replication of which is independent of chromosomal replication, e.g., a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used. The vectors may be linear or closed circular plasmids and will preferably contain an element(s) that permits stable integration of the vector into the host cell's genome or autonomous replication of the vector in the cell independent of the genome.

In a preferred embodiment, the recombinant expression vector is capable of replicating in yeast organisms. Examples of sequences which enable the vector to replicate in yeast are the yeast plasmid 2 μm replication genes REP 1–3 and origin of replication.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase), sC (sulfate adenyltransferase) and trpC (anthranilate synthase. Suitable markers for yeast host cells are ADE2, HIS3, LEU2, LYS2, MET3, TRP1, and URA3. A preferred selectable marker for yeast is the *Schizosaccharomyces pompe* TPI gene (Russell (1985) Gene 40:125–130).

In the vector, the polynucleotide sequence is operably connected to a suitable promoter sequence. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), and *Bacillus licheniformis* penicillinase gene (penP). Examples of suitable promoters for directing the transcription in a filamentous fungal host cell are promoters obtained from the genes for *Aspergillus oryzae* TAKA amylase, *Rhizomucor miehei* aspartic proteinase, *Aspergillus niger* neutral alpha-amylase, and *Aspergillus niger* acid stable alpha-amylase. In a yeast host, useful promoters are the *Saccharomyces cerevisiae* Ma1, TPI, ADH or PGK promoters.

The polynucleotide construct of the invention will also typically be operably connected to a suitable terminator. In yeast a suitable terminator is the TPI terminator (Alber et al. (1982) J. Mol. Appl. Genet. 1:419–434).

The procedures used to ligate the polynucleotide sequence of the invention, the promoter and the terminator, respectively, and to insert them into suitable yeast vectors containing the information necessary for yeast replication, are well known to persons skilled in the art. It will be understood that the vector may be constructed either by first preparing a DNA construct containing the entire DNA sequence of the invention, and subsequently inserting this fragment into a suitable expression vector, or by sequentially inserting DNA fragments containing genetic information for the individual elements (such as the signal, pro-peptide, mini C-peptide, A and B chains) followed by ligation.

The present invention also relates to recombinant host cells, comprising a polynucleotide sequence encoding the insulin precursors or the insulin precursor analogs of the invention. A vector comprising such polynucleotide sequence is introduced into the host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, Streptomyces cell, or gram negative bacteria such as *E. coli* and Pseudomonas sp. Eukaryote cells may be mammalian, insect, plant, or fungal cells. In a preferred embodiment, the host cell is a yeast cell The yeast organism used in the process of the invention may be any suitable yeast organism which, on cultivation, produces large amounts of the insulin precursor and insulin precursor analogs of the invention. Examples of suitable yeast organisms are strains selected from the yeast species *Saccharomyces cerevisiae, Saccharomyces kluyveri, Schizosaccharomyces pombe, Saccharomyces uvarum, Kluyveromyces lactis, Hansenula polymorpha, Pichia pastoris, Pichia methanolica, Pichia kluyveri, Yarrowia lipolytica,* Candida sp., *Candida utilis, Candida cacaoi,* Geotrichum sp., and *Geotrichum fermentans.*

The transformation of the yeast cells may for instance be effected by protoplast formation followed by transformation in a manner known per se. The medium used to cultivate the cells may be any conventional medium suitable for growing yeast organisms. The secreted insulin precursor or insulin precursor analogs of the invention, a significant proportion of which will be present in the medium in correctly processed form, may be recovered from the medium by conventional procedures including separating the yeast cells from the medium by centrifugation, filtration or catching the insulin precursor or insulin precursor analog by an ion exchange matrix or by a reverse phase absorption matrix, precipitating the proteinaceous components of the supernatant or filtrate by means of a salt, e.g. ammonium sulphate, followed by purification by a variety of chromatographic procedures, e.g. ion exchange chromatography, affinity chromatography, or the like.

The insulin precursors and insulin precursor analogs of the invention may be expressed with an N-terminal amino acid residue extension, as described in U.S. Pat. No. 5,395,922, and European Patent No. 765,395A, both of which patents are herein specifically incorporated by reference. The extension is found to be stably attached to the insulin precursor or insulin precursor analogs of the invention during fermentation, protecting the N-terminal end of the insulin precursor or insulin precursor analog against the proteolytic activity of yeast proteases such as DPAP. The presence of an N-terminal extension on the insulin precursor or insulin precursor analog may also serve as a protection of the N-terminal amino group during chemical processing of the protein, i.e. it may serve as a substitute for a BOC (t-butyl-oxycarbonyl) or similar protecting group.

The N-terminal extension may be removed from the recovered insulin precursor or insulin precursor analog by means of a proteolytic enzyme which is specific for a basic amino acid (e.g., Lys) so that the terminal extension is cleaved off at the Lys residue. Examples of such proteolytic enzymes are trypsin or *Achromobacter lyticus* protease.

After secretion to the culture medium and recovery, the insulin precursor or insulin precursor analogs of the invention will be subjected to various in vitro procedures to remove the possible N-terminal extension sequence and the mini C-peptide to give insulin or the desired insulin analog. Such methods include enzymatic conversion by means of trypsin or an *Achromobacter lyticus* protease in the presence of an L-threonine ester followed by conversion of the threonine ester of the insulin or insulin analog into insulin or the insulin analog by basic or acid hydrolysis as described in U.S. Pat. Nos. 4,343,898 or 4,916,212 or Research Disclosure, September 1994/487 the disclosures of which are incorporated by reference hereinto. Cleavage of the connecting peptide from the B chain is preferentially enabled by cleavage at the natural $Lys^{B29}$ amino acid residue in the B chain giving rise to a desB30 insulin precursor or desB30 insulin precursor analogue. If the insulin precursor is to be converted into human insulin, the B30 Thr amino acid residue (Thr) can be added by in vitro, enzymatic procedures such methods include enzymatic conversion by means of trypsin or an *Achromobacter lyticus* protease (see above). The desB30 insulin may also be converted into an acylated insulin as disclosed in U.S. Pat. Nos. 5,750,497 and 5,905,140 the disclosures of which are incorporated by reference hereinto.

As described below, IPs with synthetic C-peptides were constructed featuring a Gly residue (Examples 1 and 3). A *Saccharomyces cerevisiae* expression plasmid containing a DNA sequences of formula I was constructed by PCR and used to transform a *S. cerevisiae* host cell. The amount of insulin analog produced was measured as a percentage of the control level $Asp^{B28}$IP lacking mini C-peptide (Table 1 and 5). The novel C-peptides of the invention containing a Gly in the sequence $X_1$ of the mini C-peptide increased yields by up to 4-fold levels. In Example 4 production of human insulin precursors with a Gly in the C-peptide is described. The increase in yield is up to 2-fold (Table 6).

As described below in Example 2 for $Asp^{B28}$IP(Asp Gly Lys), the mini C-peptides of the invention result in a region of flexibility between B27 and A1 which all allow a proximity of A1 to B27 measured as the atomic distance between A1 (atom CA) and B27 (atom CG2) (e.g., less than 5 Å). Accordingly, the invention encompasses mini C-peptide constructs which induce the structural effects shown in Example 2 below.

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein.

EXAMPLES

General Procedures

All expressions plasmids are of the C-POT type, similar to those described in EP 171 142, which are characterized by containing the *Schizosaccharomyces pombe* triose phosphate isomerase gene (POT) for the purpose of plasmid selection and stabilization in *S. cerevisiae*. The plasmids furthermore contain the *S. cerevisiae* triose phosphate isomerase promoter and terminator. These sequences are similar to the corresponding sequences in plasmid pKFN1003 (described in WO 90/100075) as are all sequences except the sequence of the EcoRI-XbaI fragment encoding the fusion of the leader and insulin precursor. In order to express different fusion proteins, the EcoRI-XbaI fragment of pKFN1003 is simply replaced by an EcoRI- XbaI fragment encoding the leader insulin precursor or leader insulin precursor analog of interest. Such EcoRI-XbaI fragments may be synthesized using synthetic oligonucleotides and PCR according to standard techniques.

Yeast transformants were prepared by transformation of the host strain: S. cerevisiae strain MT663 (MATα/MATα pep4-3/pep4-3 HIS4/his4 tpi::LEU2/tpi::LEU2 Cir+). The yeast strain MT663 was deposited in the Deutsche Sammlung von Mikroorganismen und Zellkulturen in connection with filing WO 92/11378 and was given the deposit number DSM 6278.

MT663 was grown on YPGaL (1% Bacto yeast extract, 2% Bacto peptone, 2% galactose, 1% lactate) to an O.D. at 600 nm of 0.6. 100 ml of culture was harvested by centrifugation, washed with 10 ml of water, recentrifuged and resuspended in 10 ml of a solution containing 1.2 M sorbitol, 25 mM $Na_2EDTA$ pH=8.0 and 6.7 mg/ml dithiotreitol. The suspension was incubated at 30° C. for 15 minutes, centrifuged and the cells resuspended in 10 ml of a solution containing 1.2 M sorbitol, 10 mM $Na_2EDTA$, 0.1 M sodium citrate, pH 0 5.8, and 2 mg Novozym®234. The suspension was incubated at 30° C. for 30 minutes, the cells collected by centrifugation, washed in 10 ml of 1.2 M sorbitol and 10 ml of CAS (1.2 M sorbitol, 10 mM $CaCl_2$, 10 mM Tris HCl (Tris=Tris(hydroxymethyl)aminomethane) pH=7.5) and resuspended in 2 ml of CAS. For transformation, 1 ml of CAS-suspended cells was mixed with approx. 0.1 mg of plasmid DNA and left at room temperature for 15 minutes. 1 ml of (20% polyethylene glycol 4000, 10 mM $CaCl_2$, 10 mM Tris HCl, pH=7.5) was added and the mixture left for a further 30 minutes at room temperature. The mixture was centrifuged and the pellet resuspended in 0.1 ml of SOS (1.2 M sorbitol, 33% v/v YPD, 6.7 mM $CaCl_2$) and incubated at 30° C. for 2 hours. The suspension was then centrifuged and the pellet resuspended in 0.5 ml of 1.2 M sorbitol. Then, 6 ml of top agar (the SC medium of Sherman et al. (1982) Methods in Yeast Genetics, Cold Spring Harbor Laboratory) containing 1.2 M sorbitol plus 2.5% agar) at 52° C. was added and the suspension poured on top of plates containing the same agar-solidified, sorbitol containing medium.

S. cerevisiae stain MT663 transformed with expression plasmids were grown in YPD for 72 h at 30° C. Quantitation of the insulin-precursor yield in the culture supernatants was performed by reverse-phase HPLC analysis with human insulin as an external standard (Snel & Damgaard (1988) Proinsulin heterogenity in pigs. Horm. Metabol. Res. 20:476–488).

Example 1

Construction of Insulin Analog Precursors Comprising Synthetic C-peptides with a Glycine Residue Synthetic genes encoding fusion proteins consisting of $Asp^{B28}$IP associated with a leader sequence consisting of a pre-peptide (signal peptide) and a pro-peptide, were constructed using PCR under standard conditions (Sambrook et al. (1989) Molecular Cloning, Cold Spring Harbor Laboratory Press) and E.H.F. polymerase (Boehringer Mannheim GmbH, Sandhoefer Strasse 116, Mannheim, Germany). The resulting DNA fragments were isolated and digested with endonucleases and purified using the Gene Clean kit (Bio101 Inc., La Jolla, Calif., USA). Standard methods were used for DNA ligation and transformation of E. coli cells were performed by the $CaCl_2$ method (Sambrook et al. (1989) supra). Plasmids were purified from transformed E. coli cells using QIAGEN columns (QIAGEN, Hilden, Germany). Nucleotide sequences were determined using the ALF Pharmacia Biotech DNA sequencing system with purified double-stranded plasmid DNA as template. Oligonucleotide primers for PCR were obtained from DNA technology (Århus, Denmark).

Secretory expression of the $Asp^{B28}$IP in S. cerevisiae was performed using S. cerevisiae strain MT663 and the 2 μm based yeast expression vector CPOT (see FIG. 1) as described in Thim, L. et al. (1986) Proc. Natl. Acad. Sci. USA 83:6766–6770. The yeast expression vector contains the Schizosaccharomyces pombe triose phosphate isomerase gene (POT) for plasmid selection and stabilization in S. cerevisiae. Furthermore, the S. cerevisiae triose phosphate isomerase gene (TPI1) promoter and terminator are used for transcription initiation and termination of the recombinant gene encoding the leader-$Asp^{B28}$IP fusion protein. Secretion of the $Asp^{B28}$IP was facilitated by the α-factor leader, although a variety of known yeast leader sequences may be used.

As shown in FIG. 1, the pAK721 S. cerevisiae expression plasmid expressing the LA19 leader-EEAEAEAEPK(SEQ ID NO:2)-IP fusion protein was constructed based on the S. cerevisiae-E. coli shuttle POT plasmid (U.S. Pat. No. 5,871, 957). L-IP indicates the fusion protein expression cassette encoding the leader-IP fusion protein, TPI-PROMOTER is the S. cerevisiae TPI1 promoter and TPI-TERMINATOR is the S. cerevisiae TPI1 terminator; TPI-POMBE indicates the S. pombe POT gene used for selection in S. cerevisiae; ORIGIN indicates a S. cerevisiae origin of replication derived from the 2 μm plasmid; AMP-R indicates the β-lactamase gene conferring resistance toward ampicillin, facilitating selection in E. coli and ORIGIN-PBR322 indicates an E. coli origin of replication.

DNA encoding a number of fusion proteins of leader sequences and $Asp^{B28}$IP with different mini-C-peptides was generated by PCR using appropriate oligonucleotides as primers, as described below. Standard methods were used to subclone DNA fragments encoding the leader-$Asp^{B28}$IP fusion proteins into the CPOT expression vector in the following configuration: leader-Lys-Arg-spacer-$Asp^{B28}$IP, where Lys Arg is a potential dibasic endoprotease processing site. To optimize processing of the fusion protein by the S. cerevisiae Kex2 endoprotease, DNA encoding a spacer peptide, e.g. EEAEAEAPK (SEQ ID NO:3), was inserted between the DNA encoding the leader and the $Asp^{B28}$IP (Kjeldsen et al. (1996) Gene 170, 107–112.). However, the present of the spacer peptide is not mandatory. The mature $Asp^{B28}$IP was secreted as a single-chain N-terminally extended insulin precursor analogue with a synthetic mini C-peptide connecting $Lys^{B29}$ and $Gly^{A1}$. After purification of the $Asp^{B28}$ IP and proteolytic removal of the N-terminal extension and the synthetic mini C-peptide, a threonine amino acid residue ($Thr^{B30}$) may be added to $Lys^{B29}$ by enzyme-mediated transpeptidation, to generate $Asp^{B28}$ human insulin (Markussen, et al. (1987) in "Peptides 1986" (Theodoropoulos, D., Ed.), pp. 189–194, Walter de Gruyter & Co., Berlin.).

Development of synthetic mini C-peptides was performed by randomization of one or more codon(s) encoding the amino acids in the mini C-peptide. All synthetic mini C-peptides feature an enzymatic processing site (Lys) at the C-terminus which allows enzymatic removal of the synthetic mini C-peptide (U.S. Pat. No. 4,916,212, herein specifically incorporated by reference). Randomization was performed using doped oligonucleotides which introduced codon(s) variations at one or more positions of the synthetic mini C-peptides. Typically one of the two primers (oligonucleotides) used for PCR was doped. An example of an oligonucleotides pair used for PCR generation of leader-Asp$^{B28}$IP with randomized synthetic mini C-peptides used to generated synthetic mini C-peptides with the general formula: Xaa-Gly-Lys (XGK) are as follows:

```
Primer A: 5'TAAATCTATAACTACAAAAAACACATA-3'                      (SEQ ID NO: 13) and Primer B: 3'-CCAAAGAAGATGTGACTGTTCNNMCCCTTCCCATAGCAACTTGTTAC-   (SEQ ID NO: 14)
          AACATGAAGATAGACAAGAAACATGGTTAACCTTTTGATGACATTGATCAGATCTTT-
          GATTC 5', where N is A, C, G, or T and M is C or A.
```

PCR was typically performed as indicated below: 5 μl Primer A (20 pmol), 5 μl Primer B (20 pmol), 10 μl 10×PCR buffer, 8 μl dNTP mix, 0.75 μl E.H.F. enzyme, 1 μl pAK1150 plasmid as template (approximately 0.2 μg DNA) (SEQ ID NO:3), and 70.25 μl distilled water.

Typically between 10 and 15 cycles were performed, one cycle typically was 94° C. for 45 sec.; 55° C. for 1 min; 72° C. for 1.5 min. The PCR mixture was subsequently loaded onto an 2% agarose gel and electrophoresis was performed using standard techniques. The resulting DNA fragment was cut out of the agarose gel and isolated by the Gene Clean kit.

FIG. 2 shows the sequence of pAK1150 DNA used as template for PCR and inferred amino acids of the encoded fusion protein (α-factor-leader-EEAEAEAPK(SEQ ID NO:3)-Asp$^{B28}$IP of pAK1150 (SEQ ID NO:4 and 5). The pAK1150 plasmid is similar to pAK721 shown in FIG. 1. The α-factor-leader's C-terminus was modified to introduce a Nco I restriction endonuclease site, which changes the inferred amino acid sequences linked to LysArg from SerLeuAsp to SerMetAla. Moreover, the encoded Asp$^{B28}$IP does not feature a mini C-peptide but Lys$^{B29}$ is directly connected to Gly$^{A1}$.

The purified PCR DNA fragment was dissolved in water and restriction endonucleases buffer and digested with suitable restriction endonucleases (e.g. Bgl II and Xba I) according to standard techniques. The BglII-XbaI DNA fragments were subjected to agarose electrophoresis and purified using The Gene Clean Kit.

The expression plasmid pAK1150 or a similar plasmid of the CPOT type (see FIG. 1) was digested with the restriction endonucleases Bgl II and Xba I and the vector fragment of 10765 nucleotide basepairs isolated using The Gene Clean Kit.

The two digested and isolated DNA fragments (the vector fragment and the PCR fragment) were ligated together using T4 DNA ligase and standard conditions. The ligation mix was subsequently transformed into a competent E. coli strain (R−, M+) followed by selection with ampicillin resistance. Plasmids from the resulting E. coli's were isolated using QIAGEN columns.

The plasmids were subsequently used for transformation of a suitable S. cerevisiae strain MT663 (MATα/MATα pep4-3/pep4-3 HIS4/his4 tpi::LEU2/tpi::LEU2 Cir$^+$). Individual transformed S. cerevisiae clones were grown in liquid culture, and the quantity of ASP$^{B28}$IP secreted to the culture supernatants were determined by RP-HPLC. The DNA sequence encoding the synthetic mini C-peptide of the expression plasmids from S. cerevisiae clones secreting increased quantity of the Asp$^{B28}$IP were then determined. Subsequently, the identified synthetic mini C-peptide sequence might be subjected to another round of randomization optimization.

An example on a DNA sequence encoding a leader-Asp$^{B28}$IP(AspGlyLys) fusion protein featuring a synthetic mini C-peptide (AspGlyLys) resulting from the randomized optimization process described are shown in FIG. 3 (SEQ ID NO:6 and 7).

Table 1 shows the insulin analogue precursors generated by the above method and production yield expressed as a percent of the control. Fermentation was at 30° C. for 72 h in 5 ml YPD. Yield of the insulin precursor analogs was determined by RP-HPLC of the culture supernatant, and is expressed relative to the yield of insulin precursor of a control strain. In the table, "α*" indicates an α-factor leader in which the C-terminus up to the LysArg has been modified from SLD (SerLeuAsp) to SMA (SerMetAla) and "ex4" is an N-terminal extension peptide with the amino acid sequence EEAEAEAPK (SEQ ID NO:3).

TABLE 1

| Leader-N-terminal extension | Precursor | C-peptide | Yield* | SEQ ID |
|---|---|---|---|---|
| α*-ex4 | Asp$^{B28}$IP | — | 100 | |
| α*-ex4 | Asp$^{B28}$IP | GluGluGlyLys | 245 | SEQ ID NO:1 |
| α*-ex4 | Asp$^{B28}$IP | GluGlyLys | 350 | |
| α*-ex4 | Asp$^{B28}$IP | SerGlyLys | 294 | |
| α*-ex4 | Asp$^{B28}$IP | AsnGlyLys | 341 | |
| α*-ex4 | Asp$^{B28}$IP | ThrGlyLys | 258 | |
| α*-ex4 | Asp$^{B28}$IP | AspGlyLys | 428 | |
| α*-ex4 | Asp$^{B28}$IP | MetGlyLys | 225 | |
| α*-ex4 | Asp$^{B28}$IP | AlaGlyLys | 243 | |
| α*-ex4 | Asp$^{B28}$IP | HisGlyLys | 225 | |
| α*-ex4 | Asp$^{B28}$IP | TyrGlyLys | 214 | |

Example 2

Structure Determination of Asp$^{B28}$IP(AspGlyLys) in Aqueous Solution by NMR Spectroscopy NMR spectroscopy. Samples for NMR were prepared by dissolving the lyophilized protein powder in 10/90 D$_2$O/H$_2$O with a 10 mM phosphate buffer and adjusting the pH as desired by addition of small volumes of 1 M DCl or NaOD. All pH meter readings are without correction for isotope effects. Samples of Asp$^{B28}$IP(AspGlyLys) for NMR were prepared at concentrations ranging from 25 μM to 1 mM at pH 8.0. Two-dimensional $^1$H-$^1$H NMR spectra of 1 mM samples, DQF-COSY (Piantini et al. (1982) J. Am. Chem. Soc. 104:6800–6801, Rance et al. (1983) Biochem. Biophys. Res. Commun. 117:479–485), TOCSY (Braunschweiler et al. (1983) J. Magn. Reson. 53:521–528, Bax et al. (1985) J. Magn. Reson. 65:355–360) and NOESY (Jeener et al. (1979) J. Chem. Phys. 71:4546–4553) were recorded at 600 MHz on a Varian Unity Inova NMR spectrometer equipped with a $^1$H/$^{13}$C/$^{15}$N triple resonance probe with a self-shielded triple-axis gradient coil using standard pulse sequences from the Varian user library. The operating temperature was set to 27° C. For each phase sensitive two-dimensional NMR spectrum 512 $t_1$ increments were acquired each with 2048 or 4096 real data points according to the TPPI-States method (Marion et al. (1989) J. Magn. Reson. 85:393–399). Spectral widths of 6983 Hz in both dimensions were used, with the carrier placed exactly on the water resonance which was attenuated by using either saturation between scans for 1.5 seconds or selective excitation by a gradient-tailored excitation pulse sequence (WATERGATE, Piotto et al. (1992) J. Biomol. NMR 2:661–665). DQFCOSY spectra were recorded using a gradient enhanced version applying magic-angle gradients (Mattiello et al. (1996) J. Am. Chem. Soc. 118:3253–3261). For TOCSY spectra mixing times between 30 and 80 ms were used and for NOESY mixing times between 50 and 200 ms.

The processing of the two-dimensional NMR spectra was performed using the software package Xwinnmr (version 2.5, NMR processing software from Bruker Analytische Messtechnik GmbH, D-76275 Ettlingen, Germany). Each dimension was processed with shifted sine-bell apodization and zero-filling performed once in each dimension. Baseline corrections were applied if necessary using Xwinnmr standard procedures. The spectral assignment, cross peak integration, sequence specific assignment, stereo specific assignment, and all other bookkeeping were performed using the program PRONTO (PRONTO Software Development and Distribution, Copenhagen Denmark) (Kjær et al. (1991) *NATO ASI Series* (Hoch, J. C., Redfield C., & Poulsen, F. M., Eds.) Plenum, New York). Chemical shifts are measured in ppm and the water resonance set to 4.75 ppm.

Structure calculations. Distance restraints for the subsequent structure calculation were obtained from integrated NOESY cross peaks classified as either weak, medium or strong corresponding to upper distance restraints of 5.5, 3.3, and 2.7 Å, respectively. For distance restraints involving methyl groups, an additional 0.5 Å was added to the upper limit (Wagner et al. (1985) J. Mol. Biol. 196:611–639). Structure calculations were performed using the hybrid method combining distance geometry (Crippen et al. (1988) *Distance Geometry and Molecular Conformation,* Research Studies Press, Taunton, Somerset, England; Kuszewski et al. (1992) J. Biomol NMR 2:33–56) and simulated annealing based on the ideas of Nilges et al. (1988) FEBS Lett. 229:317–324 using X-PLOR 3.0 (Brünger (1992) *X-PLOR Version 3.1: A System for X-ray Crystallography and NMR,* Yale University Press, New Haven) according to the examples given by the X-PLOR manual (dg_sub_embed.inp, dgsa.inp, refine.inp). Residue numbers are derived from standard insulin residue numbering, residues in the B-chain are numbered B1–29, residues in the C-peptide (e.g. AsplyLys) are numbered C1–C3 and residues in the A-chain are numbered A1–A21.

Spectral assignment of the NMR spectra followed for most resonances the standard sequential assignment procedure described by Wüthrich (1986 NMR of Proteins and Nucleic Acids, Wiley, N.Y.). The standard assignment procedure fails when the amid proton of a particular amino acid residue exchanges to rapidly with protons in the water. At pH 8.0 this occurs for several amino acid residues, however, comparison with earlier mutant insulin NMR spectral assignments and identification of neighboring (in space) amino acid residues through NOEs allow an almost total spectral assignment. Analysis of the NOESY spectra showed that several amino acid residues had a NOE network to the surrounding residues similar to what has previously been determined for other insulin molecules, i.e., human insulin $His^{B16}$ mutant (Ludvigsen et al. (1994) Biochemistry 33:7998–8006) and these similar connections are found for residues B1–B10, B13–B14, B17–B24 and A4–A21. Additionally the dihedral angle restraints for the above listed residues were adopted from those used previously (Ludvigsen et al. (1994) supra).

Figure 4:
FIG. 4 shows the solution structures of $Asp^{B28}IP$ (AspGlyLys) as backbone lines of ensemble of 20 converged structures.

Several amino acids in particular B27–B29, C1–C3, A1–A3 have cross peaks patterns which are consistent with peptide chains that are less well ordered than commonly well-defined secondary structural elements. Thus additional NOEs were converted into distance restraints without any further classification than upper limits of 5.5 Å or 6.0 Å if a methyl group were included. An ensemble of 20 converged structures (FIG. 4) was calculated and the relevant parameters listed in Table 2 for the converged structures. Each NOE here identical to a distance restraint is only counted once even though it might occur several times in the NOESY spectrum. Ramachandran plot quality assessment is standard quality parameters to evaluate local geometry quality. In general the described quality parameters are comparable to 2.5 Å resolution of X-ray based protein structures (Laskowski et al. (1996) J. Biomol. NMR 8:477–486).

TABLE 2

| Structural quality assessment | $Asp^{B28}IP(AspGlyLys)$ |
|---|---|
| Number of NOEs | |
| Total | 913 |
| Intra | 454 |
| short range | 297 |
| (within 5 residue positions away but not intra NOEs) | |
| Long range | 162 |
| (more than 5 residue positions away) | |
| Violations of NOEs > 0.4 Å | 0 |
| (average for 20 structures) | |
| RMS of NOE violations | 0.020(±0.002)Å |
| RMS of dihedral angle restraints | 0.32(±0.12)° |
| Deviations from ideal geometry | |
| Impropers | 0.37(±0.05)° |
| Angles | 0.43(±0.03)° |
| Bonds | 0.0034(±0.0002)Å |
| Ramachandran Plot | |
| (Procheck, Laskowski et al, 1996) | |
| Favoured regions | 76.1% |
| additional allowed regions | 20.8% |
| generously allowed regions | 2.2% |
| disallowed regions | 1.0% |

Description of the Calculated Structure

Figure 5:
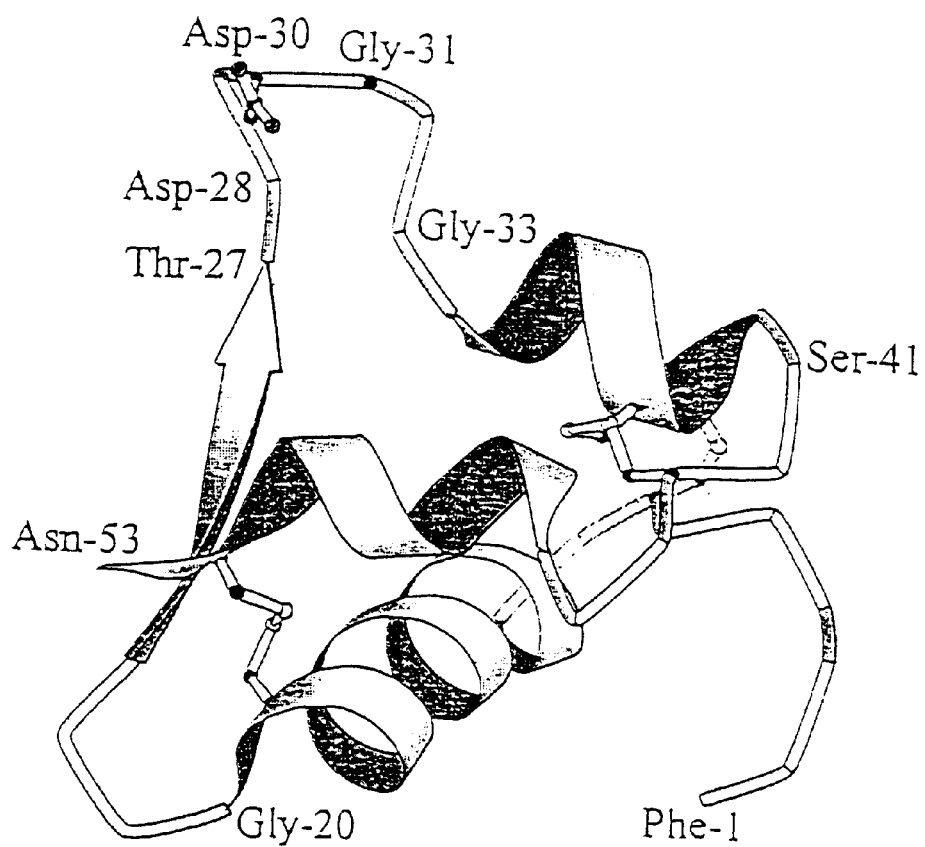
FIG. 5 shows a ribbon presentation of $Asp^{B28}IP$ (AspGlyLys). The figure is produced using MOLSCRIPT (Kraulis (1991) J. Appl. Crystallog. 24:946–950). Amino acid residue annotation is derived as follows: B1–B29 (B chain) are numbered 1–29, residues C1–C3 (C chain) are numbered 30–32, and residues A1–A21 (A chain) are numbered 33–53.
Figure 6:
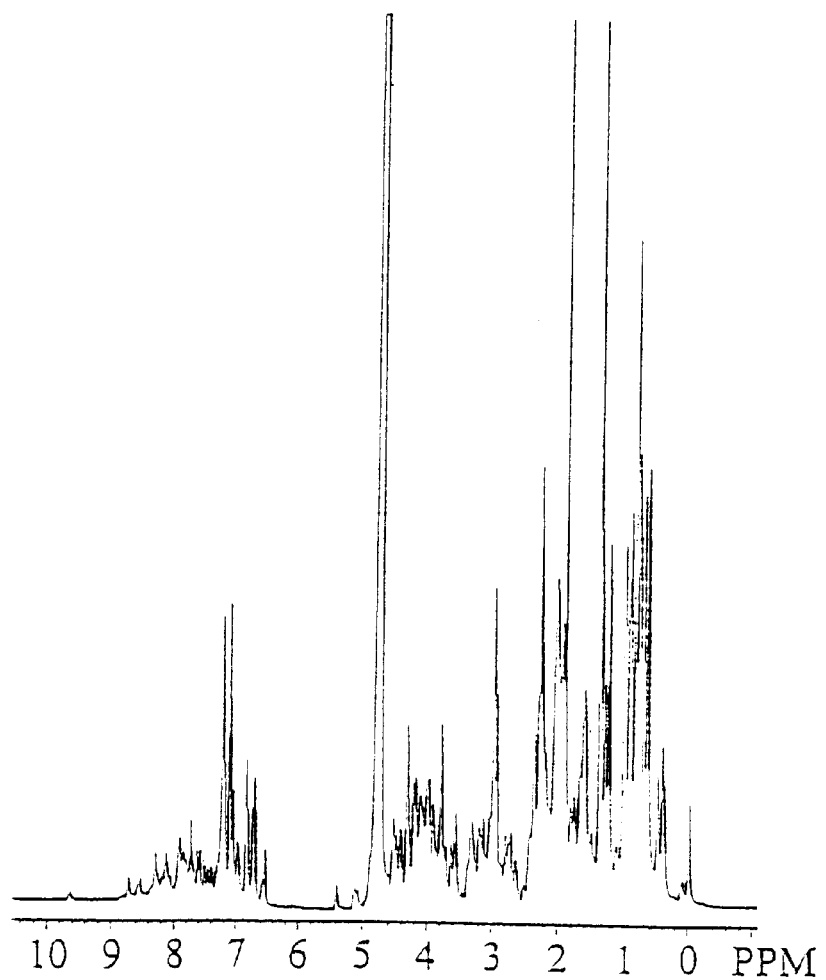
FIG. 6 is the ID proton NMR spectrum for $Asp^{B28}IP$(Asp Gly Lys) recorded at 27° C. at 1.0 mM concentration in 10%/90% $D_2O/H_2O$ with 10 mM phosphate buffer at pH 8.0.

A representative structure resembling the average of the ensemble is displayed in FIG. 5. $Asp^{B28}IP(AspGlyLys)$ is structurally similar to the native insulin structure for regions comprising residues B1–B10, B14–B23, A4–A21. The differences are mostly pronounced for regions in the vicinity of the connecting peptide in positions B26–B29, C1–C3, A1–A3 and less pronounced for residues B11–B13. The structure of $Asp^{B28}IP(AspGlyLys)$ near the C-peptide is strikingly different from the native like structure in solution (Ludvigsen (1994) supra) and $Asp^{B28}IP(AlaAlaLys)$ structure in the crystal phase (Whittingham et al. (1998) Biochemistry 37:11516–11523). The connecting peptide of $Asp^{B28}$ IP(AspGlyLys) is poorly determined in terms of accuracy, but a few structural restraints obtained from the NOESY spectra (NOEs between $Thr^{B27}$ and $Gly^{C2}$ and between $Thr^{B27}$ and $Gly^{A1}$) clearly indicate important structural arrangements of the C-peptide. The relative intense NOEs between $Thr^{B27}$ (methyl group HG2) and $Gly^{C2}$ (atom HA) and between $Thr^{B27}$ (methyl group HG2) and $Gly^{A1}$ (atom HA) in a flexible region shows that these proton pairs are close in space (<5 Å). The tight arrangement of $Thr^{B27}$, $Gly^{C2}$ and $Gly^{A1}$ defined as the atomic distance between B27 (CG2) and A1 (CA) is less than 5 Å, not seen previously in any single chain insulin molecule shows that the C-peptide accommodates this structural arrangement and in fact the C-peptide can do this in several ways which appears to be a prerequisite for the C-peptide. However, it is clear that the presence of Glycine in the connecting peptide allows more flexibility in the connecting peptide and subsequently less structural constraints are imposed on the neighboring amino acids in their quest to accommodate an optimal packing with the remainder of the insulin molecule. Secondly the arrangement of $Asp^{B28}$, $Lys^{B29}$, $Asp^{C1}$ and $Lys^{C3}$ charged side-chains creates a highly polar surface compared to other connecting peptides.

Under the conditions used for NMR both the spectra $Asp^{B28}IP(AspGlyLys)$ are influenced by some degree of self-association but the exchange between monomer and dimer is on the timescale of NMR only observed here as an average between the two states. Below concentrations of 0.2 mM the degree of self-association does not change as seen by NMR at even lower concentrations (at least until 25 $\mu$M). Table 3 provides the NMR spectral assignments for $Asp^{B28}IP(AspGlyLys)$ and Table 4 provides the atomic coordinates of $Asp^{B28}IP(AspGlyLys)$ in PDB format. The structure selected to represent the ensemble (FIG. 5 and Table 4 atomic coordinates) has 84.8% residues in "favored" regions and 15.2% in "additionally allowed" regions of the ramachandran plot as described in Table 2.

Table 3 shows chemical shifts of $Asp^{B28}IP(AspGlyLys)$ at 27° Celcius obtained at 600 MHz, pH 8 in 10%/90% $D_2O/H_2O$ with 10 mM phosphate buffer. Chemical shifts are referenced by setting the residual water signal to 4.75 ppm. N/A means no assignment. $Asp^{B28}IP(AspGlyLys)$ assignments (1–29=B1–B29; 30–32=C1–C3 and 33–53=A1–A21):

TABLE 3

| Spin system | HN | HA | Other: |
|---|---|---|---|
| Phe-1 | | 4.52 | HB#a: N/A, HB#b: 2.992, HD#: 7.087, HE#: 7.203, HZ: 7.145 |
| Val-2 | 7.70 | 3.99 | HB: 1.912, HG#a: 0.797, HG#b: N/A |
| Asn-3 | | 4.50 | HB#a: 2.989, HB#b: 2.321, HD2#a: 7.372, HD2#b: 6.920 |
| Glu-4 | | 4.38 | HB#a: 1.999, HB#b: 2.103 |
| His-5 | | 4.31 | HB#a: 3.314, HB#b: 2.978, HD2: 6.798, HE1: 7.595 |
| Leu-6 | | 4.44 | HB#a: 1.648, HB#b: N/A, HG: 1.503, HD#a: 0.755, HD#b: 0.662 |

TABLE 3-continued

| Spin system | HN | HA | Other: |
|---|---|---|---|
| Cys-7 | 8.28 | 4.87 | HB#a: 2.925, HB#b: 3.143 |
| Gly-8 | | 3.94, 3.76 | |
| Ser-9 | | 4.05 | HB# 3.812 |
| His-10 | 8.55 | 4.38 | HB#a: 3.124, HB#b: 3.282, HD2: 7.081, HE1: 7.708 |
| Leu-11 | 6.93 | 3.85 | HB#a: 1.749, HB#b: 1.175, HG: 1.222, HD#a: 0.602, HD#b: 0.722 |
| Val-12 | 7.02 | 3.17 | HB: 2.031, HG#a: 0.970, HG#b: N/A |
| Glu-13 | 7.84 | 3.97 | HB#a: 2.025, HG#a: 2.222, HG#b: 2.383 |
| Ala-14 | 7.55 | 3.94 | HB#: 1.253 |
| Leu-15 | 7.91 | 3.59 | HB#a: 0.905, HB#b: 0.067, HG: 1.075, HD#a: 0.377, HD#b: −0.051 |
| Tyr-16 | 8.10 | 4.30 | HB#a: 3.064, HD#: 7.193, HE#: 6.771 |
| Leu-17 | 7.66 | 4.02 | HB#a: N/A, HB#b: 1.844, HG: 1.712, HD#a: 0.892, HD#b: 0.872 |
| Val-18 | 8.27 | 3.68 | HB: 1.882, HG#a: 0.945, HG#b: 0.792 |
| Cys-19 | 8.69 | 4.76 | HB#a: 2.759, HB#b: 3.254 |
| Gly-20 | 7.78 | 3.90, 3.76 | |
| Arg-22 | 8.03 | 4.08 | HB#a: 1.801, HB#b: 1.845, HG#a: 2.041, HG#b: 2.088, HD#a: 3.352, HD#b: 3.280 |
| Gly-23 | 7.23 | 4.07, 3.67 | |
| Phe-24 | 7.37 | 5.37 | HB#a: 2.857, HB#b: 3.013, HD#: 6.502, HE#: 6.688, HZ: 6.944 |
| Phe-25 | 8.51 | 4.87 | HB#a: 3.151, HB#b: 3.321, HD#: 7.162, HE#: 7.073 |
| Tyr-26 | 8.17 | 4.69 | HB#a: 2.920, HB#b: 3.168, HD#: 7.029, HE#: 6.662 |
| Thr-27 | 7.80 | 5.06 | HB: 3.965, HG2#: 1.198 |
| Asp-28 | 8.43 | 4.50 | HB#a: 2.764, HB#b: 2.660 |
| Lys-29 | | | |
| Asp-30 | 8.06 | 4.76 | HB#a: 2.615, HB#b: 2.821 |
| Gly-31 | 8.15 | 4.14, 3.58 | |
| Lys-32 | | | |
| Gly-33 | | 4.03, 4.87 | |
| Ile-34 | 8.16 | 3.78 | HB: N/A, HG1#a: 0.730, HG1#b: 0.885, HG2#: 0.722, HD#: 0.345 |
| Val-35 | 8.08 | 3.54 | HB: 1.966, HB: N/A, HG#a: 0.862, HG#b: 0.957 |
| Glu-36 | 8.23 | 4.11 | HB#a: 2.094, HG#a: 2.249 |
| Gln-37 | 7.79 | 4.09 | HB#: N/A, HG#: N/A |
| Cys-38 | 8.11 | 5.04 | HB#a: 3.273, HB#b: 2.695 |
| Cys-39 | 8.33 | 4.86 | HB#a: 3.732, HB#b: 3.275 |
| Thr-40 | | 4.06 | HB: 4.402, HB2#: 1.188 |
| Ser-41 | 7.23 | 4.62 | HB#a: 3.732, HB#b: 3.874 |
| Ile-42 | 7.74 | 4.18 | HB: 1.488, HG1#a: 1.038, HG2#: 0.604, HD#: 0.446 |
| Cys-43 | 9.61 | 4.95 | HB#a: 3.125 |
| Ser-44 | 8.52 | 4.58 | HB#a: 4.084, HB#b: 3.930 |
| Leu-45 | | 3.88 | HB#a: N/A, HB#b: 1.452, HG: 1.543, HD#a: 0.812, HD#b: 0.750 |
| Tyr-46 | 7.58 | 4.28 | HB#a: 2.956, HD#: 7.074, HE#: 6.806 |
| Gln-47 | 7.43 | 3.95 | HB#a: 2.287, HB#b: 1.983, HG#a: 2.382, HG#b: 2.140 |
| Leu-48 | 7.70 | 3.99 | HB#a: 1.905, HB#b: 1.329, HG: 1.658, HD#a: 0.666, HD#b: 0.614 |
| Glu-49 | 7.82 | 4.15 | HB#a: N/A, HB#b: 1.946, HG#a: 2.307, HG#b: 2.171 |
| Asn-50 | 7.27 | 4.44 | HB#a: 2.716, HB#b: 2.592 |
| Tyr-51 | 7.88 | 3.94 | HB#a: 3.534, HB#b: 2.573, HD#: 7.192, HE#: 6.682 |
| Cys-52 | 7.03 | 5.10 | HB#a: 2.711, HB#b: 3.231 |
| Asn-53 | 7.88 | 4.46 | HB#a: 2.475, HB#b: 2.683, HD2#a: 7.480, HD2#b: 6.549 |

TABLE 4

Atomic coordinates of Asp$^{28}$IP(AspGlyLys) in PDB format

| ATOM | 1 | CA | PHE | 1 | 5.563 | −10.343 | 1.925 | 1.00 | 0.00 |
|---|---|---|---|---|---|---|---|---|---|
| ATOM | 2 | HA | PHE | 1 | 5.191 | −11.286 | 1.550 | 1.00 | 0.00 |
| ATOM | 3 | CB | PHE | 1 | 4.581 | −9.224 | 1.558 | 1.00 | 0.00 |
| ATOM | 4 | HB1 | PHE | 1 | 5.131 | −8.325 | 1.323 | 1.00 | 0.00 |
| ATOM | 5 | HB2 | PHE | 1 | 3.923 | −9.037 | 2.393 | 1.00 | 0.00 |
| ATOM | 6 | CG | PHE | 1 | 3.765 | −9.641 | 0.357 | 1.00 | 0.00 |
| ATOM | 7 | CD1 | PHE | 1 | 3.789 | −8.866 | −0.809 | 1.00 | 0.00 |
| ATOM | 8 | HD1 | PHE | 1 | 4.392 | −7.970 | −0.851 | 1.00 | 0.00 |
| ATOM | 9 | CD2 | PHE | 1 | 2.985 | −10.800 | 0.410 | 1.00 | 0.00 |
| ATOM | 10 | HD2 | PHE | 1 | 2.968 | −11.397 | 1.311 | 1.00 | 0.00 |
| ATOM | 11 | CE1 | PHE | 1 | 3.033 | −9.253 | −1.921 | 1.00 | 0.00 |
| ATOM | 12 | HE1 | PHE | 1 | 3.052 | −8.657 | −2.822 | 1.00 | 0.00 |
| ATOM | 13 | CE2 | PHE | 1 | 2.229 | −11.187 | −0.701 | 1.00 | 0.00 |
| ATOM | 14 | HE2 | PHE | 1 | 1.627 | −12.083 | −0.658 | 1.00 | 0.00 |
| ATOM | 15 | CZ | PHE | 1 | 2.252 | −10.414 | −1.867 | 1.00 | 0.00 |
| ATOM | 16 | HZ | PHE | 1 | 1.670 | −10.713 | −2.726 | 1.00 | 0.00 |
| ATOM | 17 | C | PHE | 1 | 6.925 | −10.049 | 1.295 | 1.00 | 0.00 |
| ATOM | 18 | O | PHE | 1 | 7.945 | −10.088 | 1.957 | 1.00 | 0.00 |
| ATOM | 19 | N | PHE | 1 | 5.702 | −10.416 | 3.406 | 1.00 | 0.00 |
| ATOM | 20 | HT1 | PHE | 1 | 6.005 | −9.491 | 3.772 | 1.00 | 0.00 |
| ATOM | 21 | HT2 | PHE | 1 | 6.412 | −11.136 | 3.653 | 1.00 | 0.00 |
| ATOM | 22 | HT3 | PHE | 1 | 4.787 | −10.672 | 3.829 | 1.00 | 0.00 |
| ATOM | 23 | N | VAL | 2 | 6.943 | −9.757 | 0.020 | 1.00 | 0.00 |
| ATOM | 24 | HN | VAL | 2 | 6.105 | −9.735 | −0.486 | 1.00 | 0.00 |
| ATOM | 25 | CA | VAL | 2 | 8.231 | −9.458 | −0.667 | 1.00 | 0.00 |
| ATOM | 26 | HA | VAL | 2 | 9.024 | −10.032 | −0.210 | 1.00 | 0.00 |
| ATOM | 27 | CB | VAL | 2 | 8.122 | −9.830 | −2.148 | 1.00 | 0.00 |
| ATOM | 28 | HB | VAL | 2 | 7.420 | −9.167 | −2.633 | 1.00 | 0.00 |
| ATOM | 29 | CG1 | VAL | 2 | 9.494 | −9.691 | −2.810 | 1.00 | 0.00 |
| ATOM | 30 | HG11 | VAL | 2 | 9.807 | −8.658 | −2.773 | 1.00 | 0.00 |
| ATOM | 31 | HG12 | VAL | 2 | 9.431 | −10.012 | −3.840 | 1.00 | 0.00 |
| ATOM | 32 | HG13 | VAL | 2 | 10.211 | −10.304 | −2.285 | 1.00 | 0.00 |
| ATOM | 33 | CG2 | VAL | 2 | 7.638 | −11.275 | −2.277 | 1.00 | 0.00 |
| ATOM | 34 | HG21 | VAL | 2 | 6.763 | −11.417 | −1.660 | 1.00 | 0.00 |
| ATOM | 35 | HG22 | VAL | 2 | 8.418 | −11.948 | −1.954 | 1.00 | 0.00 |
| ATOM | 36 | HG23 | VAL | 2 | 7.389 | −11.481 | −3.308 | 1.00 | 0.00 |
| ATOM | 37 | C | VAL | 2 | 8.542 | −7.967 | −0.542 | 1.00 | 0.00 |
| ATOM | 38 | O | VAL | 2 | 7.869 | −7.135 | −1.120 | 1.00 | 0.00 |
| ATOM | 39 | N | ASN | 3 | 9.562 | −7.624 | 0.206 | 1.00 | 0.00 |
| ATOM | 40 | HN | ASN | 3 | 10.089 | −8.316 | 0.658 | 1.00 | 0.00 |
| ATOM | 41 | CA | ASN | 3 | 9.926 | −6.186 | 0.370 | 1.00 | 0.00 |
| ATOM | 42 | HA | ASN | 3 | 9.083 | −5.644 | 0.771 | 1.00 | 0.00 |
| ATOM | 43 | CB | ASN | 3 | 11.112 | −6.067 | 1.329 | 1.00 | 0.00 |
| ATOM | 44 | HB1 | ASN | 3 | 11.492 | −5.057 | 1.310 | 1.00 | 0.00 |
| ATOM | 45 | HB2 | ASN | 3 | 11.892 | −6.752 | 1.025 | 1.00 | 0.00 |
| ATOM | 46 | CG | ASN | 3 | 10.654 | −6.411 | 2.748 | 1.00 | 0.00 |
| ATOM | 47 | OD1 | ASN | 3 | 9.911 | −7.350 | 2.949 | 1.00 | 0.00 |
| ATOM | 48 | ND2 | ASN | 3 | 11.070 | −5.683 | 3.748 | 1.00 | 0.00 |
| ATOM | 49 | HD21 | ASN | 3 | 11.669 | −4.925 | 3.586 | 1.00 | 0.00 |
| ATOM | 50 | HD22 | ASN | 3 | 10.781 | −5.894 | 4.660 | 1.00 | 0.00 |
| ATOM | 51 | C | ASN | 3 | 10.308 | −5.602 | −0.991 | 1.00 | 0.00 |
| ATOM | 52 | O | ASN | 3 | 11.414 | −5.782 | −1.466 | 1.00 | 0.00 |
| ATOM | 53 | N | GLN | 4 | 9.395 | −4.909 | −1.623 | 1.00 | 0.00 |
| ATOM | 54 | HN | GLN | 4 | 8.512 | −4.784 | −1.217 | 1.00 | 0.00 |
| ATOM | 55 | CA | GLN | 4 | 9.688 | −4.313 | −2.957 | 1.00 | 0.00 |
| ATOM | 56 | HA | GLN | 4 | 10.705 | −3.950 | −2.973 | 1.00 | 0.00 |
| ATOM | 57 | CB | GLN | 4 | 9.509 | −5.381 | −4.038 | 1.00 | 0.00 |
| ATOM | 58 | HB1 | GLN | 4 | 8.468 | −5.655 | −4.103 | 1.00 | 0.00 |
| ATOM | 59 | HB2 | GLN | 4 | 10.096 | −6.249 | −3.779 | 1.00 | 0.00 |
| ATOM | 60 | CG | GLN | 4 | 9.977 | −4.834 | −5.389 | 1.00 | 0.00 |
| ATOM | 61 | HG1 | GLN | 4 | 10.940 | −4.358 | −5.272 | 1.00 | 0.00 |
| ATOM | 62 | HG2 | GLN | 4 | 9.260 | −4.114 | −5.754 | 1.00 | 0.00 |
| ATOM | 63 | CD | GLN | 4 | 10.101 | −5.986 | −6.387 | 1.00 | 0.00 |
| ATOM | 64 | OE1 | GLN | 4 | 9.108 | −6.515 | −6.849 | 1.00 | 0.00 |
| ATOM | 65 | NE2 | GLN | 4 | 11.285 | −6.401 | −6.744 | 1.00 | 0.00 |
| ATOM | 66 | HE21 | GLN | 4 | 12.086 | −5.975 | −6.373 | 1.00 | 0.00 |
| ATOM | 67 | HE22 | GLN | 4 | 11.374 | −7.140 | −7.381 | 1.00 | 0.00 |
| ATOM | 68 | C | GLN | 4 | 8.728 | −3.150 | −3.217 | 1.00 | 0.00 |
| ATOM | 69 | O | GLN | 4 | 7.710 | −3.016 | −2.564 | 1.00 | 0.00 |
| ATOM | 70 | N | HIS | 5 | 9.053 | −2.304 | −4.160 | 1.00 | 0.00 |
| ATOM | 71 | HN | HIS | 5 | 9.883 | −2.434 | −4.665 | 1.00 | 0.00 |
| ATOM | 72 | CA | HIS | 5 | 8.175 | −1.136 | −4.467 | 1.00 | 0.00 |
| ATOM | 73 | HA | HIS | 5 | 7.882 | −0.660 | −3.543 | 1.00 | 0.00 |
| ATOM | 74 | CB | HIS | 5 | 8.952 | −0.133 | −5.327 | 1.00 | 0.00 |
| ATOM | 75 | HB1 | HIS | 5 | 8.355 | 0.752 | −5.481 | 1.00 | 0.00 |
| ATOM | 76 | HB2 | HIS | 5 | 9.190 | −0.582 | −6.281 | 1.00 | 0.00 |
| ATOM | 77 | CG | HIS | 5 | 10.221 | 0.235 | −4.607 | 1.00 | 0.00 |

TABLE 4-continued

Atomic coordinates of Asp²⁸IP(AspGlyLys) in PDB format

| ATOM | 78 | ND1 | HIS | 5 | 10.323 | 1.365 | −3.815 | 1.00 | 0.00 |
|---|---|---|---|---|---|---|---|---|---|
| ATOM | 79 | HD1 | HIS | 5 | 9.636 | 2.051 | −3.698 | 1.00 | 0.00 |
| ATOM | 80 | CD2 | HIS | 5 | 11.431 | −0.401 | −4.505 | 1.00 | 0.00 |
| ATOM | 81 | HD2 | HIS | 5 | 11.691 | −1.314 | −5.005 | 1.00 | 0.00 |
| ATOM | 82 | CE1 | HIS | 5 | 11.553 | 1.366 | −3.267 | 1.00 | 0.00 |
| ATOM | 83 | HE1 | HIS | 5 | 11.906 | 2.105 | −2.570 | 1.00 | 0.00 |
| ATOM | 84 | NE2 | HIS | 5 | 12.270 | 0.312 | −3.659 | 1.00 | 0.00 |
| ATOM | 85 | C | HIS | 5 | 6.922 | −1.614 | −5.206 | 1.00 | 0.00 |
| ATOM | 86 | O | HIS | 5 | 6.951 | −2.590 | −5.931 | 1.00 | 0.00 |
| ATOM | 87 | N | LEU | 6 | 5.819 | −0.941 | −5.005 | 1.00 | 0.00 |
| ATOM | 88 | HN | LEU | 6 | 5.824 | −0.170 | −4.403 | 1.00 | 0.00 |
| ATOM | 89 | CA | LEU | 6 | 4.546 | −1.353 | −5.667 | 1.00 | 0.00 |
| ATOM | 90 | HA | LEU | 6 | 4.633 | −2.370 | −6.017 | 1.00 | 0.00 |
| ATOM | 91 | CB | LEU | 6 | 3.398 | −1.259 | −4.658 | 1.00 | 0.00 |
| ATOM | 92 | HB1 | LEU | 6 | 2.510 | −1.694 | −5.086 | 1.00 | 0.00 |
| ATOM | 93 | HB2 | LEU | 6 | 3.213 | −0.219 | −4.425 | 1.00 | 0.00 |
| ATOM | 94 | CG | LEU | 6 | 3.766 | −2.012 | −3.378 | 1.00 | 0.00 |
| ATOM | 95 | HG | LEU | 6 | 4.726 | −1.669 | −3.022 | 1.00 | 0.00 |
| ATOM | 96 | CD1 | LEU | 6 | 2.702 | −1.755 | −2.306 | 1.00 | 0.00 |
| ATOM | 97 | HD11 | LEU | 6 | 2.518 | −2.664 | −1.752 | 1.00 | 0.00 |
| ATOM | 98 | HD12 | LEU | 6 | 1.786 | −1.429 | −2.775 | 1.00 | 0.00 |
| ATOM | 99 | HD13 | LEU | 6 | 3.052 | −0.989 | −1.629 | 1.00 | 0.00 |
| ATOM | 100 | CD2 | LEU | 6 | 3.837 | −3.510 | −3.681 | 1.00 | 0.00 |
| ATOM | 101 | HD21 | LEU | 6 | 4.620 | −3.694 | −4.401 | 1.00 | 0.00 |
| ATOM | 102 | HD22 | LEU | 6 | 2.891 | −3.840 | −4.083 | 1.00 | 0.00 |
| ATOM | 103 | HD23 | LEU | 6 | 4.050 | −4.052 | −2.771 | 1.00 | 0.00 |
| ATOM | 104 | C | LEU | 6 | 4.239 | −0.428 | −6.848 | 1.00 | 0.00 |
| ATOM | 105 | O | LEU | 6 | 3.838 | 0.706 | −6.667 | 1.00 | 0.00 |
| ATOM | 106 | N | CYS | 7 | 4.408 | −0.908 | −8.052 | 1.00 | 0.00 |
| ATOM | 107 | HN | CYS | 7 | 4.721 | −1.830 | −8.171 | 1.00 | 0.00 |
| ATOM | 108 | CA | CYS | 7 | 4.113 | −0.063 | −9.246 | 1.00 | 0.00 |
| ATOM | 109 | HA | CYS | 7 | 3.509 | 0.781 | −8.947 | 1.00 | 0.00 |
| ATOM | 110 | HB1 | CYS | 7 | 5.206 | 1.052 | −10.719 | 1.00 | 0.00 |
| ATOM | 111 | HB2 | CYS | 7 | 6.026 | −0.406 | −10.157 | 1.00 | 0.00 |
| ATOM | 112 | C | CYS | 7 | 3.348 | −0.893 | −10.279 | 1.00 | 0.00 |
| ATOM | 113 | O | CYS | 7 | 3.726 | −2.004 | −10.597 | 1.00 | 0.00 |
| ATOM | 114 | CB | CYS | 7 | 5.422 | 0.438 | −9.857 | 1.00 | 0.00 |
| ATOM | 115 | SG | CYS | 7 | 6.321 | 1.417 | −8.626 | 1.00 | 0.00 |
| ATOM | 116 | N | GLY | 8 | 2.272 | −0.359 | −10.798 | 1.00 | 0.00 |
| ATOM | 117 | HN | GLY | 8 | 1.989 | 0.538 | −10.520 | 1.00 | 0.00 |
| ATOM | 118 | CA | GLY | 8 | 1.470 | −1.108 | −11.809 | 1.00 | 0.00 |
| ATOM | 119 | HA1 | GLY | 8 | 2.057 | −1.925 | −12.201 | 1.00 | 0.00 |
| ATOM | 120 | HA2 | GLY | 8 | 1.195 | −0.442 | −12.616 | 1.00 | 0.00 |
| ATOM | 121 | C | GLY | 8 | 0.206 | −1.665 | −11.152 | 1.00 | 0.00 |
| ATOM | 122 | O | GLY | 8 | −0.493 | −0.968 | −10.441 | 1.00 | 0.00 |
| ATOM | 123 | N | SER | 9 | −0.091 | −2.917 | −11.390 | 1.00 | 0.00 |
| ATOM | 124 | HN | SER | 9 | 0.492 | −3.453 | −11.968 | 1.00 | 0.00 |
| ATOM | 125 | CA | SER | 9 | −1.309 | −3.534 | −10.788 | 1.00 | 0.00 |
| ATOM | 126 | CA | SER | 9 | −2.073 | −2.781 | −10.672 | 1.00 | 0.00 |
| ATOM | 127 | CB | SER | 9 | −1.822 | −4.640 | −11.711 | 1.00 | 0.00 |
| ATOM | 128 | HB1 | SER | 9 | −1.181 | −5.508 | −11.621 | 1.00 | 0.00 |
| ATOM | 129 | HB2 | SER | 9 | −1.810 | −4.293 | −12.731 | 1.00 | 0.00 |
| ATOM | 130 | OG | SER | 9 | −3.154 | −4.977 | −11.346 | 1.00 | 0.00 |
| ATOM | 131 | HG | SER | 9 | −3.683 | −5.002 | −12.147 | 1.00 | 0.00 |
| ATOM | 132 | C | SER | 9 | −0.972 | −4.134 | −9.415 | 1.00 | 0.00 |
| ATOM | 133 | O | SER | 9 | −1.845 | −4.340 | −8.594 | 1.00 | 0.00 |
| ATOM | 134 | N | HIS | 10 | 0.284 | −4.419 | −9.164 | 1.00 | 0.00 |
| ATOM | 135 | HN | HIS | 10 | 0.969 | −4.248 | −9.841 | 1.00 | 0.00 |
| ATOM | 136 | CA | HIS | 10 | 0.677 | −5.009 | −7.849 | 1.00 | 0.00 |
| ATOM | 137 | HA | HIS | 10 | 0.159 | −5.946 | −7.710 | 1.00 | 0.00 |
| ATOM | 138 | CB | HIS | 10 | 2.188 | −5.262 | −7.841 | 1.00 | 0.00 |
| ATOM | 139 | HB1 | HIS | 10 | 2.488 | −5.607 | −6.863 | 1.00 | 0.00 |
| ATOM | 140 | HB2 | HIS | 10 | 2.705 | −4.342 | −8.070 | 1.00 | 0.00 |
| ATOM | 141 | CG | HIS | 10 | 2.548 | −6.305 | −8.872 | 1.00 | 0.00 |
| ATOM | 142 | ND1 | HIS | 10 | 1.608 | −6.886 | −9.715 | 1.00 | 0.00 |
| ATOM | 143 | HD1 | HIS | 10 | 0.648 | −6.690 | −9.733 | 1.00 | 0.00 |
| ATOM | 144 | CD2 | HIS | 10 | 3.750 | −6.882 | −9.204 | 1.00 | 0.00 |
| ATOM | 145 | HD2 | HIS | 10 | 4.697 | −6.655 | −8.738 | 1.00 | 0.00 |
| ATOM | 146 | CE1 | HIS | 10 | 2.255 | −7.766 | −10.500 | 1.00 | 0.00 |
| ATOM | 147 | HE1 | HIS | 10 | 1.775 | −8.370 | −11.255 | 1.00 | 0.00 |
| ATOM | 148 | NE2 | HIS | 10 | 3.562 | −7.802 | −10.231 | 1.00 | 0.00 |
| ATOM | 149 | C | HIS | 10 | 0.314 | −4.052 | −6.702 | 1.00 | 0.00 |
| ATOM | 150 | O | HIS | 10 | 0.243 | −4.455 | −5.557 | 1.00 | 0.00 |
| ATOM | 151 | N | LEU | 11 | 0.089 | −2.792 | −6.994 | 1.00 | 0.00 |
| ATOM | 152 | HN | LEU | 11 | 0.156 | −2.485 | −7.921 | 1.00 | 0.00 |
| ATOM | 153 | CA | LEU | 11 | −0.264 | −1.813 | −5.918 | 1.00 | 0.00 |
| ATOM | 154 | HA | LEU | 11 | 0.542 | −1.764 | −5.202 | 1.00 | 0.00 |

TABLE 4-continued

Atomic coordinates of Asp$^{28}$IP(AspGlyLys) in PDB format

| ATOM | 155 | CB   | LEU | 11 | −0.474 | −0.420 | −6.548 | 1.00 | 0.00 |
|------|-----|------|-----|----|--------|--------|--------|------|------|
| ATOM | 156 | HB1  | LEU | 11 | −1.303 | −0.471 | −7.239 | 1.00 | 0.00 |
| ATOM | 157 | HB2  | LEU | 11 | 0.417  | −0.143 | −7.090 | 1.00 | 0.00 |
| ATOM | 158 | CG   | LEU | 11 | −0.771 | 0.668  | −5.484 | 1.00 | 0.00 |
| ATOM | 159 | HG   | LEU | 11 | −0.601 | 1.639  | −5.929 | 1.00 | 0.00 |
| ATOM | 160 | CD1  | LEU | 11 | −2.235 | 0.588  | −5.040 | 1.00 | 0.00 |
| ATOM | 161 | HD11 | LEU | 11 | −2.305 | 0.002  | −4.134 | 1.00 | 0.00 |
| ATOM | 162 | HD12 | LEU | 11 | −2.823 | 0.121  | −5.817 | 1.00 | 0.00 |
| ATOM | 163 | HD13 | LEU | 11 | −2.609 | 1.584  | −4.853 | 1.00 | 0.00 |
| ATOM | 164 | CD2  | LEU | 11 | 0.146  | 0.514  | −4.260 | 1.00 | 0.00 |
| ATOM | 165 | HD21 | LEU | 11 | −0.214 | −0.294 | −3.640 | 1.00 | 0.00 |
| ATOM | 166 | HD22 | LEU | 11 | 0.144  | 1.432  | −3.691 | 1.00 | 0.00 |
| ATOM | 167 | HD23 | LEU | 11 | 1.151  | 0.296  | −4.589 | 1.00 | 0.00 |
| ATOM | 168 | C    | LEU | 11 | −1.543 | −2.259 | −5.207 | 1.00 | 0.00 |
| ATOM | 169 | O    | LEU | 11 | −1.542 | −2.522 | −4.020 | 1.00 | 0.00 |
| ATOM | 170 | N    | VAL | 12 | −2.636 | −2.322 | −5.922 | 1.00 | 0.00 |
| ATOM | 171 | HN   | VAL | 12 | −2.608 | −2.089 | −6.874 | 1.00 | 0.00 |
| ATOM | 172 | CA   | VAL | 12 | −3.931 | −2.729 | −5.298 | 1.00 | 0.00 |
| ATOM | 173 | HA   | VAL | 12 | −4.203 | −1.999 | −4.550 | 1.00 | 0.00 |
| ATOM | 174 | CB   | VAL | 12 | −5.020 | −2.770 | −6.379 | 1.00 | 0.00 |
| ATOM | 175 | HB   | VAL | 12 | −5.052 | −1.816 | −6.884 | 1.00 | 0.00 |
| ATOM | 176 | CG1  | VAL | 12 | −4.715 | −3.872 | −7.406 | 1.00 | 0.00 |
| ATOM | 177 | HD11 | VAL | 12 | −3.689 | −4.192 | −7.295 | 1.00 | 0.00 |
| ATOM | 178 | HD12 | VAL | 12 | −4.864 | −3.485 | −8.403 | 1.00 | 0.00 |
| ATOM | 179 | HD13 | VAL | 12 | −5.373 | −4.713 | −7.245 | 1.00 | 0.00 |
| ATOM | 180 | CG2  | VAL | 12 | −6.378 | −3.035 | −5.720 | 1.00 | 0.00 |
| ATOM | 181 | HG21 | VAL | 12 | −6.885 | −2.097 | −5.560 | 1.00 | 0.00 |
| ATOM | 182 | HG22 | VAL | 12 | −6.230 | −3.531 | −4.772 | 1.00 | 0.00 |
| ATOM | 183 | HG23 | VAL | 12 | −6.975 | −3.662 | −6.365 | 1.00 | 0.00 |
| ATOM | 184 | C    | VAL | 12 | −3.795 | −4.105 | −4.629 | 1.00 | 0.00 |
| ATOM | 185 | O    | VAL | 12 | −4.496 | −4.415 | −3.684 | 1.00 | 0.00 |
| ATOM | 186 | N    | GLU | 13 | −2.897 | −4.928 | −5.112 | 1.00 | 0.00 |
| ATOM | 187 | HN   | GLU | 13 | −2.343 | −4.655 | −5.873 | 1.00 | 0.00 |
| ATOM | 188 | CA   | GLU | 13 | −2.716 | −6.281 | −4.505 | 1.00 | 0.00 |
| ATOM | 189 | HA   | GLU | 13 | −3.650 | −6.802 | −4.509 | 1.00 | 0.00 |
| ATOM | 190 | CB   | GLU | 13 | −1.675 | −7.072 | −5.302 | 1.00 | 0.00 |
| ATOM | 191 | HB1  | GLU | 13 | −1.299 | −7.882 | −4.696 | 1.00 | 0.00 |
| ATOM | 192 | HB2  | GLU | 13 | −0.860 | −6.418 | −5.577 | 1.00 | 0.00 |
| ATOM | 193 | CG   | GLU | 13 | −2.319 | −7.642 | −6.567 | 1.00 | 0.00 |
| ATOM | 194 | HG1  | GLU | 13 | −2.926 | −6.883 | −7.038 | 1.00 | 0.00 |
| ATOM | 195 | HG2  | GLU | 13 | −2.939 | −8.488 | −6.306 | 1.00 | 0.00 |
| ATOM | 196 | CD   | GLU | 13 | −1.225 | −8.091 | −7.536 | 1.00 | 0.00 |
| ATOM | 197 | OE1  | GLU | 13 | −0.270 | −8.698 | −7.080 | 1.00 | 0.00 |
| ATOM | 198 | OE2  | GLU | 13 | −1.359 | −7.821 | −8.718 | 1.00 | 0.00 |
| ATOM | 199 | C    | GLU | 13 | −2.254 | −6.129 | −3.066 | 1.00 | 0.00 |
| ATOM | 200 | O    | GLU | 13 | −2.698 | −6.838 | −2.188 | 1.00 | 0.00 |
| ATOM | 201 | N    | ALA | 14 | −1.378 | −5.204 | −2.821 | 1.00 | 0.00 |
| ATOM | 202 | HN   | ALA | 14 | −1.044 | −4.644 | −3.552 | 1.00 | 0.00 |
| ATOM | 203 | CA   | ALA | 14 | −0.885 | −4.986 | −1.439 | 1.00 | 0.00 |
| ATOM | 204 | HA   | ALA | 14 | −0.531 | −5.919 | −1.027 | 1.00 | 0.00 |
| ATOM | 205 | CB   | ALA | 14 | 0.254  | −3.979 | −1.475 | 1.00 | 0.00 |
| ATOM | 206 | HB1  | ALA | 14 | −0.159 | −2.981 | −1.506 | 1.00 | 0.00 |
| ATOM | 207 | HB2  | ALA | 14 | 0.855  | −4.148 | −2.355 | 1.00 | 0.00 |
| ATOM | 208 | HB3  | ALA | 14 | 0.862  | −4.092 | −0.591 | 1.00 | 0.00 |
| ATOM | 209 | C    | ALA | 14 | −2.010 | −4.427 | −0.563 | 1.00 | 0.00 |
| ATOM | 210 | O    | ALA | 14 | −1.948 | −4.511 | 0.644  | 1.00 | 0.00 |
| ATOM | 211 | N    | LEU | 15 | −3.018 | −3.829 | −1.154 | 1.00 | 0.00 |
| ATOM | 212 | HN   | LEU | 15 | −3.038 | −3.744 | −2.129 | 1.00 | 0.00 |
| ATOM | 213 | CA   | LEU | 15 | −4.114 | −3.237 | −0.335 | 1.00 | 0.00 |
| ATOM | 214 | HA   | LEU | 15 | −3.678 | −2.805 | 0.553  | 1.00 | 0.00 |
| ATOM | 215 | CB   | LEU | 15 | −4.815 | −2.131 | −1.125 | 1.00 | 0.00 |
| ATOM | 216 | HB1  | LEU | 15 | −5.783 | −1.935 | −0.691 | 1.00 | 0.00 |
| ATOM | 217 | HB2  | LEU | 15 | −4.936 | −2.445 | −2.153 | 1.00 | 0.00 |
| ATOM | 218 | CG   | LEU | 15 | −3.969 | −0.854 | −1.077 | 1.00 | 0.00 |
| ATOM | 219 | HG   | LEU | 15 | −2.977 | −1.073 | −1.450 | 1.00 | 0.00 |
| ATOM | 220 | CD1  | LEU | 15 | −4.617 | 0.221  | −1.951 | 1.00 | 0.00 |
| ATOM | 221 | HD11 | LEU | 15 | −5.679 | 0.032  | −2.029 | 1.00 | 0.00 |
| ATOM | 222 | HD12 | LEU | 15 | −4.176 | 0.199  | −2.938 | 1.00 | 0.00 |
| ATOM | 223 | HD13 | LEU | 15 | −4.457 | 1.192  | −1.507 | 1.00 | 0.00 |
| ATOM | 224 | CD2  | LEU | 15 | −3.873 | −0.343 | 0.370  | 1.00 | 0.00 |
| ATOM | 225 | HD21 | LEU | 15 | −3.530 | 0.683  | 0.370  | 1.00 | 0.00 |
| ATOM | 226 | HD22 | LEU | 15 | −3.175 | −0.955 | 0.927  | 1.00 | 0.00 |
| ATOM | 227 | HD23 | LEU | 15 | −4.847 | −0.396 | 0.835  | 1.00 | 0.00 |
| ATOM | 228 | C    | LEU | 15 | −5.129 | −4.291 | 0.108  | 1.00 | 0.00 |
| ATOM | 229 | O    | LEU | 15 | −5.380 | −4.409 | 1.290  | 1.00 | 0.00 |
| ATOM | 230 | N    | TYR | 16 | −5.728 | −5.057 | −0.787 | 1.00 | 0.00 |
| ATOM | 231 | HN   | TYR | 16 | −5.524 | −4.964 | −1.743 | 1.00 | 0.00 |

TABLE 4-continued

Atomic coordinates of Asp$^{28}$IP(AspGlyLys) in PDB format

| ATOM | 232 | CA | TYR | 16 | −6.725 | −6.069 | −0.290 | 1.00 | 0.00 |
|---|---|---|---|---|---|---|---|---|---|
| ATOM | 233 | HA | TYR | 16 | −7.334 | −5.578 | 0.452 | 1.00 | 0.00 |
| ATOM | 234 | CB | TYR | 16 | −7.655 | −6.628 | −1.371 | 1.00 | 0.00 |
| ATOM | 235 | HB1 | TYR | 16 | −8.424 | −5.905 | −1.580 | 1.00 | 0.00 |
| ATOM | 236 | HB2 | TYR | 16 | −8.115 | −7.527 | −1.002 | 1.00 | 0.00 |
| ATOM | 237 | CG | TYR | 16 | −6.942 | −6.954 | −2.641 | 1.00 | 0.00 |
| ATOM | 238 | CD1 | TYR | 16 | −6.878 | −5.998 | −3.640 | 1.00 | 0.00 |
| ATOM | 239 | HD1 | TYR | 16 | −7.282 | −5.020 | −3.467 | 1.00 | 0.00 |
| ATOM | 240 | CD2 | TYR | 16 | −6.414 | −8.230 | −2.846 | 1.00 | 0.00 |
| ATOM | 241 | HD2 | TYR | 16 | −6.462 | −8.969 | −2.059 | 1.00 | 0.00 |
| ATOM | 242 | CE1 | TYR | 16 | −6.290 | −6.298 | −4.856 | 1.00 | 0.00 |
| ATOM | 243 | HE1 | TYR | 16 | −6.249 | −5.541 | −5.617 | 1.00 | 0.00 |
| ATOM | 244 | CE2 | TYR | 16 | −5.805 | −8.541 | −4.063 | 1.00 | 0.00 |
| ATOM | 245 | HE2 | TYR | 16 | −5.385 | −9.525 | −4.220 | 1.00 | 0.00 |
| ATOM | 246 | CZ | TYR | 16 | −5.748 | −7.574 | −5.078 | 1.00 | 0.00 |
| ATOM | 247 | OH | TYR | 16 | −5.159 | −7.874 | −6.289 | 1.00 | 0.00 |
| ATOM | 248 | HH | TYR | 16 | −5.854 | −7.948 | −6.946 | 1.00 | 0.00 |
| ATOM | 249 | C | TYR | 16 | −5.992 | −7.206 | 0.394 | 1.00 | 0.00 |
| ATOM | 250 | O | TYR | 16 | −6.522 | −7.835 | 1.293 | 1.00 | 0.00 |
| ATOM | 251 | N | LEU | 17 | −4.758 | −7.455 | 0.025 | 1.00 | 0.00 |
| ATOM | 252 | HN | LEU | 17 | −4.336 | −6.915 | −0.674 | 1.00 | 0.00 |
| ATOM | 253 | CA | LEU | 17 | −3.980 | −8.527 | 0.713 | 1.00 | 0.00 |
| ATOM | 254 | HA | LEU | 17 | −4.465 | −9.481 | 0.569 | 1.00 | 0.00 |
| ATOM | 255 | CB | LEU | 17 | −2.558 | −8.573 | 0.151 | 1.00 | 0.00 |
| ATOM | 256 | HB1 | LEU | 17 | −2.022 | −7.685 | 0.448 | 1.00 | 0.00 |
| ATOM | 257 | HB2 | LEU | 17 | −2.602 | −8.628 | −0.925 | 1.00 | 0.00 |
| ATOM | 258 | CG | LEU | 17 | −1.837 | −9.805 | 0.688 | 1.00 | 0.00 |
| ATOM | 259 | HG | LEU | 17 | −1.862 | −9.793 | 1.769 | 1.00 | 0.00 |
| ATOM | 260 | CD1 | LEU | 17 | −2.536 | −11.064 | 0.174 | 1.00 | 0.00 |
| ATOM | 261 | HD11 | LEU | 17 | −1.806 | −11.843 | 0.011 | 1.00 | 0.00 |
| ATOM | 262 | HD12 | LEU | 17 | −3.044 | −10.842 | −0.759 | 1.00 | 0.00 |
| ATOM | 263 | HD13 | LEU | 17 | −3.259 | −11.393 | 0.907 | 1.00 | 0.00 |
| ATOM | 264 | CD2 | LEU | 17 | −0.385 | −9.787 | 0.207 | 1.00 | 0.00 |
| ATOM | 265 | HD21 | LEU | 17 | 0.104 | −8.898 | 0.578 | 1.00 | 0.00 |
| ATOM | 266 | HD22 | LEU | 17 | −0.363 | −9.786 | −0.873 | 1.00 | 0.00 |
| ATOM | 267 | HD23 | LEU | 17 | 0.128 | −10.661 | 0.578 | 1.00 | 0.00 |
| ATOM | 268 | C | LEU | 17 | −3.939 | −8.186 | 2.207 | 1.00 | 0.00 |
| ATOM | 269 | O | LEU | 17 | −3.941 | −9.052 | 3.060 | 1.00 | 0.00 |
| ATOM | 270 | N | VAL | 18 | −3.940 | −6.911 | 2.511 | 1.00 | 0.00 |
| ATOM | 271 | HN | VAL | 18 | −3.959 | −6.242 | 1.798 | 1.00 | 0.00 |
| ATOM | 272 | CA | VAL | 18 | −3.943 | −6.464 | 3.921 | 1.00 | 0.00 |
| ATOM | 273 | HA | VAL | 18 | −3.358 | −7.145 | 4.520 | 1.00 | 0.00 |
| ATOM | 274 | CB | VAL | 18 | −3.370 | −5.042 | 4.015 | 1.00 | 0.00 |
| ATOM | 275 | HB | VAL | 18 | −4.051 | −4.353 | 3.529 | 1.00 | 0.00 |
| ATOM | 276 | CG1 | VAL | 18 | −3.222 | −4.647 | 5.484 | 1.00 | 0.00 |
| ATOM | 277 | HG11 | VAL | 18 | −4.150 | −4.224 | 5.837 | 1.00 | 0.00 |
| ATOM | 278 | HG12 | VAL | 18 | −2.433 | −3.917 | 5.584 | 1.00 | 0.00 |
| ATOM | 279 | HG13 | VAL | 18 | −2.980 | −5.521 | 6.071 | 1.00 | 0.00 |
| ATOM | 280 | CG2 | VAL | 18 | −2.004 | −4.964 | 3.327 | 1.00 | 0.00 |
| ATOM | 281 | HG21 | VAL | 18 | −1.904 | −5.774 | 2.622 | 1.00 | 0.00 |
| ATOM | 282 | HG22 | VAL | 18 | −1.223 | −5.030 | 4.066 | 1.00 | 0.00 |
| ATOM | 283 | HG23 | VAL | 18 | −1.924 | −4.019 | 2.805 | 1.00 | 0.00 |
| ATOM | 284 | C | VAL | 18 | −5.395 | −6.419 | 4.421 | 1.00 | 0.00 |
| ATOM | 285 | O | VAL | 18 | −5.660 | −6.559 | 5.599 | 1.00 | 0.00 |
| ATOM | 286 | N | CYS | 19 | −6.334 | −6.183 | 3.528 | 1.00 | 0.00 |
| ATOM | 287 | HN | CYS | 19 | −6.095 | −6.041 | 2.586 | 1.00 | 0.00 |
| ATOM | 288 | CA | CYS | 19 | −7.765 | −6.079 | 3.939 | 1.00 | 0.00 |
| ATOM | 289 | HA | CYS | 19 | −7.813 | −5.715 | 4.955 | 1.00 | 0.00 |
| ATOM | 290 | HB1 | CYS | 19 | −9.470 | −4.891 | 3.352 | 1.00 | 0.00 |
| ATOM | 291 | HB2 | CYS | 19 | −8.498 | −5.465 | 2.012 | 1.00 | 0.00 |
| ATOM | 292 | C | CYS | 19 | −8.452 | −7.454 | 3.872 | 1.00 | 0.00 |
| ATOM | 293 | O | CYS | 19 | −8.550 | −8.144 | 4.870 | 1.00 | 0.00 |
| ATOM | 294 | CB | CYS | 19 | −8.466 | −5.071 | 3.012 | 1.00 | 0.00 |
| ATOM | 295 | SG | CYS | 19 | −7.549 | −3.504 | 2.992 | 1.00 | 0.00 |
| ATOM | 296 | N | GLY | 20 | −8.933 | −7.860 | 2.718 | 1.00 | 0.00 |
| ATOM | 297 | HN | GLY | 20 | −8.849 | −7.297 | 1.925 | 1.00 | 0.00 |
| ATOM | 298 | CA | GLY | 20 | −9.613 | −9.186 | 2.613 | 1.00 | 0.00 |
| ATOM | 299 | HA1 | GLY | 20 | −10.029 | −9.451 | 3.574 | 1.00 | 0.00 |
| ATOM | 300 | HA2 | GLY | 20 | −8.895 | −9.935 | 2.311 | 1.00 | 0.00 |
| ATOM | 301 | C | GLY | 20 | −10.741 | −9.110 | 1.580 | 1.00 | 0.00 |
| ATOM | 302 | O | GLY | 20 | −10.548 | −8.649 | 0.472 | 1.00 | 0.00 |
| ATOM | 303 | N | GLU | 21 | −11.914 | −9.569 | 1.937 | 1.00 | 0.00 |
| ATOM | 304 | HN | GLU | 21 | −12.038 | −9.939 | 2.837 | 1.00 | 0.00 |
| ATOM | 305 | CA | GLU | 21 | −13.064 | −9.539 | 0.983 | 1.00 | 0.00 |
| ATOM | 306 | HA | GLU | 21 | −12.693 | −9.624 | −0.028 | 1.00 | 0.00 |
| ATOM | 307 | CB | GLU | 21 | −14.004 | −10.713 | 1.283 | 1.00 | 0.00 |
| ATOM | 308 | HB1 | GLU | 21 | −15.030 | −10.392 | 1.186 | 1.00 | 0.00 |

TABLE 4-continued

Atomic coordinates of Asp²⁸IP(AspGlyLys) in PDB format

| ATOM | 309 | HB2 | GLU | 21 | −13.831 | −11.061 | 2.292 | 1.00 | 0.00 |
|------|-----|------|-----|----|---------|---------|-------|------|------|
| ATOM | 310 | CG | GLU | 21 | −13.736 | −11.855 | 0.299 | 1.00 | 0.00 |
| ATOM | 311 | HG1 | GLU | 21 | −13.882 | −12.801 | 0.797 | 1.00 | 0.00 |
| ATOM | 312 | HG2 | GLU | 21 | −12.719 | −11.790 | −0.060 | 1.00 | 0.00 |
| ATOM | 313 | CD | GLU | 21 | −14.702 | −11.748 | −0.882 | 1.00 | 0.00 |
| ATOM | 314 | OE1 | GLU | 21 | −14.275 | −11.299 | −1.932 | 1.00 | 0.00 |
| ATOM | 315 | OE2 | GLU | 21 | −15.853 | −12.118 | −0.716 | 1.00 | 0.00 |
| ATOM | 316 | C | GLU | 21 | −13.835 | −8.223 | 1.132 | 1.00 | 0.00 |
| ATOM | 317 | O | GLU | 21 | −14.459 | −7.753 | 0.199 | 1.00 | 0.00 |
| ATOM | 318 | N | ARG | 22 | −13.808 | −7.631 | 2.302 | 1.00 | 0.00 |
| ATOM | 319 | HN | ARG | 22 | −13.304 | −8.035 | 3.040 | 1.00 | 0.00 |
| ATOM | 320 | CA | ARG | 22 | −14.548 | −6.350 | 2.524 | 1.00 | 0.00 |
| ATOM | 321 | HA | ARG | 22 | −15.605 | −6.522 | 2.398 | 1.00 | 0.00 |
| ATOM | 322 | CB | ARG | 22 | −14.288 | −5.853 | 3.944 | 1.00 | 0.00 |
| ATOM | 323 | HB1 | ARG | 22 | −14.444 | −4.788 | 3.983 | 1.00 | 0.00 |
| ATOM | 324 | HB2 | ARG | 22 | −13.269 | −6.080 | 4.225 | 1.00 | 0.00 |
| ATOM | 325 | CG | ARG | 22 | −15.251 | −6.543 | 4.912 | 1.00 | 0.00 |
| ATOM | 326 | HG1 | ARG | 22 | −14.802 | −7.452 | 5.281 | 1.00 | 0.00 |
| ATOM | 327 | HG2 | ARG | 22 | −16.172 | −6.778 | 4.395 | 1.00 | 0.00 |
| ATOM | 328 | CD | ARG | 22 | −15.549 | −5.610 | 6.085 | 1.00 | 0.00 |
| ATOM | 329 | HD1 | ARG | 22 | −16.250 | −6.085 | 6.755 | 1.00 | 0.00 |
| ATOM | 330 | HD2 | ARG | 22 | −15.973 | −4.689 | 5.714 | 1.00 | 0.00 |
| ATOM | 331 | NE | ARG | 22 | −14.285 | −5.315 | 6.818 | 1.00 | 0.00 |
| ATOM | 332 | HE | ARG | 22 | −13.502 | −4.985 | 6.331 | 1.00 | 0.00 |
| ATOM | 333 | CZ | ARG | 22 | −14.224 | −5.496 | 8.107 | 1.00 | 0.00 |
| ATOM | 334 | NH1 | ARG | 22 | −13.711 | −6.595 | 8.589 | 1.00 | 0.00 |
| ATOM | 335 | HH11 | ARG | 22 | −13.363 | −7.298 | 7.968 | 1.00 | 0.00 |
| ATOM | 336 | HH12 | ARG | 22 | −13.666 | −6.735 | 9.578 | 1.00 | 0.00 |
| ATOM | 337 | NH2 | ARG | 22 | −14.679 | −4.579 | 8.917 | 1.00 | 0.00 |
| ATOM | 338 | HH21 | ARG | 22 | −15.074 | −3.737 | 8.547 | 1.00 | 0.00 |
| ATOM | 339 | HH22 | ARG | 22 | −14.634 | −4.717 | 9.905 | 1.00 | 0.00 |
| ATOM | 340 | C | ARG | 22 | −14.086 | −5.290 | 1.520 | 1.00 | 0.00 |
| ATOM | 341 | O | ARG | 22 | −14.890 | −4.676 | 0.843 | 1.00 | 0.00 |
| ATOM | 342 | N | GLY | 23 | −12.799 | −5.074 | 1.417 | 1.00 | 0.00 |
| ATOM | 343 | HN | GLY | 23 | −12.173 | −5.585 | 1.972 | 1.00 | 0.00 |
| ATOM | 344 | CA | GLY | 23 | −12.281 | −4.057 | 0.456 | 1.00 | 0.00 |
| ATOM | 345 | HA1 | GLY | 23 | −13.077 | −3.381 | 0.182 | 1.00 | 0.00 |
| ATOM | 346 | HA2 | GLY | 23 | −11.913 | −4.556 | −0.429 | 1.00 | 0.00 |
| ATOM | 347 | C | GLY | 23 | −11.146 | −3.266 | 1.102 | 1.00 | 0.00 |
| ATOM | 348 | O | GLY | 23 | −10.816 | −3.465 | 2.256 | 1.00 | 0.00 |
| ATOM | 349 | N | PHE | 24 | −10.547 | −2.370 | 0.361 | 1.00 | 0.00 |
| ATOM | 350 | HN | PHE | 24 | −10.835 | −2.236 | −0.565 | 1.00 | 0.00 |
| ATOM | 351 | CA | PHE | 24 | −9.425 | −1.556 | 0.914 | 1.00 | 0.00 |
| ATOM | 352 | HA | PHE | 24 | −9.307 | −1.785 | 1.957 | 1.00 | 0.00 |
| ATOM | 353 | CB | PHE | 24 | −8.124 | −1.905 | 0.165 | 1.00 | 0.00 |
| ATOM | 354 | HB1 | PHE | 24 | −7.810 | −2.901 | 0.433 | 1.00 | 0.00 |
| ATOM | 355 | HB2 | PHE | 24 | −7.355 | −1.201 | 0.426 | 1.00 | 0.00 |
| ATOM | 356 | CG | PHE | 24 | −8.358 | −1.845 | −1.319 | 1.00 | 0.00 |
| ATOM | 357 | CD1 | PHE | 24 | −8.560 | −0.612 | −1.925 | 1.00 | 0.00 |
| ATOM | 358 | HD1 | PHE | 24 | −8.529 | 0.279 | −1.325 | 1.00 | 0.00 |
| ATOM | 359 | CD2 | PHE | 24 | −8.387 | −3.019 | −2.077 | 1.00 | 0.00 |
| ATOM | 360 | HD2 | PHE | 24 | −8.212 | −3.981 | −1.597 | 1.00 | 0.00 |
| ATOM | 361 | CE1 | PHE | 24 | −8.800 | −0.532 | −3.300 | 1.00 | 0.00 |
| ATOM | 362 | HE1 | PHE | 24 | −8.956 | 0.429 | −3.768 | 1.00 | 0.00 |
| ATOM | 363 | CE2 | PHE | 24 | −8.625 | −2.943 | −3.457 | 1.00 | 0.00 |
| ATOM | 364 | HE2 | PHE | 24 | −8.657 | −3.844 | −4.051 | 1.00 | 0.00 |
| ATOM | 365 | CZ | PHE | 24 | −8.833 | −1.700 | −4.068 | 1.00 | 0.00 |
| ATOM | 366 | HZ | PHE | 24 | −9.018 | −1.643 | −5.130 | 1.00 | 0.00 |
| ATOM | 367 | C | PHE | 24 | −9.755 | −0.061 | 0.759 | 1.00 | 0.00 |
| ATOM | 368 | O | PHE | 24 | −10.883 | 0.304 | 0.486 | 1.00 | 0.00 |
| ATOM | 369 | N | PHE | 25 | −8.782 | 0.806 | 0.931 | 1.00 | 0.00 |
| ATOM | 370 | HN | PHE | 25 | −7.883 | 0.493 | 1.152 | 1.00 | 0.00 |
| ATOM | 371 | CA | PHE | 25 | −9.036 | 2.274 | 0.796 | 1.00 | 0.00 |
| ATOM | 372 | HA | PHE | 25 | −10.093 | 2.450 | 0.662 | 1.00 | 0.00 |
| ATOM | 373 | CB | PHE | 25 | −8.553 | 2.987 | 2.063 | 1.00 | 0.00 |
| ATOM | 374 | HB1 | PHE | 25 | −8.158 | 3.958 | 1.800 | 1.00 | 0.00 |
| ATOM | 375 | HB2 | PHE | 25 | −7.776 | 2.401 | 2.522 | 1.00 | 0.00 |
| ATOM | 376 | CG | PHE | 25 | −9.693 | 3.162 | 3.040 | 1.00 | 0.00 |
| ATOM | 377 | CD1 | PHE | 25 | −9.908 | 4.410 | 3.637 | 1.00 | 0.00 |
| ATOM | 378 | HD1 | PHE | 25 | −9.267 | 5.244 | 3.392 | 1.00 | 0.00 |
| ATOM | 379 | CD2 | PHE | 25 | −10.524 | 2.082 | 3.360 | 1.00 | 0.00 |
| ATOM | 380 | HD2 | PHE | 25 | −10.359 | 1.119 | 2.900 | 1.00 | 0.00 |
| ATOM | 381 | CE1 | PHE | 25 | −10.955 | 4.579 | 4.550 | 1.00 | 0.00 |
| ATOM | 382 | HE1 | PHE | 25 | −11.118 | 5.542 | 5.010 | 1.00 | 0.00 |
| ATOM | 383 | CE2 | PHE | 25 | −11.570 | 2.252 | 4.271 | 1.00 | 0.00 |
| ATOM | 384 | HE2 | PHE | 25 | −12.210 | 1.421 | 4.514 | 1.00 | 0.00 |
| ATOM | 385 | CZ | PHE | 25 | −11.787 | 3.500 | 4.867 | 1.00 | 0.00 |

TABLE 4-continued

Atomic coordinates of Asp²⁸IP(AspGlyLys) in PDB format

| ATOM | 386 | HZ | PHE | 25 | -12.594 | 3.629 | 5.572 | 1.00 | 0.00 |
|---|---|---|---|---|---|---|---|---|---|
| ATOM | 387 | C | PHE | 25 | -8.263 | 2.828 | -0.409 | 1.00 | 0.00 |
| ATOM | 388 | O | PHE | 25 | -7.421 | 2.161 | -0.979 | 1.00 | 0.00 |
| ATOM | 389 | N | TYR | 26 | -8.540 | 4.051 | -0.784 | 1.00 | 0.00 |
| ATOM | 390 | HN | TYR | 26 | -9.216 | 4.567 | -0.297 | 1.00 | 0.00 |
| ATOM | 391 | CA | TYR | 26 | -7.825 | 4.671 | -1.938 | 1.00 | 0.00 |
| ATOM | 392 | HA | TYR | 26 | -6.785 | 4.381 | -1.915 | 1.00 | 0.00 |
| ATOM | 393 | CB | TYR | 26 | -8.463 | 4.196 | -3.248 | 1.00 | 0.00 |
| ATOM | 394 | HB1 | TYR | 26 | -9.171 | 4.934 | -3.593 | 1.00 | 0.00 |
| ATOM | 395 | HB2 | TYR | 26 | -8.975 | 3.259 | -3.078 | 1.00 | 0.00 |
| ATOM | 396 | CG | TYR | 26 | -7.391 | 4.000 | -4.295 | 1.00 | 0.00 |
| ATOM | 397 | CD1 | TYR | 26 | -7.086 | 5.034 | -5.188 | 1.00 | 0.00 |
| ATOM | 398 | HD1 | TYR | 26 | -7.617 | 5.973 | -5.129 | 1.00 | 0.00 |
| ATOM | 399 | CD2 | TYR | 26 | -6.701 | 2.783 | -4.373 | 1.00 | 0.00 |
| ATOM | 400 | HD2 | TYR | 26 | -6.936 | 1.985 | -3.684 | 1.00 | 0.00 |
| ATOM | 401 | CE1 | TYR | 26 | -6.093 | 4.852 | -6.159 | 1.00 | 0.00 |
| ATOM | 402 | HE1 | TYR | 26 | -5.858 | 5.650 | -6.847 | 1.00 | 0.00 |
| ATOM | 403 | CE2 | TYR | 26 | -5.708 | 2.602 | -5.344 | 1.00 | 0.00 |
| ATOM | 404 | HE2 | TYR | 26 | -5.177 | 1.663 | -5.404 | 1.00 | 0.00 |
| ATOM | 405 | CZ | TYR | 26 | -5.403 | 3.637 | -6.236 | 1.00 | 0.00 |
| ATOM | 406 | OH | TYR | 26 | -4.425 | 3.459 | -7.192 | 1.00 | 0.00 |
| ATOM | 407 | HH | TYR | 26 | -4.787 | 2.908 | -7.890 | 1.00 | 0.00 |
| ATOM | 408 | C | TYR | 26 | -7.934 | 6.195 | -1.835 | 1.00 | 0.00 |
| ATOM | 409 | O | TYR | 26 | -8.901 | 6.787 | -2.277 | 1.00 | 0.00 |
| ATOM | 410 | N | THR | 27 | -6.953 | 6.830 | -1.241 | 1.00 | 0.00 |
| ATOM | 411 | HN | THR | 27 | -6.191 | 6.325 | -0.888 | 1.00 | 0.00 |
| ATOM | 412 | CA | THR | 27 | -6.994 | 8.316 | -1.090 | 1.00 | 0.00 |
| ATOM | 413 | HA | THR | 27 | -7.965 | 8.612 | -0.720 | 1.00 | 0.00 |
| ATOM | 414 | CB | THR | 27 | -5.915 | 8.758 | -0.091 | 1.00 | 0.00 |
| ATOM | 415 | HB | THR | 27 | -6.127 | 8.330 | 0.876 | 1.00 | 0.00 |
| ATOM | 416 | OG1 | THR | 27 | -5.920 | 10.175 | 0.008 | 1.00 | 0.00 |
| ATOM | 417 | HG1 | THR | 27 | -6.818 | 10.458 | 0.194 | 1.00 | 0.00 |
| ATOM | 418 | CG2 | THR | 27 | -4.535 | 8.282 | -0.562 | 1.00 | 0.00 |
| ATOM | 419 | HG21 | THR | 27 | -4.643 | 7.648 | -1.431 | 1.00 | 0.00 |
| ATOM | 420 | HG22 | THR | 27 | -4.058 | 7.725 | 0.231 | 1.00 | 0.00 |
| ATOM | 421 | HG23 | THR | 27 | -3.926 | 9.137 | -0.814 | 1.00 | 0.00 |
| ATOM | 422 | C | THR | 27 | -6.743 | 8.988 | -2.442 | 1.00 | 0.00 |
| ATOM | 423 | O | THR | 27 | -6.319 | 8.357 | -3.392 | 1.00 | 0.00 |
| ATOM | 424 | N | ASP | 28 | -6.999 | 10.268 | -2.527 | 1.00 | 0.00 |
| ATOM | 425 | HN | ASP | 28 | -7.337 | 10.750 | -1.743 | 1.00 | 0.00 |
| ATOM | 426 | CA | ASP | 28 | -6.779 | 11.004 | -3.806 | 1.00 | 0.00 |
| ATOM | 427 | HA | ASP | 28 | -5.809 | 10.748 | -4.207 | 1.00 | 0.00 |
| ATOM | 428 | CB | ASP | 28 | -7.870 | 10.622 | -4.812 | 1.00 | 0.00 |
| ATOM | 429 | HB1 | ASP | 28 | -8.163 | 11.495 | -5.377 | 1.00 | 0.00 |
| ATOM | 430 | HB2 | ASP | 28 | -8.726 | 10.231 | -4.281 | 1.00 | 0.00 |
| ATOM | 431 | CG | ASP | 28 | -7.333 | 9.556 | -5.771 | 1.00 | 0.00 |
| ATOM | 432 | OD1 | ASP | 28 | -6.648 | 9.924 | -6.711 | 1.00 | 0.00 |
| ATOM | 433 | OD2 | ASP | 28 | -7.617 | 8.390 | -5.549 | 1.00 | 0.00 |
| ATOM | 434 | C | ASP | 28 | -6.837 | 12.509 | -3.534 | 1.00 | 0.00 |
| ATOM | 435 | O | ASP | 28 | -5.850 | 13.209 | -3.651 | 1.00 | 0.00 |
| ATOM | 436 | N | LYS | 29 | -7.992 | 13.007 | -3.169 | 1.00 | 0.00 |
| ATOM | 437 | HN | LYS | 29 | -8.770 | 12.418 | -3.083 | 1.00 | 0.00 |
| ATOM | 438 | CA | LYS | 29 | -8.126 | 14.466 | -2.885 | 1.00 | 0.00 |
| ATOM | 439 | HA | LYS | 29 | -7.666 | 15.029 | -3.684 | 1.00 | 0.00 |
| ATOM | 440 | CB | LYS | 29 | -9.614 | 14.835 | -2.798 | 1.00 | 0.00 |
| ATOM | 441 | HB1 | LYS | 29 | -10.092 | 14.617 | -3.741 | 1.00 | 0.00 |
| ATOM | 442 | HB2 | LYS | 29 | -9.708 | 15.890 | -2.585 | 1.00 | 0.00 |
| ATOM | 443 | CG | LYS | 29 | -10.293 | 14.027 | -1.685 | 1.00 | 0.00 |
| ATOM | 444 | HG1 | LYS | 29 | -10.315 | 14.614 | -0.779 | 1.00 | 0.00 |
| ATOM | 445 | HG2 | LYS | 29 | -9.741 | 13.116 | -1.510 | 1.00 | 0.00 |
| ATOM | 446 | CD | LYS | 29 | -11.725 | 13.685 | -2.101 | 1.00 | 0.00 |
| ATOM | 447 | HD1 | LYS | 29 | -11.719 | 12.806 | -2.728 | 1.00 | 0.00 |
| ATOM | 448 | HD2 | LYS | 29 | -12.149 | 14.515 | -2.648 | 1.00 | 0.00 |
| ATOM | 449 | CE | LYS | 29 | -12.565 | 13.413 | -0.853 | 1.00 | 0.00 |
| ATOM | 450 | HE1 | LYS | 29 | -13.613 | 13.525 | -1.093 | 1.00 | 0.00 |
| ATOM | 451 | HE2 | LYS | 29 | -12.297 | 14.115 | -0.078 | 1.00 | 0.00 |
| ATOM | 452 | NZ | LYS | 29 | -12.311 | 12.024 | -0.375 | 1.00 | 0.00 |
| ATOM | 453 | HZ1 | LYS | 29 | -11.297 | 11.810 | -0.453 | 1.00 | 0.00 |
| ATOM | 454 | HZ2 | LYS | 29 | -12.854 | 11.353 | -0.957 | 1.00 | 0.00 |
| ATOM | 455 | HZ3 | LYS | 29 | -12.605 | 11.939 | 0.618 | 1.00 | 0.00 |
| ATOM | 456 | C | LYS | 29 | -7.429 | 14.801 | -1.562 | 1.00 | 0.00 |
| ATOM | 457 | O | LYS | 29 | -6.940 | 15.899 | -1.369 | 1.00 | 0.00 |
| ATOM | 458 | N | ASP | 20 | -7.387 | 13.862 | -0.651 | 1.00 | 0.00 |
| ATOM | 459 | HN | ASP | 30 | -7.793 | 12.989 | -0.833 | 1.00 | 0.00 |
| ATOM | 460 | CA | ASP | 30 | -6.730 | 14.112 | 0.667 | 1.00 | 0.00 |
| ATOM | 461 | HA | ASP | 30 | -7.187 | 14.969 | 1.138 | 1.00 | 0.00 |
| ATOM | 462 | CB | ASP | 30 | -6.905 | 12.884 | 1.562 | 1.00 | 0.00 |

TABLE 4-continued

Atomic coordinates of Asp$^{28}$IP(AspGlyLys) in PDB format

| ATOM | 463 | HB1 | ASP | 30 | −6.222 | 12.109 | 1.249 | 1.00 | 0.00 |
|------|-----|------|-----|----|--------|--------|--------|------|------|
| ATOM | 464 | HB2 | ASP | 30 | −7.920 | 12.523 | 1.481 | 1.00 | 0.00 |
| ATOM | 465 | CG | ASP | 30 | −6.612 | 13.262 | 3.016 | 1.00 | 0.00 |
| ATOM | 466 | OD1 | ASP | 30 | −6.960 | 14.367 | 3.402 | 1.00 | 0.00 |
| ATOM | 467 | OD2 | ASP | 30 | −6.045 | 12.442 | 3.719 | 1.00 | 0.00 |
| ATOM | 468 | C | ASP | 30 | −5.238 | 14.384 | 0.456 | 1.00 | 0.00 |
| ATOM | 469 | O | ASP | 30 | −4.735 | 15.434 | 0.811 | 1.00 | 0.00 |
| ATOM | 470 | N | GLY | 31 | −4.526 | 13.444 | −0.116 | 1.00 | 0.00 |
| ATOM | 471 | HN | GLY | 31 | −4.956 | 12.607 | −0.392 | 1.00 | 0.00 |
| ATOM | 472 | CA | GLY | 31 | −3.066 | 13.643 | −0.351 | 1.00 | 0.00 |
| ATOM | 473 | HA1 | GLY | 31 | −2.510 | 12.870 | 0.158 | 1.00 | 0.00 |
| ATOM | 474 | HA2 | GLY | 31 | −2.769 | 14.611 | 0.028 | 1.00 | 0.00 |
| ATOM | 475 | C | GLY | 31 | −2.772 | 13.569 | −1.851 | 1.00 | 0.00 |
| ATOM | 476 | O | GLY | 31 | −3.342 | 14.300 | −2.639 | 1.00 | 0.00 |
| ATOM | 477 | N | LYS | 32 | −1.887 | 12.690 | −2.246 | 1.00 | 0.00 |
| ATOM | 478 | HN | LYS | 32 | −1.445 | 12.114 | −1.589 | 1.00 | 0.00 |
| ATOM | 479 | CA | LYS | 32 | −1.550 | 12.559 | −3.694 | 1.00 | 0.00 |
| ATOM | 480 | HA | LYS | 32 | −2.213 | 13.182 | −4.274 | 1.00 | 0.00 |
| ATOM | 481 | CB | LYS | 32 | −0.102 | 13.003 | −3.922 | 1.00 | 0.00 |
| ATOM | 482 | HB1 | LYS | 32 | 0.545 | 12.139 | −3.924 | 1.00 | 0.00 |
| ATOM | 483 | HB2 | LYS | 32 | 0.198 | 13.675 | −3.131 | 1.00 | 0.00 |
| ATOM | 484 | CG | LYS | 32 | 0.004 | 13.719 | −5.269 | 1.00 | 0.00 |
| ATOM | 485 | HG1 | LYS | 32 | −0.951 | 14.154 | −5.522 | 1.00 | 0.00 |
| ATOM | 486 | HG2 | LYS | 32 | 0.290 | 13.010 | −6.032 | 1.00 | 0.00 |
| ATOM | 487 | CD | LYS | 32 | 1.058 | 14.827 | −5.180 | 1.00 | 0.00 |
| ATOM | 488 | HD1 | LYS | 32 | 2.023 | 14.427 | −5.452 | 1.00 | 0.00 |
| ATOM | 489 | HD2 | LYS | 32 | 1.097 | 15.203 | −4.168 | 1.00 | 0.00 |
| ATOM | 490 | CE | LYS | 32 | 0.695 | 15.967 | −6.137 | 1.00 | 0.00 |
| ATOM | 491 | HE1 | LYS | 32 | −0.301 | 15.816 | −6.527 | 1.00 | 0.00 |
| ATOM | 492 | HE2 | LYS | 32 | 1.401 | 15.990 | −6.953 | 1.00 | 0.00 |
| ATOM | 493 | NZ | LYS | 32 | 0.746 | 17.263 | −5.402 | 1.00 | 0.00 |
| ATOM | 494 | HZ1 | LYS | 32 | 1.615 | 17.304 | −4.833 | 1.00 | 0.00 |
| ATOM | 495 | HZ2 | LYS | 32 | −0.083 | 17.339 | −4.777 | 1.00 | 0.00 |
| ATOM | 496 | HZ3 | LYS | 32 | 0.741 | 18.048 | −6.082 | 1.00 | 0.00 |
| ATOM | 497 | C | LYS | 32 | −1.712 | 11.100 | −4.127 | 1.00 | 0.00 |
| ATOM | 498 | O | LYS | 32 | −1.028 | 10.629 | −5.015 | 1.00 | 0.00 |
| ATOM | 499 | N | GLY | 33 | −2.614 | 10.385 | −3.504 | 1.00 | 0.00 |
| ATOM | 500 | HN | GLY | 33 | −3.152 | 10.792 | −2.792 | 1.00 | 0.00 |
| ATOM | 501 | CA | GLY | 33 | −2.831 | 8.956 | −3.872 | 1.00 | 0.00 |
| ATOM | 502 | HA1 | GLY | 33 | −2.770 | 8.848 | −4.945 | 1.00 | 0.00 |
| ATOM | 503 | HA2 | GLY | 33 | −3.808 | 8.643 | −3.532 | 1.00 | 0.00 |
| ATOM | 504 | C | GLY | 33 | −1.758 | 8.085 | −3.216 | 1.00 | 0.00 |
| ATOM | 505 | O | GLY | 33 | −0.590 | 8.419 | −3.217 | 1.00 | 0.00 |
| ATOM | 506 | N | ILE | 34 | −2.151 | 6.971 | −2.656 | 1.00 | 0.00 |
| ATOM | 507 | HN | ILE | 34 | −3.101 | 6.728 | −2.667 | 1.00 | 0.00 |
| ATOM | 508 | CA | ILE | 34 | −1.166 | 6.063 | −1.993 | 1.00 | 0.00 |
| ATOM | 509 | HA | ILE | 34 | −0.651 | 6.600 | −1.211 | 1.00 | 0.00 |
| ATOM | 510 | CB | ILE | 34 | −1.905 | 4.872 | −1.389 | 1.00 | 0.00 |
| ATOM | 511 | HB | ILE | 34 | −1.184 | 4.158 | −1.016 | 1.00 | 0.00 |
| ATOM | 512 | CG1 | ILE | 34 | −2.780 | 4.208 | −2.463 | 1.00 | 0.00 |
| ATOM | 513 | HG11 | ILE | 34 | −2.453 | 4.521 | −3.443 | 1.00 | 0.00 |
| ATOM | 514 | HG12 | ILE | 34 | −3.812 | 4.497 | −2.320 | 1.00 | 0.00 |
| ATOM | 515 | CG2 | ILE | 34 | −2.783 | 5.348 | −0.237 | 1.00 | 0.00 |
| ATOM | 516 | HG21 | ILE | 34 | −3.214 | 4.491 | 0.255 | 1.00 | 0.00 |
| ATOM | 517 | HD22 | ILE | 34 | −3.572 | 5.977 | −0.621 | 1.00 | 0.00 |
| ATOM | 518 | HG23 | ILE | 34 | −2.185 | 5.906 | 0.466 | 1.00 | 0.00 |
| ATOM | 519 | CD1 | ILE | 34 | −2.660 | 2.686 | −2.356 | 1.00 | 0.00 |
| ATOM | 520 | HD11 | ILE | 34 | −3.421 | 2.221 | −2.965 | 1.00 | 0.00 |
| ATOM | 521 | HD12 | ILE | 34 | −2.791 | 2.387 | −1.326 | 1.00 | 0.00 |
| ATOM | 522 | HD13 | ILE | 34 | −1.685 | 2.376 | −2.700 | 1.00 | 0.00 |
| ATOM | 523 | C | ILE | 34 | −0.146 | 5.536 | −3.011 | 1.00 | 0.00 |
| ATOM | 524 | O | ILE | 34 | 0.905 | 5.052 | −2.641 | 1.00 | 0.00 |
| ATOM | 525 | N | VAL | 35 | −0.460 | 5.593 | −4.280 | 1.00 | 0.00 |
| ATOM | 526 | HN | VAL | 35 | −1.324 | 5.962 | −4.555 | 1.00 | 0.00 |
| ATOM | 527 | CA | VAL | 35 | 0.479 | 5.063 | −5.316 | 1.00 | 0.00 |
| ATOM | 528 | HA | VAL | 35 | 0.679 | 4.022 | −5.111 | 1.00 | 0.00 |
| ATOM | 529 | CB | VAL | 35 | −0.172 | 5.185 | −6.695 | 1.00 | 0.00 |
| ATOM | 530 | HB | VAL | 35 | −0.280 | 6.229 | −6.951 | 1.00 | 0.00 |
| ATOM | 531 | CG1 | VAL | 35 | 0.706 | 4.491 | −7.739 | 1.00 | 0.00 |
| ATOM | 532 | HG11 | VAL | 35 | 0.080 | 4.041 | −8.496 | 1.00 | 0.00 |
| ATOM | 533 | HG12 | VAL | 35 | 1.299 | 3.725 | −7.259 | 1.00 | 0.00 |
| ATOM | 534 | HG13 | VAL | 35 | 1.360 | 5.218 | −8.198 | 1.00 | 0.00 |
| ATOM | 535 | CG2 | VAL | 35 | −1.551 | 4.518 | −6.665 | 1.00 | 0.00 |
| ATOM | 536 | HG21 | VAL | 35 | −1.505 | 3.626 | −6.058 | 1.00 | 0.00 |
| ATOM | 537 | HG22 | VAL | 35 | −1.847 | 4.255 | −7.669 | 1.00 | 0.00 |
| ATOM | 538 | HG23 | VAL | 35 | −2.273 | 5.204 | −6.245 | 1.00 | 0.00 |
| ATOM | 539 | C | VAL | 35 | 1.802 | 5.840 | −5.303 | 1.00 | 0.00 |

TABLE 4-continued

Atomic coordinates of Asp²⁸IP(AspGlyLys) in PDB format

| ATOM | 540 | O | VAL | 35 | 2.820 | 5.331 | −5.726 | 1.00 | 0.00 |
|------|-----|------|-----|----|-------|-------|--------|------|------|
| ATOM | 541 | N | GLU | 36 | 1.799 | 7.063 | −4.833 | 1.00 | 0.00 |
| ATOM | 542 | HN | GLU | 36 | 0.965 | 7.458 | −4.504 | 1.00 | 0.00 |
| ATOM | 543 | CA | GLU | 36 | 3.066 | 7.861 | −4.814 | 1.00 | 0.00 |
| ATOM | 544 | HA | GLU | 36 | 3.623 | 7.664 | −5.718 | 1.00 | 0.00 |
| ATOM | 545 | CB | GLU | 36 | 2.737 | 9.359 | −4.745 | 1.00 | 0.00 |
| ATOM | 546 | HB1 | GLU | 36 | 2.149 | 9.635 | −5.608 | 1.00 | 0.00 |
| ATOM | 547 | HB2 | GLU | 36 | 3.657 | 9.926 | −4.745 | 1.00 | 0.00 |
| ATOM | 548 | CG | GLU | 36 | 1.940 | 9.671 | −3.469 | 1.00 | 0.00 |
| ATOM | 549 | HG1 | GLU | 36 | 1.907 | 8.794 | −2.840 | 1.00 | 0.00 |
| ATOM | 550 | HG2 | GLU | 36 | 0.934 | 9.957 | −3.739 | 1.00 | 0.00 |
| ATOM | 551 | CD | GLU | 36 | 2.607 | 10.817 | −2.704 | 1.00 | 0.00 |
| ATOM | 552 | OE1 | GLU | 36 | 2.693 | 11.902 | −3.257 | 1.00 | 0.00 |
| ATOM | 553 | OE2 | GLU | 36 | 3.017 | 10.591 | −1.577 | 1.00 | 0.00 |
| ATOM | 554 | C | GLU | 36 | 3.931 | 7.469 | −3.607 | 1.00 | 0.00 |
| ATOM | 555 | O | GLU | 36 | 5.117 | 7.727 | −3.586 | 1.00 | 0.00 |
| ATOM | 556 | N | GLN | 37 | 3.350 | 6.870 | −2.599 | 1.00 | 0.00 |
| ATOM | 557 | HN | GLN | 37 | 2.392 | 6.686 | −2.626 | 1.00 | 0.00 |
| ATOM | 558 | CA | GLN | 37 | 4.148 | 6.481 | −1.397 | 1.00 | 0.00 |
| ATOM | 559 | HA | GLN | 37 | 4.977 | 7.165 | −1.285 | 1.00 | 0.00 |
| ATOM | 560 | CB | GLN | 37 | 3.261 | 6.559 | −0.153 | 1.00 | 0.00 |
| ATOM | 561 | HB1 | GLN | 37 | 2.696 | 5.644 | −0.056 | 1.00 | 0.00 |
| ATOM | 562 | HB2 | GLN | 37 | 2.583 | 7.396 | −0.247 | 1.00 | 0.00 |
| ATOM | 563 | CG | GLN | 37 | 4.141 | 6.748 | 1.085 | 1.00 | 0.00 |
| ATOM | 564 | HG1 | GLN | 37 | 4.996 | 7.357 | 0.829 | 1.00 | 0.00 |
| ATOM | 565 | HG2 | GLN | 37 | 4.479 | 5.783 | 1.435 | 1.00 | 0.00 |
| ATOM | 566 | CD | GLN | 37 | 3.337 | 7.438 | 2.188 | 1.00 | 0.00 |
| ATOM | 567 | OE1 | GLN | 37 | 3.428 | 8.637 | 2.363 | 1.00 | 0.00 |
| ATOM | 568 | NE2 | GLN | 37 | 2.549 | 6.726 | 2.946 | 1.00 | 0.00 |
| ATOM | 569 | HE21 | GLN | 37 | 2.476 | 5.760 | 2.806 | 1.00 | 0.00 |
| ATOM | 570 | HE22 | GLN | 37 | 2.033 | 7.159 | 3.658 | 1.00 | 0.00 |
| ATOM | 571 | C | GLN | 37 | 4.689 | 5.053 | −1.548 | 1.00 | 0.00 |
| ATOM | 572 | O | GLN | 37 | 5.778 | 4.749 | −1.099 | 1.00 | 0.00 |
| ATOM | 573 | N | CYS | 38 | 3.930 | 4.169 | −2.150 | 1.00 | 0.00 |
| ATOM | 574 | HN | CYS | 38 | 3.049 | 4.430 | −2.488 | 1.00 | 0.00 |
| ATOM | 575 | CA | CYS | 38 | 4.396 | 2.753 | −2.299 | 1.00 | 0.00 |
| ATOM | 576 | HA | CYS | 38 | 5.053 | 2.514 | −1.480 | 1.00 | 0.00 |
| ATOM | 577 | HB1 | CYS | 38 | 3.526 | 0.793 | −2.375 | 1.00 | 0.00 |
| ATOM | 578 | HB2 | CYS | 38 | 2.520 | 2.059 | −3.077 | 1.00 | 0.00 |
| ATOM | 579 | C | CYS | 38 | 5.164 | 2.558 | −3.610 | 1.00 | 0.00 |
| ATOM | 580 | O | CYS | 38 | 6.166 | 1.873 | −3.639 | 1.00 | 0.00 |
| ATOM | 581 | CB | CYS | 38 | 3.188 | 1.813 | −2.264 | 1.00 | 0.00 |
| ATOM | 582 | SG | CYS | 38 | 2.305 | 1.990 | −0.686 | 1.00 | 0.00 |
| ATOM | 583 | N | CYS | 39 | 4.717 | 3.135 | −4.695 | 1.00 | 0.00 |
| ATOM | 584 | HN | CYS | 39 | 3.906 | 3.683 | −4.666 | 1.00 | 0.00 |
| ATOM | 585 | CA | CYS | 39 | 5.459 | 2.950 | −5.982 | 1.00 | 0.00 |
| ATOM | 586 | HA | CYS | 39 | 5.633 | 1.897 | −6.130 | 1.00 | 0.00 |
| ATOM | 587 | HB1 | CYS | 39 | 4.453 | 4.551 | −6.994 | 1.00 | 0.00 |
| ATOM | 588 | HB2 | CYS | 39 | 3.678 | 2.985 | −7.182 | 1.00 | 0.00 |
| ATOM | 589 | C | CYS | 39 | 6.813 | 3.671 | −5.901 | 1.00 | 0.00 |
| ATOM | 590 | O | CYS | 39 | 7.723 | 3.370 | −6.650 | 1.00 | 0.00 |
| ATOM | 591 | CB | CYS | 39 | 4.626 | 3.499 | −7.149 | 1.00 | 0.00 |
| ATOM | 592 | SG | CYS | 39 | 5.492 | 3.260 | −8.732 | 1.00 | 0.00 |
| ATOM | 593 | N | THR | 40 | 6.958 | 4.611 | −4.994 | 1.00 | 0.00 |
| ATOM | 594 | HN | THR | 40 | 6.216 | 4.837 | −4.397 | 1.00 | 0.00 |
| ATOM | 595 | CA | THR | 40 | 8.256 | 5.337 | −4.866 | 1.00 | 0.00 |
| ATOM | 596 | HA | THR | 40 | 8.733 | 5.391 | −5.833 | 1.00 | 0.00 |
| ATOM | 597 | CB | THR | 40 | 8.000 | 6.751 | −4.343 | 1.00 | 0.00 |
| ATOM | 598 | HB | THR | 40 | 8.940 | 7.258 | −4.199 | 1.00 | 0.00 |
| ATOM | 599 | OG1 | THR | 40 | 7.305 | 6.680 | −3.107 | 1.00 | 0.00 |
| ATOM | 600 | HG1 | THR | 40 | 7.327 | 7.550 | −2.702 | 1.00 | 0.00 |
| ATOM | 601 | CG2 | THR | 40 | 7.164 | 7.527 | −5.364 | 1.00 | 0.00 |
| ATOM | 602 | HG21 | THR | 40 | 7.651 | 7.496 | −6.326 | 1.00 | 0.00 |
| ATOM | 603 | HG22 | THR | 40 | 7.066 | 8.554 | −5.042 | 1.00 | 0.00 |
| ATOM | 604 | HG23 | THR | 40 | 6.183 | 7.080 | −5.442 | 1.00 | 0.00 |
| ATOM | 605 | C | THR | 40 | 9.166 | 4.582 | −3.891 | 1.00 | 0.00 |
| ATOM | 606 | O | THR | 40 | 10.293 | 4.253 | −4.215 | 1.00 | 0.00 |
| ATOM | 607 | N | SER | 41 | 8.686 | 4.300 | −2.702 | 1.00 | 0.00 |
| ATOM | 608 | HN | SER | 41 | 7.775 | 4.572 | −2.467 | 1.00 | 0.00 |
| ATOM | 609 | CA | SER | 41 | 9.524 | 3.562 | −1.709 | 1.00 | 0.00 |
| ATOM | 610 | HA | SER | 41 | 10.499 | 3.375 | −2.134 | 1.00 | 0.00 |
| ATOM | 611 | CB | SER | 41 | 9.670 | 4.394 | −0.435 | 1.00 | 0.00 |
| ATOM | 612 | HB1 | SER | 41 | 8.877 | 4.137 | 0.255 | 1.00 | 0.00 |
| ATOM | 613 | HB2 | SER | 41 | 9.604 | 5.441 | −0.679 | 1.00 | 0.00 |
| ATOM | 614 | OG | SER | 41 | 10.936 | 4.128 | 0.153 | 1.00 | 0.00 |
| ATOM | 615 | HG | SER | 41 | 10.794 | 3.925 | 1.080 | 1.00 | 0.00 |
| ATOM | 616 | C | SER | 41 | 8.860 | 2.225 | −1.377 | 1.00 | 0.00 |

TABLE 4-continued

Atomic coordinates of Asp²⁸IP(AspGlyLys) in PDB format

| ATOM | 617 | O | SER | 41 | 7.796 | 1.921 | −1.867 | 1.00 | 0.00 |
|---|---|---|---|---|---|---|---|---|---|
| ATOM | 618 | N | ILE | 42 | 9.489 | 1.418 | −0.567 | 1.00 | 0.00 |
| ATOM | 619 | HN | ILE | 42 | 10.357 | 1.676 | −0.193 | 1.00 | 0.00 |
| ATOM | 620 | CA | ILE | 42 | 8.897 | 0.088 | −0.235 | 1.00 | 0.00 |
| ATOM | 621 | HA | ILE | 42 | 8.391 | −0.300 | −1.106 | 1.00 | 0.00 |
| ATOM | 622 | CB | ILE | 42 | 10.011 | −0.883 | 0.172 | 1.00 | 0.00 |
| ATOM | 623 | HB | ILE | 42 | 10.391 | −0.610 | 1.147 | 1.00 | 0.00 |
| ATOM | 624 | CG1 | ILE | 42 | 11.145 | −0.836 | −0.860 | 1.00 | 0.00 |
| ATOM | 625 | HG11 | ILE | 42 | 11.496 | 0.180 | −0.962 | 1.00 | 0.00 |
| ATOM | 626 | HG12 | ILE | 42 | 10.777 | −1.186 | −1.813 | 1.00 | 0.00 |
| ATOM | 627 | CG2 | ILE | 42 | 9.443 | −2.298 | 0.224 | 1.00 | 0.00 |
| ATOM | 628 | HG21 | ILE | 42 | 9.306 | −2.663 | −0.783 | 1.00 | 0.00 |
| ATOM | 629 | HG22 | ILE | 42 | 8.494 | −2.287 | 0.737 | 1.00 | 0.00 |
| ATOM | 630 | HG23 | ILE | 42 | 10.131 | −2.941 | 0.750 | 1.00 | 0.00 |
| ATOM | 631 | CD1 | ILE | 42 | 12.301 | −1.729 | −0.400 | 1.00 | 0.00 |
| ATOM | 632 | HD11 | ILE | 42 | 12.203 | −2.705 | −0.854 | 1.00 | 0.00 |
| ATOM | 633 | HD12 | ILE | 42 | 12.275 | −1.825 | 0.675 | 1.00 | 0.00 |
| ATOM | 634 | HD13 | ILE | 42 | 13.239 | −1.285 | −0.700 | 1.00 | 0.00 |
| ATOM | 635 | C | ILE | 42 | 7.888 | 0.233 | 0.907 | 1.00 | 0.00 |
| ATOM | 636 | O | ILE | 42 | 8.249 | 0.470 | 2.044 | 1.00 | 0.00 |
| ATOM | 637 | N | CYS | 43 | 6.621 | 0.082 | 0.604 | 1.00 | 0.00 |
| ATOM | 638 | HN | CYS | 43 | 6.363 | −0.113 | −0.322 | 1.00 | 0.00 |
| ATOM | 639 | CA | CYS | 43 | 5.569 | 0.198 | 1.656 | 1.00 | 0.00 |
| ATOM | 640 | HA | CYS | 43 | 5.746 | 1.082 | 2.251 | 1.00 | 0.00 |
| ATOM | 641 | HB1 | CYS | 43 | 3.453 | −0.182 | 1.629 | 1.00 | 0.00 |
| ATOM | 642 | HB2 | CYS | 43 | 4.214 | −0.215 | 0.039 | 1.00 | 0.00 |
| ATOM | 643 | C | CYS | 43 | 5.621 | −1.042 | 2.550 | 1.00 | 0.00 |
| ATOM | 644 | O | CYS | 43 | 5.914 | −2.131 | 2.093 | 1.00 | 0.00 |
| ATOM | 645 | CB | CYS | 43 | 4.189 | 0.289 | 0.993 | 1.00 | 0.00 |
| ATOM | 646 | SG | CYS | 43 | 3.742 | 2.028 | 0.741 | 1.00 | 0.00 |
| ATOM | 647 | N | SER | 44 | 5.342 | −0.887 | 3.820 | 1.00 | 0.00 |
| ATOM | 648 | HN | SER | 44 | 5.111 | 0.002 | 4.163 | 1.00 | 0.00 |
| ATOM | 649 | CA | SER | 44 | 5.377 | −2.057 | 4.746 | 1.00 | 0.00 |
| ATOM | 650 | HA | SER | 44 | 5.988 | −2.837 | 4.317 | 1.00 | 0.00 |
| ATOM | 651 | CB | SER | 44 | 5.970 | −1.626 | 6.089 | 1.00 | 0.00 |
| ATOM | 652 | HB1 | SER | 44 | 7.044 | −1.758 | 6.065 | 1.00 | 0.00 |
| ATOM | 653 | HB2 | SER | 44 | 5.555 | −2.229 | 6.880 | 1.00 | 0.00 |
| ATOM | 654 | OG | SER | 44 | 5.652 | −0.261 | 6.327 | 1.00 | 0.00 |
| ATOM | 655 | HG | SER | 44 | 6.453 | 0.254 | 6.213 | 1.00 | 0.00 |
| ATOM | 656 | C | SER | 44 | 3.958 | −2.582 | 4.966 | 1.00 | 0.00 |
| ATOM | 657 | O | SER | 44 | 2.988 | −1.872 | 4.776 | 1.00 | 0.00 |
| ATOM | 658 | N | LEU | 45 | 3.831 | −3.821 | 5.374 | 1.00 | 0.00 |
| ATOM | 659 | HN | LEU | 45 | 4.633 | −4.366 | 5.523 | 1.00 | 0.00 |
| ATOM | 660 | CA | LEU | 45 | 2.479 | −4.408 | 5.619 | 1.00 | 0.00 |
| ATOM | 661 | HA | LEU | 45 | 1.902 | −4.381 | 4.707 | 1.00 | 0.00 |
| ATOM | 662 | CB | LEU | 45 | 2.642 | −5.866 | 6.086 | 1.00 | 0.00 |
| ATOM | 663 | HB1 | LEU | 45 | 2.210 | −5.981 | 7.070 | 1.00 | 0.00 |
| ATOM | 664 | HB2 | LEU | 45 | 3.693 | −6.109 | 6.130 | 1.00 | 0.00 |
| ATOM | 665 | CG | LEU | 45 | 1.940 | −6.828 | 5.113 | 1.00 | 0.00 |
| ATOM | 666 | HG | LEU | 45 | 2.092 | −7.842 | 5.453 | 1.00 | 0.00 |
| ATOM | 667 | CD1 | LEU | 45 | 0.437 | −6.533 | 5.085 | 1.00 | 0.00 |
| ATOM | 668 | HD11 | LEU | 45 | 0.254 | −5.543 | 5.475 | 1.00 | 0.00 |
| ATOM | 669 | HD12 | LEU | 45 | −0.083 | −7.259 | 5.692 | 1.00 | 0.00 |
| ATOM | 670 | HD13 | LEU | 45 | 0.074 | −6.591 | 4.068 | 1.00 | 0.00 |
| ATOM | 671 | CD2 | LEU | 45 | 2.530 | −6.674 | 3.700 | 1.00 | 0.00 |
| ATOM | 672 | HD21 | LEU | 45 | 1.731 | −6.619 | 2.977 | 1.00 | 0.00 |
| ATOM | 673 | HD22 | LEU | 45 | 3.154 | −7.528 | 3.478 | 1.00 | 0.00 |
| ATOM | 674 | HD23 | LEU | 45 | 3.126 | −5.774 | 3.650 | 1.00 | 0.00 |
| ATOM | 675 | C | LEU | 45 | 1.763 | −3.590 | 6.700 | 1.00 | 0.00 |
| ATOM | 676 | O | LEU | 45 | 0.555 | −3.464 | 6.698 | 1.00 | 0.00 |
| ATOM | 677 | N | TYR | 46 | 2.512 | −3.032 | 7.616 | 1.00 | 0.00 |
| ATOM | 678 | HN | TYR | 46 | 3.486 | −3.149 | 7.586 | 1.00 | 0.00 |
| ATOM | 679 | CA | TYR | 46 | 1.903 | −2.213 | 8.702 | 1.00 | 0.00 |
| ATOM | 680 | HA | TYR | 46 | 1.032 | −2.718 | 9.092 | 1.00 | 0.00 |
| ATOM | 681 | CB | TYR | 46 | 2.945 | −2.040 | 9.826 | 1.00 | 0.00 |
| ATOM | 682 | HB1 | TYR | 46 | 3.877 | −1.704 | 9.396 | 1.00 | 0.00 |
| ATOM | 683 | HB2 | TYR | 46 | 3.100 | −2.989 | 10.316 | 1.00 | 0.00 |
| ATOM | 684 | CG | TYR | 46 | 2.474 | −1.024 | 10.846 | 1.00 | 0.00 |
| ATOM | 685 | CD1 | TYR | 46 | 1.239 | −1.187 | 11.485 | 1.00 | 0.00 |
| ATOM | 686 | HD1 | TYR | 46 | 0.620 | −2.044 | 11.256 | 1.00 | 0.00 |
| ATOM | 687 | CD2 | TYR | 46 | 3.274 | 0.084 | 11.139 | 1.00 | 0.00 |
| ATOM | 688 | HD2 | TYR | 46 | 4.228 | 0.205 | 10.644 | 1.00 | 0.00 |
| ATOM | 689 | CE1 | TYR | 46 | 0.806 | −0.239 | 12.419 | 1.00 | 0.00 |
| ATOM | 690 | HE1 | TYR | 46 | −0.147 | −0.362 | 12.913 | 1.00 | 0.00 |
| ATOM | 691 | CE2 | TYR | 46 | 2.843 | 1.031 | 12.074 | 1.00 | 0.00 |
| ATOM | 692 | HE2 | TYR | 46 | 3.462 | 1.886 | 12.298 | 1.00 | 0.00 |
| ATOM | 693 | CZ | TYR | 46 | 1.608 | 0.871 | 12.714 | 1.00 | 0.00 |

TABLE 4-continued

Atomic coordinates of Asp$^{28}$IP(AspGlyLys) in PDB format

| ATOM | 694 | OH | TYR | 46 | 1.182 | 1.807 | 13.635 | 1.00 | 0.00 |
|---|---|---|---|---|---|---|---|---|---|
| ATOM | 695 | HH | TYR | 46 | 1.440 | 2.676 | 13.317 | 1.00 | 0.00 |
| ATOM | 696 | C | TYR | 46 | 1.489 | −0.848 | 8.130 | 1.00 | 0.00 |
| ATOM | 697 | O | TYR | 46 | 0.498 | −0.273 | 8.537 | 1.00 | 0.00 |
| ATOM | 698 | N | GLN | 47 | 2.250 | −0.329 | 7.202 | 1.00 | 0.00 |
| ATOM | 699 | HN | GLN | 47 | 3.049 | −0.812 | 6.900 | 1.00 | 0.00 |
| ATOM | 700 | CA | GLN | 47 | 1.917 | 0.999 | 6.609 | 1.00 | 0.00 |
| ATOM | 701 | HA | GLN | 47 | 1.816 | 1.727 | 7.398 | 1.00 | 0.00 |
| ATOM | 702 | CB | GLN | 47 | 3.037 | 1.432 | 5.663 | 1.00 | 0.00 |
| ATOM | 703 | HB1 | GLN | 47 | 2.649 | 2.158 | 4.965 | 1.00 | 0.00 |
| ATOM | 704 | HB2 | GLN | 47 | 3.403 | 0.573 | 5.123 | 1.00 | 0.00 |
| ATOM | 705 | CG | GLN | 47 | 4.180 | 2.060 | 6.463 | 1.00 | 0.00 |
| ATOM | 706 | HG1 | GLN | 47 | 5.107 | 1.930 | 5.927 | 1.00 | 0.00 |
| ATOM | 707 | HG2 | GLN | 47 | 4.251 | 1.582 | 7.429 | 1.00 | 0.00 |
| ATOM | 708 | CD | GLN | 47 | 3.908 | 3.555 | 6.649 | 1.00 | 0.00 |
| ATOM | 709 | OE1 | GLN | 47 | 2.774 | 3.961 | 6.811 | 1.00 | 0.00 |
| ATOM | 710 | NE2 | GLN | 47 | 4.907 | 4.396 | 6.632 | 1.00 | 0.00 |
| ATOM | 711 | HE21 | GLN | 47 | 5.821 | 4.070 | 6.501 | 1.00 | 0.00 |
| ATOM | 712 | HE22 | GLN | 47 | 4.740 | 5.355 | 6.751 | 1.00 | 0.00 |
| ATOM | 713 | C | GLN | 47 | 0.606 | 0.914 | 5.822 | 1.00 | 0.00 |
| ATOM | 714 | O | GLN | 47 | −0.167 | 1.855 | 5.797 | 1.00 | 0.00 |
| ATOM | 715 | N | LEU | 48 | 0.356 | −0.193 | 5.164 | 1.00 | 0.00 |
| ATOM | 716 | HN | LEU | 48 | 0.999 | −0.932 | 5.186 | 1.00 | 0.00 |
| ATOM | 717 | CA | LEU | 48 | −0.898 | −0.317 | 4.361 | 1.00 | 0.00 |
| ATOM | 718 | HA | LEU | 48 | −1.178 | 0.661 | 4.011 | 1.00 | 0.00 |
| ATOM | 719 | CB | LEU | 48 | −0.653 | −1.227 | 3.151 | 1.00 | 0.00 |
| ATOM | 720 | HB1 | LEU | 48 | −1.599 | −1.466 | 2.688 | 1.00 | 0.00 |
| ATOM | 721 | HB2 | LEU | 48 | −0.178 | −2.139 | 3.482 | 1.00 | 0.00 |
| ATOM | 722 | CG | LEU | 48 | 0.250 | −0.524 | 2.127 | 1.00 | 0.00 |
| ATOM | 723 | HG | LEU | 48 | 1.213 | −0.323 | 2.575 | 1.00 | 0.00 |
| ATOM | 724 | CD1 | LEU | 48 | 0.434 | −1.434 | 0.914 | 1.00 | 0.00 |
| ATOM | 725 | HD11 | LEU | 48 | −0.381 | −1.278 | 0.222 | 1.00 | 0.00 |
| ATOM | 726 | HD12 | LEU | 48 | 0.441 | −2.465 | 1.236 | 1.00 | 0.00 |
| ATOM | 727 | HD13 | LEU | 48 | 1.369 | −1.202 | 0.427 | 1.00 | 0.00 |
| ATOM | 728 | CD2 | LEU | 48 | −0.391 | 0.793 | 1.667 | 1.00 | 0.00 |
| ATOM | 729 | HD21 | LEU | 48 | −0.293 | 1.532 | 2.447 | 1.00 | 0.00 |
| ATOM | 730 | HD22 | LEU | 48 | −1.437 | 0.629 | 1.455 | 1.00 | 0.00 |
| ATOM | 731 | HD23 | LEU | 48 | 0.108 | 1.143 | 0.775 | 1.00 | 0.00 |
| ATOM | 732 | C | LEU | 48 | −2.047 | −0.892 | 5.201 | 1.00 | 0.00 |
| ATOM | 733 | O | LEU | 48 | −3.135 | −1.097 | 4.695 | 1.00 | 0.00 |
| ATOM | 734 | N | GLU | 49 | −1.832 | −1.150 | 6.468 | 1.00 | 0.00 |
| ATOM | 735 | HN | GLU | 49 | −0.954 | −0.979 | 6.864 | 1.00 | 0.00 |
| ATOM | 736 | CA | GLU | 49 | −2.930 | −1.700 | 7.315 | 1.00 | 0.00 |
| ATOM | 737 | HA | GLU | 49 | −3.371 | −2.553 | 6.822 | 1.00 | 0.00 |
| ATOM | 738 | CB | GLU | 49 | −2.361 | −2.134 | 8.669 | 1.00 | 0.00 |
| ATOM | 739 | HB1 | GLU | 49 | −3.148 | −2.130 | 9.407 | 1.00 | 0.00 |
| ATOM | 740 | HB2 | GLU | 49 | −1.583 | −1.445 | 8.968 | 1.00 | 0.00 |
| ATOM | 741 | CG | GLU | 49 | −1.773 | −3.547 | 8.552 | 1.00 | 0.00 |
| ATOM | 742 | HG1 | GLU | 49 | −0.698 | −3.485 | 8.536 | 1.00 | 0.00 |
| ATOM | 743 | HG2 | GLU | 49 | −2.119 | −4.009 | 7.640 | 1.00 | 0.00 |
| ATOM | 744 | CD | GLU | 49 | −2.211 | −4.392 | 9.751 | 1.00 | 0.00 |
| ATOM | 745 | OE1 | GLU | 49 | −2.509 | −5.558 | 9.550 | 1.00 | 0.00 |
| ATOM | 746 | OE2 | GLU | 49 | −2.237 | −3.860 | 10.848 | 1.00 | 0.00 |
| ATOM | 747 | C | GLU | 49 | −4.006 | −0.631 | 7.530 | 1.00 | 0.00 |
| ATOM | 748 | O | GLU | 49 | −5.146 | −0.942 | 7.823 | 1.00 | 0.00 |
| ATOM | 749 | N | ASN | 50 | −3.655 | 0.624 | 7.393 | 1.00 | 0.00 |
| ATOM | 750 | HN | ASN | 50 | −2.730 | 0.851 | 7.163 | 1.00 | 0.00 |
| ATOM | 751 | CA | ASN | 50 | −4.655 | 1.714 | 7.596 | 1.00 | 0.00 |
| ATOM | 752 | HA | ASN | 50 | −5.281 | 1.470 | 8.441 | 1.00 | 0.00 |
| ATOM | 753 | CB | ASN | 50 | −3.919 | 3.024 | 7.881 | 1.00 | 0.00 |
| ATOM | 754 | HB1 | ASN | 50 | −4.525 | 3.856 | 7.552 | 1.00 | 0.00 |
| ATOM | 755 | HB2 | ASN | 50 | −2.979 | 3.032 | 7.348 | 1.00 | 0.00 |
| ATOM | 756 | CG | ASN | 50 | −3.657 | 3.151 | 9.383 | 1.00 | 0.00 |
| ATOM | 757 | OD1 | ASN | 50 | −4.068 | 4.112 | 10.004 | 1.00 | 0.00 |
| ATOM | 758 | ND2 | ASN | 50 | −2.983 | 2.218 | 9.997 | 1.00 | 0.00 |
| ATOM | 759 | HD21 | ASN | 50 | −2.650 | 1.444 | 9.497 | 1.00 | 0.00 |
| ATOM | 760 | HD22 | ASN | 50 | −2.810 | 2.291 | 10.959 | 1.00 | 0.00 |
| ATOM | 761 | C | ASN | 50 | −5.538 | 1.894 | 6.347 | 1.00 | 0.00 |
| ATOM | 762 | O | ASN | 50 | −6.396 | 2.757 | 6.321 | 1.00 | 0.00 |
| ATOM | 763 | N | TYR | 51 | −5.342 | 1.102 | 5.313 | 1.00 | 0.00 |
| ATOM | 764 | HN | TYR | 51 | −4.649 | 0.413 | 5.342 | 1.00 | 0.00 |
| ATOM | 765 | CA | TYR | 51 | −6.184 | 1.260 | 4.086 | 1.00 | 0.00 |
| ATOM | 766 | HA | TYR | 51 | −6.744 | 2.180 | 4.159 | 1.00 | 0.00 |
| ATOM | 767 | CB | TYR | 51 | −5.293 | 1.305 | 2.838 | 1.00 | 0.00 |
| ATOM | 768 | HB1 | TYR | 51 | −5.911 | 1.234 | 1.956 | 1.00 | 0.00 |
| ATOM | 769 | HB2 | TYR | 51 | −4.601 | 0.476 | 2.860 | 1.00 | 0.00 |
| ATOM | 770 | CG | TYR | 51 | −4.525 | 2.597 | 2.799 | 1.00 | 0.00 |

TABLE 4-continued

Atomic coordinates of Asp$^{28}$IP(AspGlyLys) in PDB format

| ATOM | 771 | CD1 | TYR | 51 | −5.154 | 3.766 | 2.364 | 1.00 | 0.00 |
|------|-----|-----|-----|----|--------|-------|-------|------|------|
| ATOM | 772 | HD1 | TYR | 51 | −6.189 | 3.738 | 2.061 | 1.00 | 0.00 |
| ATOM | 773 | CD2 | TYR | 51 | −3.187 | 2.625 | 3.189 | 1.00 | 0.00 |
| ATOM | 774 | HD2 | TYR | 51 | −2.706 | 1.719 | 3.518 | 1.00 | 0.00 |
| ATOM | 775 | CE1 | TYR | 51 | −4.442 | 4.970 | 2.323 | 1.00 | 0.00 |
| ATOM | 776 | HE1 | TYR | 51 | −4.924 | 5.873 | 1.980 | 1.00 | 0.00 |
| ATOM | 777 | CE2 | TYR | 51 | −2.470 | 3.824 | 3.147 | 1.00 | 0.00 |
| ATOM | 778 | HE2 | TYR | 51 | −1.435 | 3.843 | 3.448 | 1.00 | 0.00 |
| ATOM | 779 | CZ  | TYR | 51 | −3.098 | 4.998 | 2.716 | 1.00 | 0.00 |
| ATOM | 780 | OH  | TYR | 51 | −2.392 | 6.183 | 2.678 | 1.00 | 0.00 |
| ATOM | 781 | HH  | TYR | 51 | −2.342 | 6.527 | 3.574 | 1.00 | 0.00 |
| ATOM | 782 | C   | TYR | 51 | −7.163 | 0.085 | 3.961 | 1.00 | 0.00 |
| ATOM | 783 | O   | TYR | 51 | −7.191 | −0.606 | 2.958 | 1.00 | 0.00 |
| ATOM | 784 | N   | CYS | 52 | −7.969 | −0.146 | 4.964 | 1.00 | 0.00 |
| ATOM | 785 | HN  | CYS | 52 | −7.933 | 0.419 | 5.764 | 1.00 | 0.00 |
| ATOM | 786 | CA  | CYS | 52 | −8.945 | −1.273 | 4.885 | 1.00 | 0.00 |
| ATOM | 787 | HA  | CYS | 52 | −9.067 | −1.561 | 3.852 | 1.00 | 0.00 |
| ATOM | 788 | HB1 | CYS | 52 | −9.205 | −3.211 | 5.770 | 1.00 | 0.00 |
| ATOM | 789 | HB2 | CYS | 52 | −8.165 | −2.127 | 6.692 | 1.00 | 0.00 |
| ATOM | 790 | C   | CYS | 52 | −10.299 | −0.835 | 5.445 | 1.00 | 0.00 |
| ATOM | 791 | O   | CYS | 52 | −10.402 | 0.139 | 6.168 | 1.00 | 0.00 |
| ATOM | 792 | CB  | CYS | 52 | −8.430 | −2.462 | 5.700 | 1.00 | 0.00 |
| ATOM | 793 | SG  | CYS | 52 | −6.973 | −3.180 | 4.902 | 1.00 | 0.00 |
| ATOM | 794 | N   | ASN | 53 | −11.337 | −1.559 | 5.114 | 1.00 | 0.00 |
| ATOM | 795 | HN  | ASN | 53 | −11.218 | −2.339 | 4.531 | 1.00 | 0.00 |
| ATOM | 796 | CA  | ASN | 53 | −12.699 | −1.212 | 5.617 | 1.00 | 0.00 |
| ATOM | 797 | HA  | ASN | 53 | −12.919 | −0.183 | 5.382 | 1.00 | 0.00 |
| ATOM | 798 | CB  | ASN | 53 | −13.733 | −2.121 | 4.950 | 1.00 | 0.00 |
| ATOM | 799 | HB1 | ASN | 53 | −14.565 | −2.272 | 5.621 | 1.00 | 0.00 |
| ATOM | 800 | HB2 | ASN | 53 | −13.279 | −3.074 | 4.721 | 1.00 | 0.00 |
| ATOM | 801 | CG  | ASN | 53 | −14.234 | −1.471 | 3.658 | 1.00 | 0.00 |
| ATOM | 802 | OD1 | ASN | 53 | −13.551 | −0.657 | 3.069 | 1.00 | 0.00 |
| ATOM | 803 | ND2 | ASN | 53 | −15.407 | −1.800 | 3.192 | 1.00 | 0.00 |
| ATOM | 804 | HD21 | ASN | 53 | −15.958 | −2.456 | 3.669 | 1.00 | 0.00 |
| ATOM | 805 | HD22 | ASN | 53 | −15.737 | −1.391 | 2.364 | 1.00 | 0.00 |
| ATOM | 806 | C   | ASN | 53 | −12.750 | −1.410 | 7.133 | 1.00 | 0.00 |
| ATOM | 807 | OT1 | ASN | 53 | −12.763 | −2.553 | 7.560 | 1.00 | 0.00 |
| ATOM | 808 | OT2 | ASN | 53 | −12.775 | −0.416 | 7.840 | 1.00 | 0.00 |
| END  |     |     |     |    |        |       |       |      |      |

Example 3

The insulin analogue precursor Asp$^{B28}$IP(AspGlyLys) was produced culturing yeast strain MT663 transformed with an expression plasmid expressing either a YAP3-TA39-EEGEPK(SEQ ID NO:8)-Asp$^{B28}$IP(DGK) fusion protein or a YAP3-TA57-EEGEPK(SEQ ID NO:8)-Asp$^{B28}$IP(DGK) fusion protein. TA39 is a pro-sequence QPIDDTESNTTSVNLMADDT-ESRFATNTTLAGGL-DVVNLISMAKR(SEQ ID NO: 15). The sequence EEGEPK(SEQ ID NO:8) is an N-terminal extension to the B-chain of the insulin analogue. TA57 is a pro-sequence QPIDDTESQTTSVNLMADDTESAFATQTNSGGLDV-VGLISMAKR (SEQ ID NO:16). cDNA encoding the leader sequences YAP3-TA39 and YAP3-TA57 and cDNA encoding the Asp$^{B28}$IP(DGK) and the N-terminal extension were cloned into an expression vector of the C-POT type using standard techniques (Sambrook J, Fritsch E F and Maniatis T, Molecular cloning, Cold spring Harbour laboratory press, 1989). The DNA and inferred amino acids sequences are shown in FIG. 7 (SEQ ID NO:9 and 10) and FIG. 8 (SEQ ID NO:11 and 12).

Table 5 shows the yields. Fermentation was conducted at 30° C. for 72 h in 5 ml YPD. IP yield was determined by RP-HPLC of the culture supernatant and is expressed relative to the IP yield of the strain yJB155.

TABLE 5

| Leader | Precursor | N-terminal extension | C-peptide | Yield* | SEQ ID |
|--------|-----------|----------------------|-----------|--------|--------|
| α*-ex4 | Asp$^{B28}$IP | GluGluAlaGluAlaGlu-AlaProLys | None | 100 | SEQ ID NO:3 |
| YAP3-TA39 | Asp$^{B28}$IP | GluGluGlyGluProLys | AspGlyLys | 477% | SEQ ID NO:8 |
| YAP3-TA57 | Asp$^{B28}$IP | GluGluGlyGluProLys | AspGlyLys | 306% | SEQ ID NO:8 |

Example 4

Construction of Human Insulin Precursors with Synthetic C-peptides with a Glycine Residue Synthetic genes encoding fusion proteins consisting of the insulin precursor associated with a leader sequence consisting of a pre-peptide (signal peptide) and a pro-peptide, were constructed using PCR under standard conditions (Sambrook et al. (1989) Molecular Cloning, Cold Spring Harbor Laboratory Press) and E.H.F. polymerase (Boehringer Mannheim GmbH, Sandhoefer Strasse 116, Mannheim, Germany). The resulting DNA fragments were isolated and digested with endonucleases and purified using the Gene Clean kit (Bio101 Inc., La Jolla, Calif., USA). Standard methods were used for DNA ligation and transformation of E. coli cells were performed by the CaCl$_2$ method (Sambrook et al. (1989) supra). Plasmids were purified from transformed E. coli cells using QIAGEN columns (QIAGEN, Hilden, Germany). Nucleotide sequences were determined using the ALF Pharmacia Biotech DNA sequencing system with purified double-stranded plasmid DNA as template. Oligonucleotide primers for PCR were obtained from DNA technology (Arhus, Denmark).

Secretion of the insulin precursor was facilitated by the TA57 leader (Kjeldsen et al., 1998. Protein Expression al. (1987) in "Peptides 1986" (Theodoropoulos, D., Ed.), pp. 189–194, Walter de Gruyter & Co., Berlin.).

Development of synthetic mini C-peptides was performed by randomization of one or more codon(s) encoding the amino acids in the mini C-peptide. The synthetic mini C-peptides feature typically an enzymatic processing site (Lys) at the C-terminus which allows enzymatic removal of the synthetic mini C-peptide. Randomization was performed using doped oligonucleotides which introduced codon(s) variations at one or more positions of the synthetic mini C-peptides. Typically one of the two primers (oligonucleotides) used for PCR was doped. Examples of primers are:

```
Primer A: 5'-TTGCTTAAATCTATAACTAC-3'                                         (SEQ ID NO: 19)

Primer B: 5'-TTAGTTTCTAGACTAGTTGCAGTAGTTTTCCAATTGGTACAAGGAGCAGATGGA- (SEQ ID NO: 20)
          GGTACAGCATTGTTCGACAATACCCTTACCMNNCTTAGGAGTGTAGAAGAAACC-3'
N = ACTG, M = GT
```

Purif. 14, 309–316), although a variety of known yeast leader sequences may be used.

Figure 9:
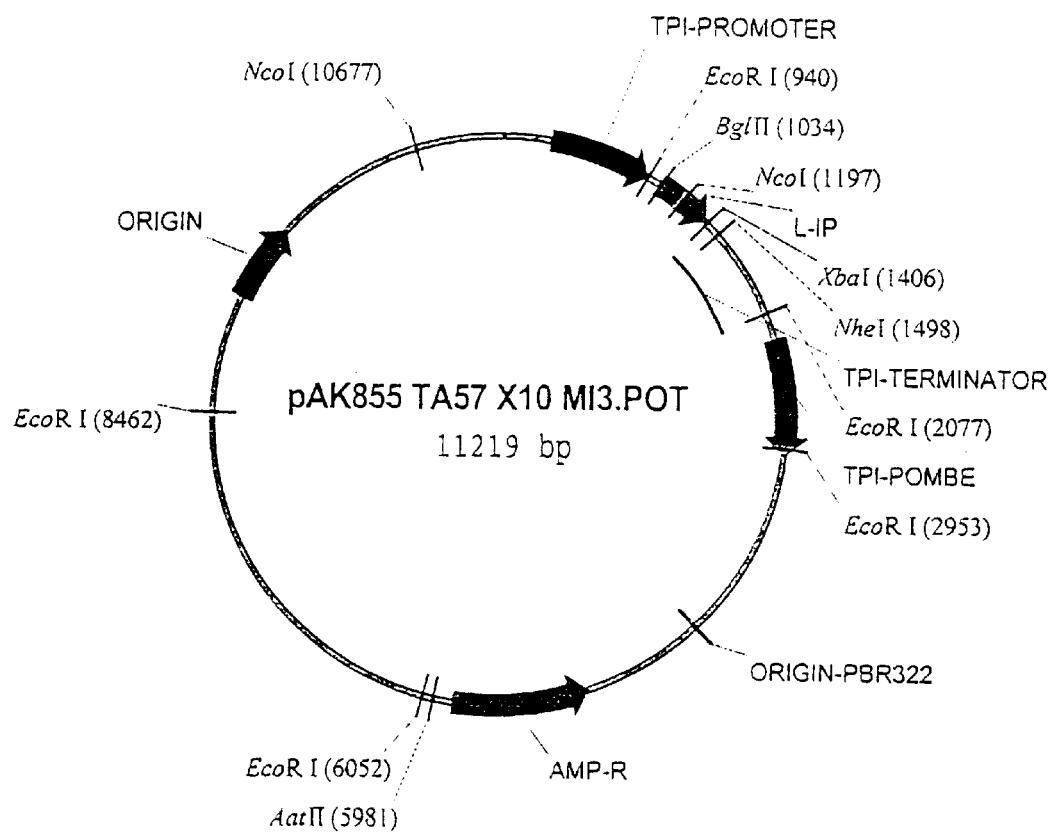
FIG. 9 represents the pAK855 S. cerevisiae expression plasmid expressing the TA57 leader-GluGluGlyGluProLys SEQ ID NO:8)-B(1–29)-AlaAlaLys-A(1–21) precursor and FIG. 10. represents the nucleotide sequence of the expression cassette of the pAK855 yeast expression plasmid and the inferred amino acid sequence (SEQ ID NO: 17 and 18).

As shown in FIGS. 9 and 10, the pAK855 S. cerevisiae expression plasmid expressing the TA57 leader-GluGluGlyGluProLys(SEQ ID NO:8)-insulin precursor fusion protein was constructed based on the S. cerevisiae-E. coli shuttle POT plasmid (U.S. Pat. No. 5,871,957). L-IP indicates the fusion protein expression cassette encoding the leader-insulin precursor fusion protein, TPI-PROMOTER is the S. cerevisiae TPI1 promoter and TPI-TERMINATOR is the S. cerevisiae TPI1 terminator; TPI-POMBE indicates the S. pombe POT gene used for selection in S. cerevisiae; ORIGIN indicates a S. cerevisiae origin of replication derived from the 2 µm plasmid; AMP-R indicates the β-lactamase gene conferring resistance toward ampicillin, facilitating selection in E. coli and ORIGIN-PBR322 indicates an E. coli origin of replication.

DNA encoding a number of fusions proteins of leader sequences and insulin precursors with different mini C-peptides was generated by PCR using appropriate oligonucleotides as primers, as described below. Standard methods were used to subclone DNA fragments encoding the leader-insulin precursor fusion proteins into the CPOT expression vector in the following configuration: leader-Lys-Arg-spacer-insulin precursor, where Lys-Arg is a potential dibasic endoprotease processing site and spacer is an N-terminal extension. To optimize processing of the fusion protein by the S. cerevisiae Kex2 endoprotease, DNA encoding a spacer peptide (N-terminal extension), e.g. GluGluGlyGluPro-Lys (SEQ ID NO:8) was inserted between the DNA encoding the leader and the insulin precursor (Kjeldsen et al. (1999b.) J. Biotechnology, 75 195–208). However, the present of the spacer peptide is not mandatory. The insulin precursor was secreted as a single-chain N-terminally extended insulin precursor with a mini C-peptide, connecting Lys$^{B29}$ and Gly$^{A1}$. After purification of the insulin precursor and proteolytic removal of the N-terminal extension and the mini C-peptide, the amino acid Thr$^{B30}$ can be added to Lys$^{B29}$ by enzyme-mediated transpeptidation, to generate human insulin (Markussen, et PCR was typically performed as indicated below: 5 µl Primer A (20 pmol), 5 µl Primer B (20 pmol), 10 µl 10×PCR buffer, 8 µl dNTP mix, 0.75 µl E.H.F. enzyme, 1 µl pAK885 plasmid as template (approximately 0.2 µg DNA), and 70.25 µl distilled water.

Typically between 10 and 15 cycles were performed, one cycle typically was 95° C. for 45 sec.; 55° C. for 1 min; 72° C. for 1.5 min. The PCR mixture was subsequently loaded onto an 2% agarose gel and electrophoresis was performed using standard techniques. The resulting DNA fragment was cut out of the agarose gel and isolated by the Gene Clean kit.

FIG. 9 shows the nucleotide sequence of the pAK855 DNA expression cassette used as template for PCR and inferred amino acids of the encoded fusion protein (TA57-leader-EEGEPK(SEQ ID NO:8)-insulin precursor of pAK855 (SEQ ID NO:17 and 18).

The purified PCR DNA fragment was dissolved in water and restriction endonucleases buffer and digested with suitable restriction endonucleases (e.g. Bgl II and Xba I) according to standard techniques. The BglII-XbaI DNA fragments were subjected to agarose electrophoresis and purified using The Gene Clean Kit. The digested and isolated DNA fragments were ligated together with a suitable vector (e.g. of the CPOT type) using T4 DNA ligase and standard conditions. The ligation mix was subsequently transformed into a competent E. coli strain (R–, M+) followed by selection with ampicillin resistance. Plasmids from the resulting E. coli's were isolated using QIAGEN columns.

The plasmids were subsequently used for transformation of a suitable S. cerevisiae strainMT663 (MATα/MATα pep4-3/pep4-3 HIS4/his4 tpi::LEU2/tpi::LEU2 Cir$^+$). Individual transformed S. cerevisiae clones were grown in liquid culture, and the quantity of secreted insulin precursor the culture supernatants was determined by RP-HPLC. The DNA sequence encoding the synthetic mini C-peptide of the expression plasmids from S. cerevisiae clones secreting increased quantity of the insulin precursor were then determined.

Table 6 shows the insulin precursors generated by the above method and production yield expressed as a percent of control. Fermentation was conducted at 30° C. for 72 h in 5 ml YPD. Yield of the insulin precursor was determined by RP-HPLC of the culture supernatant, and is expressed relative to the yield of a control strain expressing a leader-insulin precursor fusion protein in which the B29 residue is linked to the A1 residue by a mini C-peptide Ala-Ala-Lys. YAP3 is the YAP3 signal sequence. The sequence EEGEPK (SEQ ID NO:8) is an N-terminal extension to the B-chain and TA57 is a synthetic pro-sequence QPIDDTESQTTS-VNLMADDTESAFATQTNSGGLDVVGLISMAKR (SEQ ID NO:16).

TABLE 6

| Leader | N-terminal extension | C-peptide | Yield* | SEQ ID |
|---|---|---|---|---|
| YAP3-TA57 | GluGluGlyGluProLys | AlaAlaLys Control | 100 | SEQ ID NO:2 |
| YAP3-TA57 | GluGluGlyGluProLys | AspGlyLys | 185 | SEQ ID NO:2 |
| YAP3-TA57 | GluGluGlyGluProLys | GluGlyLys | 153 | SEQ ID NO:2 |

What is claimed is:

1. An insulin precursor or insulin analog precursor comprising a sequence of formula I:

B(1–27)—$X_3$—$X_2$—$X_1$—Y—A(1–21), wherein $X_1$ is a sequence comprising a Gly immediately N-terminal to Y, $X_2$ is one of Pro, Lys, Ala, Arg or Pro-Thr at position 29 of the B chain, $X_3$ is one of Pro, Asp, Lys, or Ile at position 28 of the B chain, and Y is Lys or Arg.

2. An insulin precursor or an insulin analog precursor according to claim 1, wherein $X_1$ is 1–15 amino acid residues in length.

3. An insulin precursor or an insulin analog precursor according to claim 1, wherein $X_1$ is 1–10 amino acid residues in length.

4. An insulin precursor or an insulin analog precursor according to claim 1, wherein $X_1$ is 1–8 amino acid residues in length.

5. An insulin precursor or an insulin analog precursor according to claim 1, wherein $X_1$ is 1–5 amino acid residues in length.

6. An insulin precursor or an insulin analog precursor according to claim 1, wherein $X_1$ is 1–3 amino acid residues in length.

7. An insulin precursor or an insulin analog precursor according to claim 1, wherein $X_1$ contains 1–5 Gly.

8. An insulin precursor or an insulin analog precursor according to claim 1, wherein $X_1$ contains 1–3 Gly.

9. An insulin precursor or an insulin analog precursor according to claim 1, wherein $X_3$ is Asp and $X_2$ is Lys.

10. An insulin precursor or an insulin analog precursor according to claim 1, wherein $X_1$—Y is selected from the group of: (a) Glu-Glu-Gly-Lys(SEQ ID NO:1) (b) Glu-Gly-Lys, (c) Ser-Gly-Lys, (d) Asn-Gly-Lys, (e) Thr-Gly-Lys, (f) Asp-Gly-Lys, (g) Met-Gly-Lys, (h) Ala-Gly-Lys, (i) His-Gly-Lys and (j) Gly-Lys.

11. An insulin precursor or insulin analog precursor according to claim 1, wherein the B27 (atom CG2) has a proximity to the A1 (atom CA) of less than 5 Å.

12. A polynucleotide sequence encoding an insulin precursor or an insulin analog precursor according to claim 1.

13. An expression vector comprising a polynucleotide sequence according to claim 12.

14. A host cell transformed with the vector of claim 13.

15. A process for making an insulin precursor or an insulin analog precursor, said method comprising (i) culturing a host comprising a polynucleotide sequence according to claim 12 under suitble culture conditions for expression of said precursor; and (ii) isolating the expressed precursor.

16. A process according to claim 15, wherein the host cell is a yeast host cell.

17. A process according to claim 15, further comprising (iii) converting the precursor into insulin or an insulin analog by in vitro chemical or enzymatic conversion.

18. An insulin precursor or insulin analog precursor comprising a connecting peptide (C-peptide) being cleavable from the A and B chains said connecting peptide comprising at least one Gly and a cleavage site enabling cleavage of the peptide bond between the A-chain and the connecting peptide, wherein (i) one Gly is immediately N-terminal to said cleavage site and (ii) said connecting peptide does not contain two adjacent basic amino acids.

19. An insulin precursor or insulin analog precursor according to claim 18, wherein the connecting pepride is 1–15 amino acid residues in length.

20. An insulin precursor or insulin analog precursor according to claim 18, wherein the connecting peptide is 1–10 amino acid residues in length.

21. An insulin precursor or insulin analog precursor according to claim 18, wherein the connecting peptide is 1–9 amino acid residues in length.

22. An insulin precursor or insulin analog precursor according to claim 18, wherein the connecting peptide is 1–5 amino acid residues in length.

23. An insulin precursor or insulin analog precursor according to claim 18, wherein the connecting peptide is 1–3 amino acid residues in length.

24. An insulin precursor or insulin analog precursor according to claim 18, wherein the B27 (atom CG2) has a proximity to the A1 (atom CA) of less than 5 Å.

25. An insulin precursor or insulin analog precursor according to claim 18, wherein the connecting peptide contains 1–5 Gly.

26. An insulin precursor or insulin analog precursor according to claim 18, wherein the connecting peptide contains 1–3 Gly.

27. A polynucleotide sequence encoding an insulin precursor or an insulin analog precursor according to claim 18.

28. An expression vector comprising a polynucleotide sequence according to claim 27.

29. A host cell transformed with the vector of claim 28.

30. A process for making an insulin precursor or an insulin analog precursor, said method comprising (i) culturing a host cell comprising a polynucleotide sequence according to claim 27 under suitable culture conditions for expression of said precursor; and (ii) isolating the expressed precursor.

31. A process according to claim 30, wherein the host cell is a yeast host cell.

32. A process according to claim 30, further comprising (iii) converting the precursor into insulin or an insulin analog by in vitro chemical or enzymatic conversion.

* * * * *

SEQUENCE LISTING

<160> NUMBER OF SEQ ID NOS: 20

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Glu Glu Gly Lys
 1

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Glu Glu Ala Glu Ala Glu Ala Glu Pro Lys
 1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Glu Glu Ala Glu Ala Glu Ala Glu Pro Lys
 1               5                   10

<210> SEQ ID NO 4
<211> LENGTH: 600
<212> TYPE: DNA
<213> ORGANISM: Artificial Sequence
<220> FEATURE:
<221> NAME/KEY: CDS
<222> LOCATION: (114)...(554)
<223> OTHER INFORMATION: Synthetic

<400> SEQUENCE: 4

```
tcttgcttaa atctataact acaaaaaaca catacaggaa ttccattcaa gatctgttca      60
aacaagaaga ttacaaacta tcaatttcat acacaatata aacgattaaa aga atg       116
                                                             Met
                                                              1
```

```
aga ttt cct tca att ttt act gca gtt tta ttc gca tcc tcc gca      164
Arg Phe Pro Ser Ile Phe Thr Ala Val Leu Phe Ala Ala Ser Ser Ala
        5                  10                  15 tta gct gct cca gtc aac act aca aca gaa gat gaa acg gca caa att  212
Leu Ala Ala Pro Val Asn Thr Thr Thr Glu Asp Glu Thr Ala Gln Ile
         20                  25                  30 ccg gct gaa gct gtc atc ggt tac tca gat tta gaa ggg gat ttc gat  260
Pro Ala Glu Ala Val Ile Gly Tyr Ser Asp Leu Glu Gly Asp Phe Asp
 35                  40                  45 gtt gct gtt ttg cca ttt tcc aac agc aca aat aac ggg tta ttg ttt  308
Val Ala Val Leu Pro Phe Ser Asn Ser Thr Asn Asn Gly Leu Leu Phe
 50                  55                  60                  65 ata aat act act att gcc agc att gct gct aaa gaa gaa ggg gta tcc  356
Ile Asn Thr Thr Ile Ala Ser Ile Ala Ala Lys Glu Glu Gly Val Ser
                 70                  75                  80 atg gct aag aga gaa gaa gct gaa gct gaa gct cca aag ttc gtt aac  404
Met Ala Lys Arg Glu Glu Ala Glu Ala Glu Ala Pro Lys Phe Val Asn
             85                  90                  95 caa cac ttg tgt ggt tct cac ttg gtt gaa gct ttg tac ttg gtt tgt  452
Gln His Leu Cys Gly Ser His Leu Val Glu Ala Leu Tyr Leu Val Cys
         100                 105                 110 ggt gaa aga ggt ttc ttc tac act gac aag ggt atc gtt gaa caa tgt  500
Gly Glu Arg Gly Phe Phe Tyr Thr Asp Lys Gly Ile Val Glu Gln Cys
     115                 120                 125 tgt act tct atc tgt tct ttg tac caa ttg gaa aac tac tgt aac tag  548
Cys Thr Ser Ile Cys Ser Leu Tyr Gln Leu Glu Asn Tyr Cys Asn *
130             135                 140 acg cag cccgcaggct ctagaaacta agattaatat aattatataa aaatat        600
Thr Gln
145
```

<210> SEQ ID NO 5
<211> LENGTH: 146
<212> TYPE: PRT
<213> ORGANISM: Artificial Sequence
<220> FEATURE:
<223> OTHER INFORMATION: Synthetic

<400> SEQUENCE: 5

```
Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
 65                  70                  75                  80

Ser Met Ala Lys Arg Glu Glu Ala Glu Ala Glu Ala Pro Lys Phe Val
                 85                  90                  95

Asn Gln His Leu Cys Gly Ser His Leu Val Glu Ala Leu Tyr Leu Val
             100                 105                 110

Cys Gly Glu Arg Gly Phe Phe Tyr Thr Asp Lys Gly Ile Val Glu Gln
         115                 120                 125

Cys Cys Thr Ser Ile Cys Ser Leu Tyr Gln Leu Glu Asn Tyr Cys Asn
     130                 135                 140

Thr Gln
145
```

<210> SEQ ID NO 6
<211> LENGTH: 600
<212> TYPE: DNA
<213> ORGANISM: Artificial Sequence
<220> FEATURE:
<221> NAME/KEY: CDS
<222> LOCATION: (114)...(545)
<223> OTHER INFORMATION: Synthetic

<400> SEQUENCE: 6

```
tcttgcttaa atctataact acaaaaaaca catacaggaa ttccattcaa gatctgttca      60
aacaagaaga ttacaaacta tcaatttcat acacaatata aacgattaaa aga atg       116
                                                              Met
                                                               1 aga ttt cct tca att ttt act gca gtt tta ttc gca gca tcc tcc gca      164
Arg Phe Pro Ser Ile Phe Thr Ala Val Leu Phe Ala Ala Ser Ser Ala
                5                  10                  15 tta gct gct cca gtc aac act aca aca gaa gat gaa acg gca caa att      212
Leu Ala Ala Pro Val Asn Thr Thr Thr Glu Asp Glu Thr Ala Gln Ile
         20                  25                  30 ccg gct gaa gct gtc atc ggt tac tca gat tta gaa ggg gat ttc gat      260
Pro Ala Glu Ala Val Ile Gly Tyr Ser Asp Leu Glu Gly Asp Phe Asp
     35                  40                  45 gtt gct gtt ttg cca ttt tcc aac agc aca aat aac ggg tta ttg ttt      308
Val Ala Val Leu Pro Phe Ser Asn Ser Thr Asn Asn Gly Leu Leu Phe
 50                  55                  60                  65 ata aat act act att gcc agc att gct gct aaa gaa gaa ggg gta tcc      356
Ile Asn Thr Thr Ile Ala Ser Ile Ala Ala Lys Glu Glu Gly Val Ser
                 70                  75                  80 atg gct aag aga gaa gaa gct gaa gct gaa gct cca aag ttc gtt aac      404
Met Ala Lys Arg Glu Glu Ala Glu Ala Glu Ala Pro Lys Phe Val Asn
                85                  90                  95 caa cac ttg tgt ggt tct cac ttg gtt gaa gct ttg tac ttg gtt tgt      452
Gln His Leu Cys Gly Ser His Leu Val Glu Ala Leu Tyr Leu Val Cys
            100                 105                 110 ggt gaa aga ggt ttc ttc tac act gac aag gat ggg aag ggt atc gtt      500
Gly Glu Arg Gly Phe Phe Tyr Thr Asp Lys Asp Gly Lys Gly Ile Val
        115                 120                 125 gaa caa tgt tgt act tct atc tgt tct ttg tac caa ttg gaa aac          545
Glu Gln Cys Cys Thr Ser Ile Cys Ser Leu Tyr Gln Leu Glu Asn
130                 135                 140 tactgtaact agacgcagcc cgcaggctct agaaactaag attaatataa ttata          600
```

<210> SEQ ID NO 7
<211> LENGTH: 144
<212> TYPE: PRT
<213> ORGANISM: Artificial Sequence
<220> FEATURE:
<223> OTHER INFORMATION: Synthetic

<400> SEQUENCE: 7

```
Met Arg Phe Pro Ser Ile Phe Thr Ala Val Leu Phe Ala Ala Ser Ser
 1                5                  10                  15

Ala Leu Ala Ala Pro Val Asn Thr Thr Thr Glu Asp Glu Thr Ala Gln
             20                  25                  30

Ile Pro Ala Glu Ala Val Ile Gly Tyr Ser Asp Leu Glu Gly Asp Phe
         35                  40                  45

Asp Val Ala Val Leu Pro Phe Ser Asn Ser Thr Asn Asn Gly Leu Leu
     50                  55                  60

Phe Ile Asn Thr Thr Ile Ala Ser Ile Ala Ala Lys Glu Glu Gly Val
```

```
              65                  70                  75                  80
Ser Met Ala Lys Arg Glu Glu Ala Glu Ala Glu Ala Pro Lys Phe Val
                    85                  90                  95

Asn Gln His Leu Cys Gly Ser His Leu Val Glu Ala Leu Tyr Leu Val
            100                 105                 110

Cys Gly Glu Arg Gly Phe Phe Tyr Thr Asp Lys Asp Gly Lys Gly Ile
        115                 120                 125

Val Glu Gln Cys Cys Thr Ser Ile Cys Ser Leu Tyr Gln Leu Glu Asn
    130                 135                 140

<210> SEQ ID NO 8
<211> LENGTH: 6
<212> TYPE: PRT
<213> ORGANISM: Artificial Sequence
<220> FEATURE:
<223> OTHER INFORMATION: Synthetic

<400> SEQUENCE: 8

Glu Glu Gly Glu Pro Lys
1               5

<210> SEQ ID NO 9
<211> LENGTH: 550
<212> TYPE: DNA
<213> ORGANISM: Artificial Sequence
<220> FEATURE:
<221> NAME/KEY: CDS
<222> LOCATION: (115)...(489)
<223> OTHER INFORMATION: Synthetic

<400> SEQUENCE: 9
ttcttgctta aatctataac tacaaaaaac acatacagga attccattca agaatagttc        60
aaacaagaag attacaaact atcaatttca tacacaatat aaacgattaa aaga atg       117
                                                            Met
                                                            1 aaa ctg aaa act gta aga tct gcg gtc ctt tcg tca ctc ttt gca tct       165
Lys Leu Lys Thr Val Arg Ser Ala Val Leu Ser Ser Leu Phe Ala Ser
            5                   10                  15 cag gtc ctt ggc caa cca att gac gac act gaa tct aac act act tct       213
Gln Val Leu Gly Gln Pro Ile Asp Asp Thr Glu Ser Asn Thr Thr Ser
        20                  25                  30 gtc aac ttg atg gct gac gac act gaa tct aga ttc gct act aac act       261
Val Asn Leu Met Ala Asp Asp Thr Glu Ser Arg Phe Ala Thr Asn Thr
    35                  40                  45 act ttg gct ggt ggt ttg gat gtt gtt aac ttg atc tcc atg gct aag       309
Thr Leu Ala Gly Gly Leu Asp Val Val Asn Leu Ile Ser Met Ala Lys
50                  55                  60                  65 aga gaa gaa ggt gaa cca aag ttc gtt aac caa cac ttg tgt ggt tcc       357
Arg Glu Glu Gly Glu Pro Lys Phe Val Asn Gln His Leu Cys Gly Ser
                70                  75                  80 cac ttg gtt gaa gct ttg tac ttg gtt tgt ggt gaa aga ggt ttc ttc       405
His Leu Val Glu Ala Leu Tyr Leu Val Cys Gly Glu Arg Gly Phe Phe
            85                  90                  95 tac act gac aag gac ggt aag ggt atc gtt gaa caa tgt tgt act tct       453
Tyr Thr Asp Lys Asp Gly Lys Gly Ile Val Glu Gln Cys Cys Thr Ser
        100                 105                 110 atc tgt tct ttg tac caa ttg gaa aac tac tgt aac tagacgcagc            499
Ile Cys Ser Leu Tyr Gln Leu Glu Asn Tyr Cys Asn
    115                 120                 125 ccgcaggctc tagaaactaa gattaatata attatataaa aatattatct t              550
```

-continued

```
<210> SEQ ID NO 10
<211> LENGTH: 125
<212> TYPE: PRT
<213> ORGANISM: Artificial Sequence
<220> FEATURE:
<223> OTHER INFORMATION: Synthetic

<400> SEQUENCE: 10

Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Asn Thr Thr
            20                  25                  30

Ser Val Asn Leu Met Ala Asp Thr Glu Ser Arg Phe Ala Thr Asn
        35                  40                  45

Thr Thr Leu Ala Gly Gly Leu Asp Val Val Asn Leu Ile Ser Met Ala
 50                  55                  60

Lys Arg Glu Glu Gly Glu Pro Lys Phe Val Asn Gln His Leu Cys Gly
65                   70                  75                  80

Ser His Leu Val Glu Ala Leu Tyr Leu Val Cys Gly Glu Arg Gly Phe
                85                  90                  95

Phe Tyr Thr Asp Lys Asp Gly Lys Gly Ile Val Glu Gln Cys Cys Thr
            100                 105                 110

Ser Ile Cys Ser Leu Tyr Gln Leu Glu Asn Tyr Cys Asn
        115                 120                 125

<210> SEQ ID NO 11
<211> LENGTH: 550
<212> TYPE: DNA
<213> ORGANISM: Artificial Sequence
<220> FEATURE:
<221> NAME/KEY: CDS
<222> LOCATION: (115)...(486)
<223> OTHER INFORMATION: Synthetic

<400> SEQUENCE: 11
ttcttgctta aatctataac tacaaaaaac acatacagga attccattca agaatagttc      60
aaacaagaag attacaaact atcaatttca tacacaatat aaacgattaa aaga atg      117
                                                            Met
                                                             1 aaa ctg aaa act gta aga tct gcg gtc ctt tcg tca ctc ttt gca tct      165
Lys Leu Lys Thr Val Arg Ser Ala Val Leu Ser Ser Leu Phe Ala Ser
         5                  10                  15 cag gtc ctt ggc caa cca att gac gac act gaa tct caa act act tct      213
Gln Val Leu Gly Gln Pro Ile Asp Asp Thr Glu Ser Gln Thr Thr Ser
    20                  25                  30 gtc aac ttg atg gct gac gac act gaa tct gct ttc gct act caa act      261
Val Asn Leu Met Ala Asp Asp Thr Glu Ser Ala Phe Ala Thr Gln Thr
35                  40                  45 aac tct ggt ggt ttg gat gtt gtt ggt ttg atc tcc atg gct aag aga      309
Asn Ser Gly Gly Leu Asp Val Val Gly Leu Ile Ser Met Ala Lys Arg
 50                  55                  60                  65 gaa gaa ggt gaa cca aag ttc gtt aac caa cac ttg tgc ggt tcc cac      357
Glu Glu Gly Glu Pro Lys Phe Val Asn Gln His Leu Cys Gly Ser His
                70                  75                  80 ttg gtt gaa gct ttg tac ttg gtt tgc ggt gaa aga ggt ttc ttc tac      405
Leu Val Glu Ala Leu Tyr Leu Val Cys Gly Glu Arg Gly Phe Phe Tyr
            85                  90                  95 act gac aag gac ggt aag ggt atc gtt gaa caa tgc tgt acc tcc atc      453
Thr Asp Lys Asp Gly Lys Gly Ile Val Glu Gln Cys Cys Thr Ser Ile
        100                 105                 110 tgc tcc ttg tac caa ttg gaa aac tac tgc aac tagacgcagc ccgcaggctc    506
Cys Ser Leu Tyr Gln Leu Glu Asn Tyr Cys Asn
```

```
Cys Ser Leu Tyr Gln Leu Glu Asn Tyr Cys Asn
        115                 120 tagaaactaa gattaatata attatataaa aatattatct tctt              550

<210> SEQ ID NO 12
<211> LENGTH: 124
<212> TYPE: PRT
<213> ORGANISM: Artificial Sequence
<220> FEATURE:
<223> OTHER INFORMATION: Synthetic

<400> SEQUENCE: 12

Met Lys Leu Lys Thr Val Arg Ser Ala Val Leu Ser Ser Leu Phe Ala
 1               5                  10                  15

Ser Gln Val Leu Gly Gln Pro Ile Asp Asp Thr Glu Ser Gln Thr Thr
            20                  25                  30

Ser Val Asn Leu Met Ala Asp Asp Thr Glu Ser Ala Phe Ala Thr Gln
        35                  40                  45

Thr Asn Ser Gly Gly Leu Asp Val Val Gly Leu Ile Ser Met Ala Lys
    50                  55                  60

Arg Glu Glu Gly Glu Pro Lys Phe Val Asn Gln His Leu Cys Gly Ser
65                  70                  75                  80

His Leu Val Glu Ala Leu Tyr Leu Val Cys Gly Glu Arg Gly Phe Phe
                85                  90                  95

Tyr Thr Asp Lys Asp Gly Lys Gly Ile Val Glu Gln Cys Cys Thr Ser
            100                 105                 110

Ile Cys Ser Leu Tyr Gln Leu Glu Asn Tyr Cys Asn
        115                 120

<210> SEQ ID NO 13
<211> LENGTH: 27
<212> TYPE: DNA
<213> ORGANISM: Artificial Sequence
<220> FEATURE:
<223> OTHER INFORMATION: Synthetic

<400> SEQUENCE: 13
taaatctata actacaaaaa acacata                                 27

<210> SEQ ID NO 14
<211> LENGTH: 109
<212> TYPE: DNA
<213> ORGANISM: Artificial Sequence
<220> FEATURE:
<223> OTHER INFORMATION: Synthetic
<221> NAME/KEY: misc_feature
<222> LOCATION: (1)...(109)
<223> OTHER INFORMATION: n = A,T,C or G
<221> NAME/KEY: misc_feature
<222> LOCATION: (1)...(109)
<223> OTHER INFORMATION: m = C or A

<400> SEQUENCE: 14
ccaaagaaga tgtgactgtt cnnmcccttc ccatagcaac ttgttacaac atgaagatag   60
acaagaaaca tggttaacct tttgatgaca ttgatcagat ctttgattc               109

<210> SEQ ID NO 15
<211> LENGTH: 45
<212> TYPE: PRT
<213> ORGANISM: Artificial Sequence
<220> FEATURE:
<223> OTHER INFORMATION: Synthetic
```

```
<400> SEQUENCE: 15

Gln Pro Ile Asp Asp Thr Glu Ser Asn Thr Thr Ser Val Asn Leu Met
 1               5                  10                  15

Ala Asp Asp Thr Glu Ser Arg Phe Ala Thr Asn Thr Thr Leu Ala Gly
            20                  25                  30

Gly Leu Asp Val Val Asn Leu Ile Ser Met Ala Lys Arg
        35                  40                  45

<210> SEQ ID NO 16
<211> LENGTH: 44
<212> TYPE: PRT
<213> ORGANISM: Artificial Sequence
<220> FEATURE:
<223> OTHER INFORMATION: Synthetic

<400> SEQUENCE: 16

Gln Pro Ile Asp Asp Thr Glu Ser Gln Thr Thr Ser Val Asn Leu Met
 1               5                  10                  15

Ala Asp Asp Thr Glu Ser Ala Phe Ala Thr Gln Thr Asn Ser Gly Gly
            20                  25                  30

Leu Asp Val Val Gly Leu Ile Ser Met Ala Lys Arg
        35                  40

<210> SEQ ID NO 17
<211> LENGTH: 550
<212> TYPE: DNA
<213> ORGANISM: Artificial Sequence
<220> FEATURE:
<221> NAME/KEY: CDS
<222> LOCATION: (115)...(486)
<223> OTHER INFORMATION: Synthetic

<400> SEQUENCE: 17
ttcttgctta aatctataac tacaaaaaac acatacagga attccattca agaatagttc      60
aaacaagaag attacaaact atcaatttca tacacaatat aaacgattaa aaga atg      117
                                                            Met
                                                             1 aaa ctg aaa act gta aga tct gcg gtc ctt tcg tca ctc ttt gca tct      165
Lys Leu Lys Thr Val Arg Ser Ala Val Leu Ser Ser Leu Phe Ala Ser
         5                  10                  15 cag gtc ctt ggc caa cca att gac gac act gaa tct caa act act tct      213
Gln Val Leu Gly Gln Pro Ile Asp Asp Thr Glu Ser Gln Thr Thr Ser
        20                  25                  30 gtc aac ttg atg gct gac gac act gaa tct gct ttc gct act caa act      261
Val Asn Leu Met Ala Asp Asp Thr Glu Ser Ala Phe Ala Thr Gln Thr
    35                  40                  45 aac tct ggt ggt ttg gat gtt gtt ggt ttg atc tcc atg gct aag aga      309
Asn Ser Gly Gly Leu Asp Val Val Gly Leu Ile Ser Met Ala Lys Arg
 50                  55                  60                  65 gaa gaa ggt gaa cca aag ttc gtt aac caa cac ttg tgc ggt tcc cac      357
Glu Glu Gly Glu Pro Lys Phe Val Asn Gln His Leu Cys Gly Ser His
                 70                  75                  80 ttg gtt gaa gct ttg tac ttg gtt tgc ggt gaa aga ggt ttc ttc tac      405
Leu Val Glu Ala Leu Tyr Leu Val Cys Gly Glu Arg Gly Phe Phe Tyr
             85                  90                  95 act cct aag gct gct aag ggt att gtc gaa caa tgc tgt acc tcc atc      453
Thr Pro Lys Ala Ala Lys Gly Ile Val Glu Gln Cys Cys Thr Ser Ile
        100                 105                 110 tgc tcc ttg tac caa ttg gaa aac tac tgc aac tagacgcagc ccgcaggctc    506
Cys Ser Leu Tyr Gln Leu Glu Asn Tyr Cys Asn
    115                 120
```

-continued

```
tagaaactaa gattaatata attatataaa aatattatct tctt                550
```

<210> SEQ ID NO 18
<211> LENGTH: 124
<212> TYPE: PRT
<213> ORGANISM: Artificial Sequence
<220> FEATURE:
<223> OTHER INFORMATION: Synthetic

<400> SEQUENCE: 18

```
Met Lys Leu Lys Thr Val Arg Ser Ala Val Leu Ser Ser Leu Phe Ala
  1               5                  10                  15

Ser Gln Val Leu Gly Gln Pro Ile Asp Asp Thr Glu Ser Gln Thr Thr
                 20                  25                  30

Ser Val Asn Leu Met Ala Asp Asp Thr Glu Ser Ala Phe Ala Thr Gln
             35                  40                  45

Thr Asn Ser Gly Gly Leu Asp Val Val Gly Leu Ile Ser Met Ala Lys
         50                  55                  60

Arg Glu Glu Gly Glu Pro Lys Phe Val Asn Gln His Leu Cys Gly Ser
 65                  70                  75                  80

His Leu Val Glu Ala Leu Tyr Leu Val Cys Gly Glu Arg Gly Phe Phe
                 85                  90                  95

Tyr Thr Pro Lys Ala Ala Lys Gly Ile Val Glu Gln Cys Cys Thr Ser
                100                 105                 110

Ile Cys Ser Leu Tyr Gln Leu Glu Asn Tyr Cys Asn
            115                 120
```

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19

```
ttgcttaaat ctataactac                                            20
```

<210> SEQ ID NO 20
<211> LENGTH: 108
<212> TYPE: DNA
<213> ORGANISM: Artificial Sequence
<220> FEATURE:
<223> OTHER INFORMATION: Synthetic
<221> NAME/KEY: misc_feature
<222> LOCATION: (1)...(108)
<223> OTHER INFORMATION: n = A,T,C or G
<221> NAME/KEY: misc_feature
<222> LOCATION: (1)...(18)
<223> OTHER INFORMATION: m = G or T

<400> SEQUENCE: 20

```
ttagtttcta gactagttgc agtagttttc caattggtac aaggagcaga tggaggtaca   60
gcattgttcg acaataccct taccmnnctt aggagtgtag aagaaacc              108
```